US011571279B2

(12) United States Patent
Wang et al.

(10) Patent No.: US 11,571,279 B2
(45) Date of Patent: Feb. 7, 2023

(54) ALIGNER DAMAGE PREDICTION AT WEAK SPOTS WITH SIMULATION

(71) Applicant: Align Technology, Inc., San Jose, CA (US)

(72) Inventors: Yuxiang Wang, Newark, CA (US); Rohit Tanugula, San Jose, CA (US); Reza Shirazi Aghjari, San Jose, CA (US); Chunhua Li, Cupertino, CA (US); Jun Sato, San Jose, CA (US); Luyao Cai, San Jose, CA (US); Kangning Su, Arlington, VA (US)

(73) Assignee: Align Technology, Inc., San Jose, CA (US)

( * ) Notice: Subject to any disclaimer, the term of this patent is extended or adjusted under 35 U.S.C. 154(b) by 137 days.

(21) Appl. No.: 16/584,788

(22) Filed: Sep. 26, 2019

(65) Prior Publication Data
US 2020/0100864 A1 Apr. 2, 2020

Related U.S. Application Data

(60) Provisional application No. 62/737,458, filed on Sep. 27, 2018.

(51) Int. Cl.
*A61C 7/00* (2006.01)
*G06F 17/18* (2006.01)
(Continued)

(52) U.S. Cl.
CPC ............... *A61C 7/002* (2013.01); *A61C 7/08* (2013.01); *A61C 9/004* (2013.01); *A61C 13/34* (2013.01);
(Continued)

(58) Field of Classification Search
CPC ......... A61C 7/002; A61C 9/004; A61C 13/34; A61C 7/08; G06F 30/23; G06F 17/18;
(Continued)

(56) References Cited

U.S. PATENT DOCUMENTS 5,975,893 A 11/1999 Chishti et al.
6,309,215 B1 10/2001 Phan et al.
(Continued)

FOREIGN PATENT DOCUMENTS

WO 2006050452 A2 5/2006

OTHER PUBLICATIONS

Cowley, Daniel P., "Effect of Gingival Margin Design on Retention of Thermoformed Orthodontic Aligners" (2012). UNLV Theses, Dissertations, Professional Papers, and Capstones. 1662. http://dx.doi.org/10.34917/4332643 (Year: 2012).*

(Continued)

*Primary Examiner* — Bijan Mapar
*Assistant Examiner* — Pursottam Giri
(74) *Attorney, Agent, or Firm* — Lowenstein Sandler LLP

(57) ABSTRACT

Embodiments relate to an aligner breakage solution that tests probability of aligner breakage at weak points. A method includes gathering a digital model representing an aligner for a dental arch of a patient, receiving material property information for a material to be used to manufacture the aligner, and analyzing one or more regions of the aligner. Analyzing a region of the aligner comprises simulating application of a load around the region, determining at least one of a stress, a strain or a strain energy density at the region, evaluating a strength of the aligner at the region, and determining whether the region satisfies a damage criterion based on the strength of the aligner at the region.

31 Claims, 36 Drawing Sheets

(51) Int. Cl.
| | |
|---|---|
| *G06N 20/00* | (2019.01) |
| *A61C 7/08* | (2006.01) |
| *G06F 30/23* | (2020.01) |
| *G16H 50/50* | (2018.01) |
| *G01N 33/44* | (2006.01) |
| *B33Y 80/00* | (2015.01) |
| *A61C 9/00* | (2006.01) |
| *A61C 13/34* | (2006.01) |
| *B29C 33/38* | (2006.01) |
| *B29C 51/30* | (2006.01) |
| *G06F 30/27* | (2020.01) |
| *B29C 73/00* | (2006.01) |
| *G06F 30/20* | (2020.01) |
| *G06F 119/18* | (2020.01) |
| *G06F 113/22* | (2020.01) |
| *G06F 111/10* | (2020.01) |
| *B33Y 50/00* | (2015.01) |
| *B29L 31/00* | (2006.01) |

(52) U.S. Cl.
CPC .......... *B29C 33/3835* (2013.01); *B29C 51/30* (2013.01); *B29C 73/00* (2013.01); *B33Y 80/00* (2014.12); *G01N 33/442* (2013.01); *G06F 17/18* (2013.01); *G06F 30/20* (2020.01); *G06F 30/23* (2020.01); *G06F 30/27* (2020.01); *G06N 20/00* (2019.01); *G16H 50/50* (2018.01); *B29L 2031/753* (2013.01); *B33Y 50/00* (2014.12); *G06F 2111/10* (2020.01); *G06F 2113/22* (2020.01); *G06F 2119/18* (2020.01)

(58) Field of Classification Search
CPC ............. G06F 2119/18; G06F 2113/22; G06F 2111/10; G16H 50/50; G01N 33/442; B33Y 80/00; B33Y 50/00; B29C 33/3835; B29C 51/30; G06N 20/00; G06N 5/046; G06N 7/005; B29L 2031/753
See application file for complete search history.

(56) References Cited

U.S. PATENT DOCUMENTS

| | | | |
|---|---|---|---|
| 6,450,807 B1 | 9/2002 | Chishti et al. | |
| 6,749,414 B1 | 6/2004 | Hanson et al. | |
| 6,830,450 B2 | 12/2004 | Knopp et al. | |
| 7,892,474 B2 | 2/2011 | Shkolnik et al. | |
| 8,684,729 B2 | 4/2014 | Wen | |
| 10,383,705 B2 | 8/2019 | Shanjani et al. | |
| 10,624,718 B2 | 4/2020 | Kuo et al. | |
| 10,717,208 B1 * | 7/2020 | Raslambekov | B29C 64/386 |
| 10,869,738 B2 | 12/2020 | Witte et al. | |
| 10,888,396 B2 | 1/2021 | Yaser | |
| 10,912,627 B2 | 2/2021 | Kuo et al. | |
| 11,026,831 B2 | 6/2021 | Kuo | |
| 2004/0120570 A1 | 6/2004 | Levi et al. | |
| 2005/0191593 A1 | 9/2005 | Knopp | |
| 2006/0131770 A1 | 6/2006 | Dierkes et al. | |
| 2007/0238064 A1 | 10/2007 | Stark et al. | |
| 2009/0191503 A1 * | 7/2009 | Matov | A61C 7/16 |
| | | | 433/24 |
| 2010/0322506 A1 | 12/2010 | Muramatsu et al. | |
| 2011/0039223 A1 * | 2/2011 | Li | B29B 11/14 |
| | | | 433/6 |
| 2013/0095446 A1 | 4/2013 | Andreiko et al. | |
| 2014/0061974 A1 | 3/2014 | Tyler | |
| 2014/0265034 A1 | 9/2014 | Dudley | |
| 2015/0060667 A1 | 3/2015 | Yamaguchi et al. | |
| 2015/0097315 A1 | 4/2015 | DeSimone et al. | |
| 2015/0097316 A1 | 4/2015 | DeSimone et al. | |
| 2015/0102532 A1 | 4/2015 | DeSimone et al. | |
| 2015/0335404 A1 * | 11/2015 | Webber | B29C 51/34 |
| | | | 264/16 |
| 2016/0110859 A1 | 4/2016 | Luoh et al. | |
| 2016/0128803 A1 | 5/2016 | Webber et al. | |
| 2016/0300338 A1 | 10/2016 | Zafar et al. | |
| 2017/0007359 A1 | 1/2017 | Kopelman et al. | |
| 2017/0007360 A1 | 1/2017 | Kopelman et al. | |
| 2017/0007361 A1 | 1/2017 | Boronkay et al. | |
| 2017/0007362 A1 | 1/2017 | Chen et al. | |
| 2017/0007363 A1 | 1/2017 | Boronkay | |
| 2017/0007365 A1 * | 1/2017 | Kopelman | A61C 7/08 |
| 2017/0007366 A1 | 1/2017 | Kopelman et al. | |
| 2017/0007367 A1 | 1/2017 | Li et al. | |
| 2017/0007368 A1 | 1/2017 | Boronkay | |
| 2017/0007386 A1 | 1/2017 | Mason et al. | |
| 2017/0008333 A1 | 1/2017 | Mason et al. | |
| 2017/0100209 A1 * | 4/2017 | Wen | A61C 7/08 |
| 2018/0116762 A1 | 5/2018 | Kopelman | |
| 2019/0102880 A1 | 4/2019 | Parpara et al. | |
| 2019/0105127 A1 | 4/2019 | Velazquez et al. | |
| 2019/0295254 A1 | 9/2019 | Parpara et al. | |
| 2019/0338067 A1 | 11/2019 | Liska et al. | |
| 2019/0345276 A1 | 11/2019 | Liska et al. | |
| 2020/0100865 A1 | 4/2020 | Wang et al. | |
| 2020/0100866 A1 | 4/2020 | Medvinskaya et al. | |
| 2020/0100871 A1 | 4/2020 | Wang et al. | |
| 2020/0113652 A1 * | 4/2020 | Raby | A61C 9/004 |

OTHER PUBLICATIONS

Barone, S., Paoli, A., Razionale, A.V. et al. Computer aided modelling to simulate the biomechanical behaviour of customised orthodontic removable appliances. Int J Interact Des Manuf 10, 387-400 (2016). (Year: 2016).*

Barone, S., Paoli, A., Razionale, A., & Savignano, R. (2016). Design of Customised Orthodontic Devices by Digital Imaging and CAD/FEM Modelling. Bioimaging. (Year: 2016).*

International Search Report and Written Opinion of the International Searching Authority for International Patent Application No. PCT/US2019/053663 dated Jan. 31, 2020, 13 pages.

Barone. S., et al., "Computational Design and Engineering of Polymeric Orthodontic Aligners," International Journal for Numerical Methods in Biomedical Engineering, Aug. 2017, vol. 33(8):e2839.

Chan. L., et al., "Clear Aligner Treatment With "in-office" Virtual Model Set-up and 3D Printing," Journal of Dentistry and Oral Care, 2017, vol. 3(1), pp. 21-25.

Geramy., et al., "Anterior Teeth Splinting After Orthodontic Treatment: 3D Analysis Using Finite Element Method," Journal of Dentistry, 2012, vol. 9(2), pp. 90-98.

Wishney. M., "Potential Risks of Orthodontic Therapy: A Critical Review and Conceptual Framework," Australian Dental Journal, Mar. 2017, vol. 62, pp. 86-96.

Yokoi. Y., et al., "Effects of Attachment of Plastic Aligner in Closing of Diastema of Maxillary Dentition by Finite Element Method," Journal of Healthcare Engineering, Mar. 2019, Article ID. 1075097, 6 pages.

* cited by examiner

1550

Apply a first orthodontic appliance to a patient's teeth to reposition the teeth from a first tooth arrangement to a second tooth arrangement 1560

Apply a second orthodontic appliance to the patient's teeth to reposition the teeth from the second tooth arrangement to a third tooth arrangement 1570

Determine a movement path to move one or more teeth from an initial arrangement to a target arrangement
1610

Determine a force system to produce movement of the one or more teeth along the movement path
1620

Determine an arch or palate expander design for an orthodontic appliance configured to produce the force system
1630

Determine instructions for fabrication of the orthodontic appliance incorporating the arch or palate expander design
1640

FIG. 16

```
┌─────────────────────────────────────────────────────────────────────┐
│ Gather a first digital model representing a dental arch-like structure of a patient, wherein │
│ the dental arch-like structure comprises one or more teeth-like structures to interface │
│ with a polymeric aligner 1802 │
└─────────────────────────────────────────────────────────────────────┘
                                    │
                                    ▼
┌─────────────────────────────────────────────────────────────────────┐
│ Gather a second digital model representing the polymeric aligner to be supported by the │
│ dental arch-like structure, wherein the second digital model of the polymeric aligner │
│ specifies first one or more physical properties of the polymeric aligner at one or more │
│ regions of the polymeric aligner 1804 │
└─────────────────────────────────────────────────────────────────────┘
                                    │
                                    ▼
┌─────────────────────────────────────────────────────────────────────┐
│ Simulate an interaction of the polymeric aligner to the dental arch-like structure using │
│ the first digital model and the second digital model 1806 │
└─────────────────────────────────────────────────────────────────────┘
                                    │
                                    ▼
┌─────────────────────────────────────────────────────────────────────┐
│ Simulate a removal of the polymeric aligner from the dental arch-like structure using the │
│ first digital model and the second digital model to obtain a simulated removal of the │
│ polymeric aligner from the dental arch-like structure 1808 │
└─────────────────────────────────────────────────────────────────────┘
                                    │
                                    ▼
┌─────────────────────────────────────────────────────────────────────┐
│ Determine a likeness that one or more physical values at the one or more regions will │
│ satisfy one or more damage criteria based on an interaction of the dental arch-like │
│ structure and the first one or more physical properties of the polymeric aligner, the │
│ interaction being due to the simulated removal 1810 │
└─────────────────────────────────────────────────────────────────────┘
                                    │
                                    ▼
┌─────────────────────────────────────────────────────────────────────┐
│ Analyze the second digital model for one or more likely points of physical damage │
│ based on the determination of the likeness of the one or more physical strains 1812 │
└─────────────────────────────────────────────────────────────────────┘
                                    │
                                    ▼
┌─────────────────────────────────────────────────────────────────────┐
│ In response to analyzing the second digital model for the one or more likely points of │
│ physical damage, determining whether to implement one or more corrective actions for │
│ the polymeric aligner 1814 │
└─────────────────────────────────────────────────────────────────────┘
                                    │
                                    ▼
┌─────────────────────────────────────────────────────────────────────┐
│ Generate a third digital model representing the polymeric aligner, the third digital model │
│ being based on the second digital model and the one or more corrective actions for the │
│ polymeric aligner 1816 │
└─────────────────────────────────────────────────────────────────────┘
```

ALIGNER DAMAGE PREDICTION AT WEAK SPOTS WITH SIMULATION

RELATED APPLICATIONS

This patent application claims the benefit under 35 U.S.C. § 119(e) of U.S. Provisional Application No. 62/737,458, filed Sep. 27, 2018, which is incorporated by reference herein.

TECHNICAL FIELD

The present disclosure relates to the field of designing dental appliances, such as polymeric orthodontic aligners and, in particular, to designing physical properties of polymeric aligners in light of desired or acceptable manufacturing or clinical outcomes that may be achieved by those polymeric aligners, and to predicting failures of such polymeric aligners.

BACKGROUND

An objective of orthodontics is to move a patient's teeth to positions where function and/or aesthetics are optimized. Traditionally, appliances such as braces are applied to a patient's teeth by an orthodontist or dentist and the set of braces exerts continual force on the teeth and gradually urges them toward their intended positions. Over time and with a series of clinical visits and adjustments to the braces, the orthodontist adjusts the appliances to move the teeth toward their final destination.

Alternatives to conventional orthodontic treatment with traditional affixed appliances (e.g., braces) include systems including a series of preformed aligners. In these systems, multiple, and sometimes all, of the aligners to be worn by a patient may be designed and/or fabricated before the aligners are administered to a patient and/or reposition the patient's teeth (e.g., at the outset of treatment). The design and/or planning of a customized treatment for a patient may make use of computer-based three-dimensional (3D) planning/design tools. The design of the aligners can rely on computer modeling of a series of planned successive tooth arrangements, and the individual aligners are designed to be worn over the teeth and elastically reposition the teeth to each of the planned tooth arrangements.

Once designed and/or planned, a series of preformed aligners may be fabricated from a material that, alone or in combination with attachments on a patient's teeth, imparts forces to the patient's teeth. Example materials include one or more polymeric materials. Fabrication may involve thermoforming aligners using a series of molds (e.g., 3D-printed molds) and/or directly fabricating the aligners. For some thermoforming fabrication techniques, shells are formed around molds to achieve negatives of the molds. The shells are then removed from the molds to be used for various applications. One example application in which a shell is formed around a mold and then later used is corrective dentistry or orthodontic treatment. In such an application, the mold may be a positive mold of a dental arch for a patient and the shell may be an aligner to be used for aligning one or more teeth of the patient. When attachments (e.g., planned orthodontic attachments) are used, the mold may also include features associated with the attachments.

Molds may be formed using a variety of techniques, such as with casting or rapid prototyping equipment. For example, 3D printers may manufacture molds of aligners using additive manufacturing techniques (e.g., stereolithography) or subtractive manufacturing techniques (e.g., milling). The aligners may then be formed over the molds using thermoforming techniques. Once an aligner is formed, it may be manually or automatically trimmed. In some instances, a computer controlled 4-axis or 5-axis trimming machine (e.g., a laser trimming machine or a mill) is used to trim the aligner along a cutline. The trimming machine uses electronic data that identifies the cutline to trim the aligner. Thereafter, the aligner may be removed from the mold and delivered to the patient. As another example, aligners may be directly fabricated using, e.g., stereolithography (SLA), digital light processing (DLP), and/or other 3D printing techniques.

While it may be desirable to identify specific portions of aligners prone to deformation, warpage and/or breakage during fabrication (e.g., in response to removal from a mold) and/or use (e.g., in response to removal from a patient's dentition), existing techniques make it difficult to do so.

BRIEF DESCRIPTION OF THE DRAWINGS

The present disclosure is illustrated by way of example, and not by way of limitation, in the figures of the accompanying drawings.

FIG. 15C illustrates a method of orthodontic treatment using a plurality of appliances, in accordance with embodiments.

FIG. 16 illustrates a method for designing an orthodontic appliance, in accordance with embodiments.

FIG. 18 illustrates another method for implementing one or more corrective actions to a polymeric aligner based on a simulated removal of the polymeric aligner from a dental arch.

DETAILED DESCRIPTION

Figure 15A:
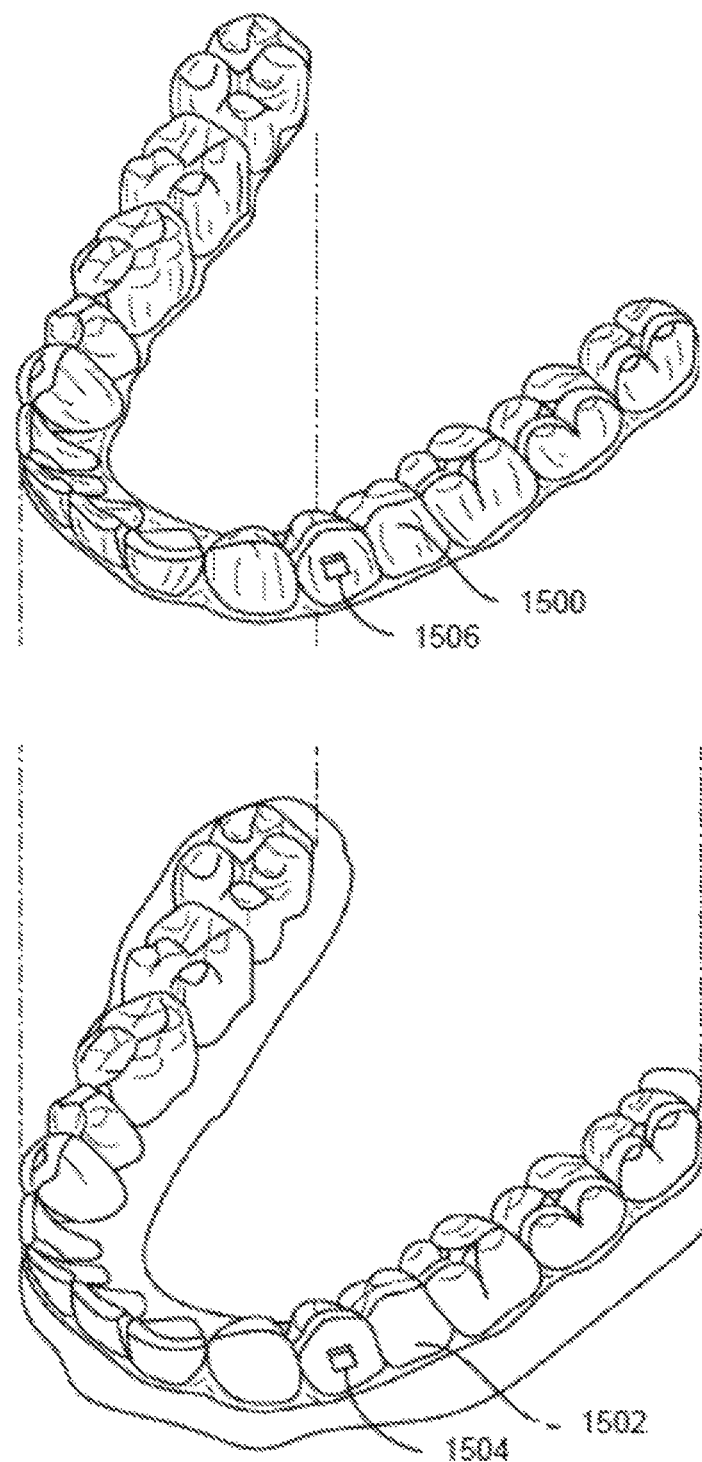
FIG. 15A illustrates a tooth repositioning appliance, in accordance with embodiments.

Aligners (also referred to herein as "orthodontic aligners") may be one type of dental appliance (also referred to herein as "appliance") applied to a patient's dentition and used to treat malocclusions. Examples of aligners and aligner systems may be found in FIGS. 15A and 15B. An example treatment method using aligners is shown in FIG. 15C. Aligners may be formed from polymeric materials using indirect or direct fabrication techniques, examples of which may be found in conjunction with the discussion of FIGS. 15A, 15B, and 15C. As noted further herein, during the indirect fabrication of aligners, many aligners may experience strains/stresses from being removed from molds. Additionally, during use (whether aligners are formed indirectly or directly), many aligners may experience strains/stresses from residing in an intra-oral environment for extended periods of time (e.g., up to twenty-three hours a day for several weeks) or from being repeatedly removed (e.g., up to several times a day for several weeks) from a patient's dentition. The strains/stresses may result in physical damage (deformation (permanent or otherwise), warpage, breakage, cracks, damage, etc.) of aligners. Physical damage during manufacturing processes may present serious problems, including materials waste issues, supply chain issues, and inability to meet consumer demands. Physical damage during use may also present serious problems, such as adversely affecting staging scenarios and/or the efficacy of treatment plans.

The embodiments herein relate to systems, methods, and/or computer-readable media suitable for predicting deformation, warpage, and/or breakage of custom manufactured products (e.g., of aligners) prior to and/or during fabrication (e.g., in response to removal from a mold) and/or use (e.g., in response to removal from a patient's dentition). Also discussed are embodiments that cover resolving and/or mitigating predicted points of damage. The embodiments described herein further cover techniques to optimize properties, such as thicknesses, of aligners by predicting portions of aligners that are prone to deformation, warpage, breakage, etc., and by identifying the extent these properties accord with desired and/or actual clinical goals. Various embodiments may further use optimized properties of aligners as the basis of efficient aligner manufacturing processes, customized and/or optimized treatment plans, etc. Alone and together, these features may be considered as one or more aligner damage solutions, e.g., solutions that accommodate possible physical damage to aligners through manufacturing, use, etc. . . . .

More specifically, in some embodiments, the aligner damage solution systems and methods may be implemented during the design of orthodontic aligners prior to and/or during manufacturing. Designing custom manufactured products can be particularly difficult, especially in orthodontic aligner manufacturing scenarios in which orthodontic aligners are individually customized for every single patient. Additionally, many orthodontic treatment plans prescribe treatment by a series of aligners that are manufactured for a patient. Each aligner in the series of aligners may implement a specific stage of a treatment plan, and/or have unique properties (e.g., shape(s)) compared to other aligners in the series of aligners. Additionally, many orthodontic treatment plans may provide patients with a pair of aligners for each stage of treatment, one unique upper aligner for treating the upper dental arch and one unique lower aligner for treating the lower dental arch. As a result, in some instances, a single treatment can include 50-60 stages for treating a complex case, meaning 100-120 unique aligners are designed to be manufactured for a single patient.

Further, for aligners manufactured by indirect fabrication techniques (e.g., thermoforming), removing an aligner from a mold may cause force(s) and/or a moment(s) to be applied to the aligner. In some instances, the polymeric materials of the aligners may break, warp, and/or deform during the removal process due to the force exerted. Further, removing aligners from a patient's teeth may cause force(s) and/or torque(s) to be exerted on the aligners, which may also break, warp, or deform the aligners. Patients may request a replacement aligner if the aligner breaks. As a result, another aligner is manufactured and shipped to the patient. As may be appreciated, as the number of replacement aligners increases, so too does the cost of manufacturing. In some instances, a replacement aligner may be manually modified post manufacturing to attempt to account for possible breakage. For example, if a certain interproximal region is identified where the aligner broke, a filler material may be added to the aligner to strengthen the aligner. Manually modifying the aligners post manufacturing may be cumbersome and slow, especially if there are hundreds, thousands, or more replacement aligners requested. Further, modifying the replacement aligners is a reactive process that is performed after the original aligner had an issue. Accordingly, embodiments of the present disclosure may provide a more scalable, automated, and/or proactive solution that may detect probable points of damage in a design of an aligner and perform one or more corrective actions prior to the aligner being manufactured. Embodiments may reduce the occurrence of aligner damage, and thus may also reduce the number of replacement aligners that are manufactured. Such reduction in damages may reduce the overall cost of manufacturing aligners and may reduce the amount of time that technicians spend on resolving aligner damages.

As noted herein, an aligner may be formed from a polymeric shell that is configured to receive an upper or lower dental arch of a patient at a particular treatment stage. Each aligner may be configured to apply forces to the patient's teeth at the particular stage of the orthodontic treatment. The aligners each have teeth-receiving cavities that receive and resiliently reposition the teeth in accordance with a particular treatment stage. Each tooth-receiving cavity may be referred to as a "cap". Teeth may be repositioned by the aligners by, for example, moving one or more teeth vertically (e.g., extruding or intruding teeth), rotating one or more teeth (e.g., through moments applied to the teeth, through second/third order rotations, etc.), moving one or more teeth in a transverse direction relative to the dental arch, and/or moving one or more teeth in an anterior-posterior direction relative to the dental arch. Each aligner may additionally include shapes that accommodate features attached to a patient's dentition that facilitate tooth repositioning and/or rotation.

Embodiments may identify individual aligners that include probable points of failure and/or may identify sets of aligners (e.g., for a patient or for a particular dental arch of a patient) that include one more aligner with a probable point of failure. Manufacturing flows may be determined for aligners based upon a likelihood that those aligners will become damaged (e.g., will develop a point of damage). Manufacturing flows may also be determined for sets of aligners (e.g., all aligners associated with a treatment plan for a patient, or all aligners associated with a treatment plan for an upper or lower dental arch of the patient) based on the probability that any aligners in the set of aligner will become damaged or experience a failure.

As mentioned above, the embodiments may determine various probable points of damage for a given set of digital designs of aligners. One or more probable points of damage may include one or more of breakage, warpage, deformation, failure, and so forth. Detecting the probable points of damage may enable modifying or fixing the digital design of the aligner to remove the probable points of damage prior to manufacturing the aligner, thereby increasing the yield of aligners that are successfully manufactured, reducing the number of patient complaints related to the aligners failing, reducing manufacturing cost of replacement aligners, and/or preventing the manufacturing of an aligner including a probable point of damage. It is noted that "probable" points of damage (used interchangeably with "likely" points of failure), as used herein, may refer to a likeliness of damage to a given region of an aligner by, e.g., manufacturing or use. Probable points of damage need not indicate damage by, e.g., a preponderance. Probable points of damage may indicate likeliness of damage beyond any specified threshold, including by a preponderance.

In some embodiments, the determination of the probable points of damage may be made based on a digital design of the aligner. The digital design of the aligner may refer to a digital model of the aligner including a geometry of the aligner. In some embodiments, the digital model for each aligner may be included in a digital file associated with the aligner. In some embodiments, the digital model of the aligner may be generated based on scanning the aligner (e.g., using an intraoral scanner or other 3D scanner) and generating the digital model of the aligner from a result of the scanning. In other embodiments, the digital model of the aligner may be generated using a digital model of a mold of the dental arch of the patient. The digital model of the mold may be offset (e.g., enlarged) to generate the digital model of the aligner. The "digital design of the aligner" and the "digital model of the aligner" may be used interchangeably herein. An analysis may be performed on the digital design of the aligner using at least one of a) a trained machine learning model trained to identify aligners having probable points of damage, b) a numerical simulation associated with removal of the aligner from a mold of the dental arch of the patient, c) a numerical simulation associated with progressive damage to the aligner, d) a numerical simulation that simulates loading around weak spots (e.g., interproximal regions) in the aligner, e) a geometry evaluator that calculates and evaluates geometry-related parameters (e.g., cross-sectional parameters) of the aligner (e.g., that evaluates a parameters associated with a geometry of the aligner), or f) a rules engine including one or more rules associated with parameters of aligners indicative of points of damage. Based on the analysis, a determination may be made as to whether the digital design of the aligner includes one or more probable points of damage. For a probable point of damage to be present, there is at least a threshold probability that breakage, deformation, warpage, failure, etc. will occur. In response to determining that the digital design of the aligner includes the one or more probable points of damage, one or more corrective actions (e.g., modifying the digital design of the aligner, modifying attachments in the digital design of the aligner, providing a notification to a dental practitioner, etc.) may be performed based on the one or more probable points of damage. Some advantages of the disclosed embodiments may include automated detection of various probable points of damage in aligners, automated correction of the probable points of damage in aligners, and/or automated selection of a manufacturing flow for aligners based on the existence or lack of probable points of failure/damage in the aligners. The embodiments may also reduce the number of replacement aligners that are manufactured, thereby reducing manufacturing costs and improving customer satisfaction. In some implementations, the determination of probable points of damage may form the basis of the design of aligners having variable thicknesses to accommodate those points of damage. Such variable thicknesses to accommodate points of damage may be formed through direct fabrication techniques and/or other techniques. Further, the embodiments may improve the number of aligners that are manufactured without breakages, warpages, or deformations.

Figure 14:
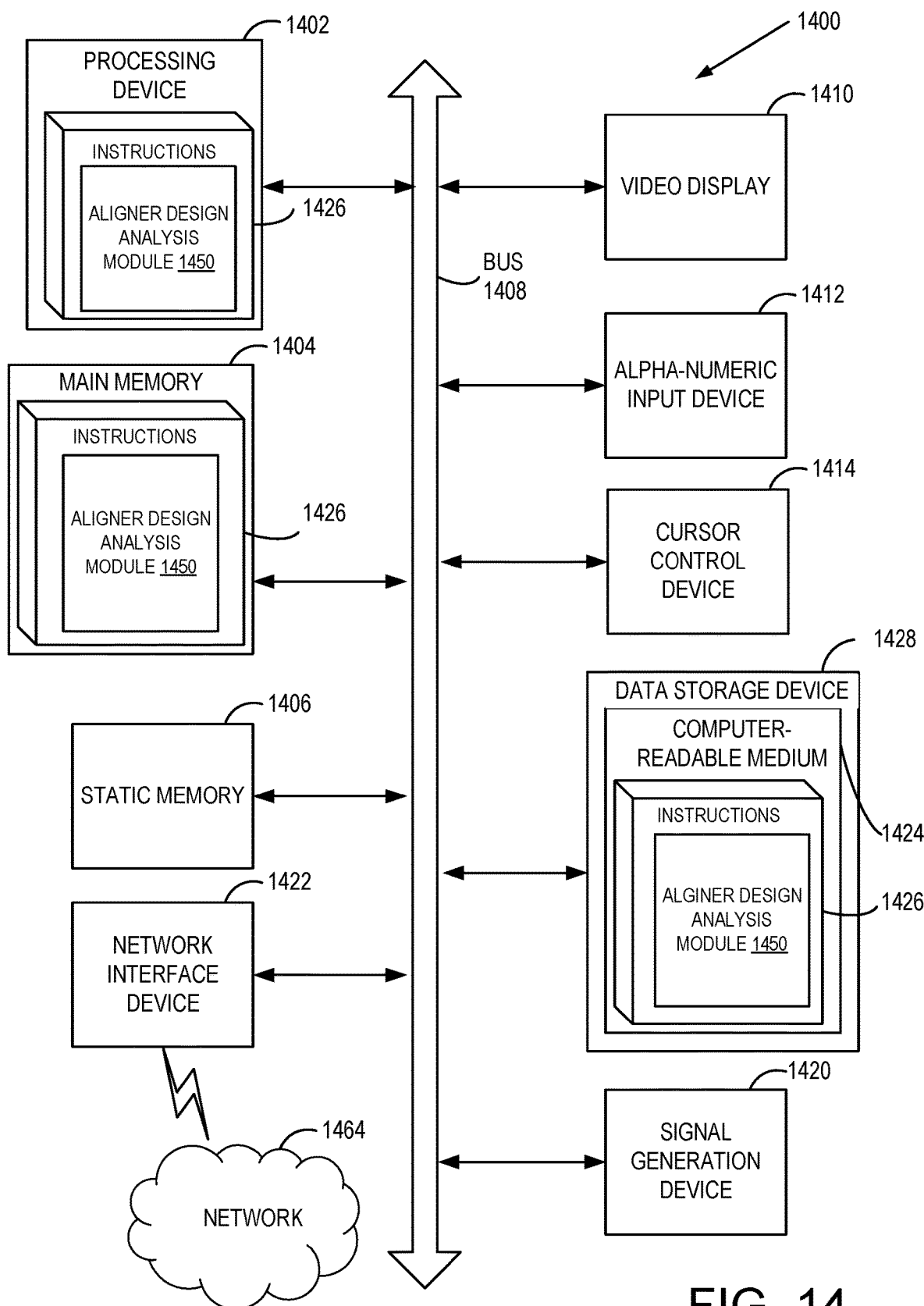
FIG. 14 illustrates a block diagram of an example computing device, in accordance with embodiments of the present disclosure.

Various software and/or hardware components may be used to implement the disclosed embodiments as shown in FIG. 14. For example, software components may include computer instructions stored in a tangible, non-transitory computer-readable media that are executed by one or more processing devices to perform the aligner damage solution on digital designs of aligners. Hardware components may include a processing device, memory device, network device, and so forth.

The shape of an aligner, including the shapes of each tooth receiving cavity (cap) in the aligner, the shapes of interproximal regions between tooth receiving cavities, the shapes of the outlines, the shapes of additional cavities formed to accommodate attachments on a patient's teeth, and so on all affect whether a particular aligner will break, warp or become otherwise deformed or damaged during removal of the aligner from a dental arch-like structure (e.g., mold and/or a patient's dentition). As noted herein, the shape of an aligner may be modified to accommodate probable points of damage and may form the basis of an aligner with variable thicknesses. An aligner with a modified shape may be formed by various techniques, including but not limited to direct fabrication techniques.

In the embodiments disclosed herein, the digital design of each aligner for a treatment plan or each aligner in specific stages of the treatment plan may be analyzed to determine whether one or more probable points of damage are present at any locations of the digital design of the aligner. Each digital design of an aligner may be associated with a digital design of a dental arch at a treatment stage for a patient. If one or more probable points of damage are detected for a digital design of an aligner, corrective actions may be performed based on the probable points of damage.

Embodiments are described with reference to aligners and orthodontic aligners (e.g., polymeric aligners and polymeric orthodontic aligners). Aligners are one form of dental appliance (also referred to simply as an appliance for convenience). In particular, as described above and in greater detail below, aligners may be a type of polymeric shell used to correct, for example, malocclusions. It should be understood that the embodiments described herein with reference to aligners also apply to other types of dental appliances and shells, and in particular to other types of polymeric dental appliances, including but not limited to sleep apnea treatment devices, night guards, and so on.

Figure 1A:
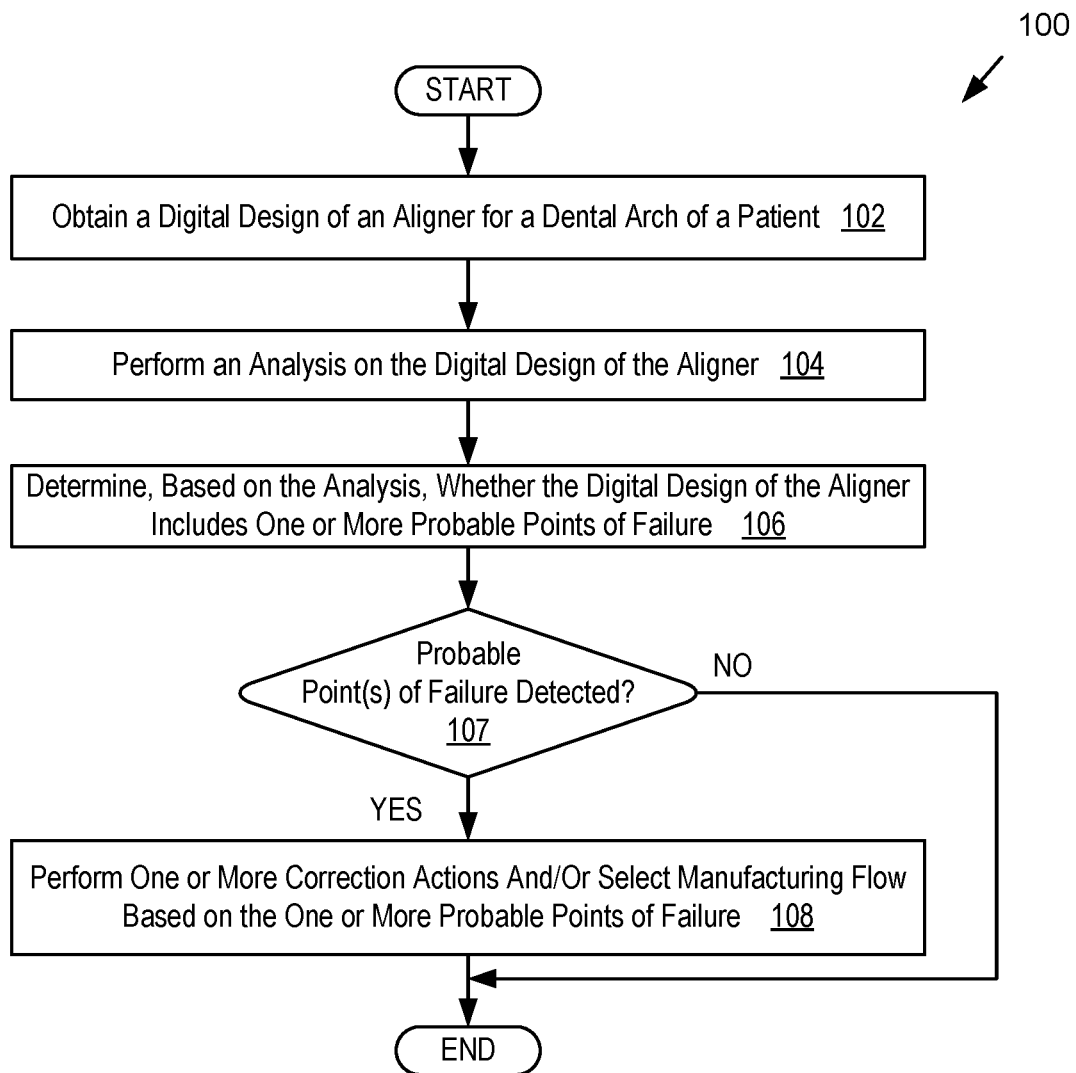
FIG. 1A illustrates a flow diagram for a method of performing a corrective analysis on a digital design of a polymeric aligner, in accordance with one embodiment.

Once designed, each aligner may be manufactured by forming polymeric material to implement one or more stages of a treatment plan on a patient's dentition, e.g., through indirect fabrication techniques or direct fabrication techniques. Examples of indirect and direct fabrication techniques are further described herein with respect to FIGS. 15A, 15B, and 15C. For example, FIG. 1A illustrates a flow diagram for a method 100 of performing a corrective analysis on a digital design of a polymeric aligner, in accordance with one embodiment. One or more operations of method 100 are performed by processing logic of a computing device. The processing logic may include hardware (e.g., circuitry, dedicated logic, programmable logic, microcode, etc.), software (e.g., instructions executed by a processing device), firmware, or a combination thereof. For example, one or more operations of method 100 may be performed by a processing device executing an aligner design analysis module 1450 of FIG. 14. It should be noted that the method 100 may be performed for each unique aligner for each patient's treatment plan, or for each unique aligner at one or more stages (e.g., key stages) of the treatment plan.

At block 102, processing logic may obtain a digital design of an aligner for a dental arch of a patient. The aligner (e.g., a polymeric aligner) in the digital design is shaped to apply forces to one or more teeth of the dental arch. In some embodiments, the processing logic may receive a file including the digital model of the mold used to create the particular aligner. The processing logic may manipulate (e.g., enlarge) the geometry of the digital model of the mold to dynamically generate the digital design of the aligner. In some embodiments, the processing logic may receive the digital design of the aligner from another system or by scanning a manufactured aligner. In some embodiments, the digital design of the aligner is a virtual three-dimensional (3D) model of the aligner that was generated based on a virtual 3D model of the dental arch at a treatment stage.

At block 104, processing logic may perform an analysis on the digital design of the polymeric aligner using at least one of a) a trained machine learning model trained to identify polymeric aligners having probable points of damage, b) a numerical simulation associated with removal of the polymeric aligner from a mold of the dental arch of the patient, c) a numerical simulation associated with progressive damage to the aligner, d) a numerical simulation that simulates loading around weak spots (e.g., interproximal regions) in the aligner, e) a geometry evaluator that evaluates a parameters associated with a geometry of the polymeric aligner, or f) a rules engine comprising one or more rules associated with parameters of polymeric aligners indicative of points of damage. Additional details related to performing the analysis on the digital design of the polymeric aligner using the trained machine learning model are discussed below with reference to FIGS. 2A-2D. Additional details related to performing the analysis on the digital design of the aligner using the numerical simulation associated with removal of the aligner from the mold are discussed below with reference to FIGS. 3A-5B. Additional details related to performing the analysis of the digital design of the aligner using the numerical simulation associated with progressive damage to the aligner are discussed with reference to FIGS. 8A-8C Additional details related to performing the analysis of the digital design of the aligner using the numerical simulation and/or a geometrical evaluator that simulates loading around weak spots of the aligner are discussed with reference to FIGS. 6A-7G. Additional details related to performing the analysis on the digital design of the aligner using the rules engine are discussed below with reference to FIG. 10.

At block 106, processing logic may determine, based on the analysis, whether the digital design of the aligner includes one or more probable points of damage. A probable point of damage may refer to a point having at least a threshold probability that breakage, deformation, or warpage will occur as a result of removing the aligner from the mold, removing the aligner from teeth, use of the aligner, and so forth. At block 107, processing logic determines whether any probable points of damage were identified. If at least one probable point of damage was identified, the method continues to block 108. Otherwise the method may end.

At block 108, processing logic may perform one or more corrective actions and/or select a manufacturing flow based on the one or more probable points of damage. In some embodiments, performing the one or more corrective actions includes modifying the digital design of the aligner to generate a modified digital design of the aligner. In some embodiments, performing the one or more corrective actions includes modifying a digital design of a dental arch associated with a digital design of the aligner. Due to the change in the digital design of the dental arch, the digital design of the aligner may also be changed to accommodate the change in the digital design of the dental arch.

If a probable point of damage is determined to be at or near a outline of the digital design of the aligner, modifying the digital design of the aligner may include modifying the outline radius of the digital design of the aligner. For example, the outline may be lowered to be more straight, as opposed to more pointed (weakens the strength of the aligner at that point), in the digital design of the aligner. Straightening the outline may increase the strength of the aligner at that location and may remove the probable point of damage from the digital design of the aligner. If a probable point of damage is determined to be at or near an interproximal region between two teeth, modifying the digital design of the aligner may include modifying a thickness of a portion of the digital design of the aligner. For example, increasing the thickness of the portion of the digital design of the aligner makes an outer surface of the digital design of the aligner flatter. Thickening the portion of the digital design may strengthen the aligner at the portion and may remove the probable point of damage in the digital design of the aligner. In some embodiments, the thickness of the aligner is controllable for aligners that are directly manufactured using 3D printing techniques but is not controllable for aligners that are manufactured by a thermoforming process.

In some embodiments, modifying the digital design of the aligner may include inserting an indicator in the digital design of the aligner. The indicator represents a recommended place to begin removing the aligner. A location for placing the indicator may be determined during the analysis performed on the digital design. For example, the analysis may identify that applying force at a certain location on the digital design of the aligner to remove the digital design of the aligner is less likely to cause damage than any other location on the digital design of the aligner. Accordingly, the indicator may be placed at that certain location.

In some embodiments, if a probable point of damage is determined to be present at or near a location in the digital design of the aligner that is associated with an attachment (to a tooth, then performing the corrective action may include modifying one or more attachments associated with the probable point of damage on one or more teeth in the virtual 3D model of the dental arch. Modifying the 3D model of the dental arch may cause a modified virtual 3D model of the aligner to be generated based on the changes to the attachments. For example, a cavity of the aligner that accommodates the attachment may be moved, increased or decreased in size, or have a shape changed in the modified virtual 3D model of the aligner based on the change to the attachment in the 3D model of the dental arch.

In some embodiments, if a probable point of damage is determined to be present at or near a location between two teeth, then performing the corrective action may include adding a new virtual filler or enlarging an existing virtual filler to one or more locations on the virtual 3D model of the dental arch associated with the one or more probable points of damage. A virtual filler may refer to a digital feature of or added to a virtual model (such as a virtual model of a dental arch) that presents an additional object between two or more adjacent teeth. In embodiments, the virtual filler of the virtual model changes the geometry of a respective physical mold and reduces the probability of fabrication issues. A modified virtual 3D model of the aligner may be generated based on the modified virtual 3D model of the dental arch including the virtual fillers. The virtual fillers may cause the aligner to have a flatter surface between the two teeth to accommodate the virtual filler. A flatter surface between the teeth may increase the strength of the aligner and remove the probable point of damage from the digital design of the aligner.

After any of the modifications are made to the digital design of the aligner, a modified virtual 3D model of the aligner may be generated based on the modifications to the digital design of the aligner. Processing logic may determine whether the modified digital design of the aligner includes the one or more probable points of damage. Responsive to determining that the modified digital design of the aligner includes one or more probable points of damage, processing logic may perform one or more second corrective actions based on the probable points of damage. This process may be repeated until all of the probable points of damage are removed from the digital design of the aligner, only a threshold number of probable points of damage are still present in the digital design of the aligner, or the like.

In some embodiments, the digital design of the aligner is received during a treatment planning phase of orthodontic treatment. When one or more probable points of damage are determined to be present in the digital design of the aligner, in some embodiments, the corrective action may include recommending modification of one or more attachments on one or more teeth of the patient to reduce a probability that the probable point will fail to below the threshold probability. In some embodiments, the corrective action may include recommending modification of the digital design of the aligner to move one or more teeth using another digital design of another aligner in a different stage of a treatment plan for the patient to reduce the probability that the probable point will fail below the threshold probability. For example, a particular tooth rotation may be specified in a first stage of a treatment plan, and that particular tooth rotation may be achieved using a particular attachment. The treatment plan may be modified to move the particular tooth rotation to a later stage in treatment, thereby causing the use of the particular attachment to also be moved to the later stage in treatment.

In some embodiments, the corrective action may include recommending one or more processes to properly remove the aligner from the dental arch of the patient to reduce the probability that the probable point will fail below the threshold probability. In some embodiments, the corrective action may include notifying a dental practitioner during the treatment planning phase that the digital design of the aligner has a probable point of damage. For example, if the probable point of damage cannot be removed by modifying the digital design of the aligner, then processing logic may notify the dental practitioner of the probable point of damage.

In some embodiments, performing the corrective action based on the one or more probable points of damage may include setting a flag associated with the aligner to indicate that quality inspection should be performed on the aligner after manufacturing. The flag may cause the quality inspection to target the one or more probable points of damage. In some embodiments, the corrective action may include recommending that targeted inspection be performed by sending a notification to a system of an inspector.

In some embodiments, performing the corrective action based on the one or more probable points of damage may include setting a flag to use a breakable mold or mold with weakened regions during manufacturing. A breakable mold may refer to a mold that is broken to remove the aligner from the breakable mold. Less force may be applied to the aligner while the mold is broken, and thus, the probability that the aligner will fail during removal may be reduced.

In some embodiments, performing the corrective action based on the one or more probable points of damage may include changing a geometry of the virtual 3D model of the mold. For example, a portion of the virtual 3D model of the mold may be bubbled out or thickened. A modified virtual 3D model of the aligner may be generated based on the modified virtual 3D model of the mold, and the shape of the modified virtual 3D model may be changed from the original virtual 3D model of the aligner due to the portion of the modified 3D model of the mold. By bubbling out, thickening or expanding the digital model (and thus the aligner) at one or more locations, the amount of force that is needed to remove the aligner from the mold (or dental arch) at that location is reduced. Thus, breakage, warpage, etc. at that location may be mitigated.

In some embodiments, a manufacturing flow may be selected for an aligner at block 108 based on a prediction of a probable point of damage or failure for the aligner or based on a lack of a probable point of damage or failure for the aligner.

Figure 1B:
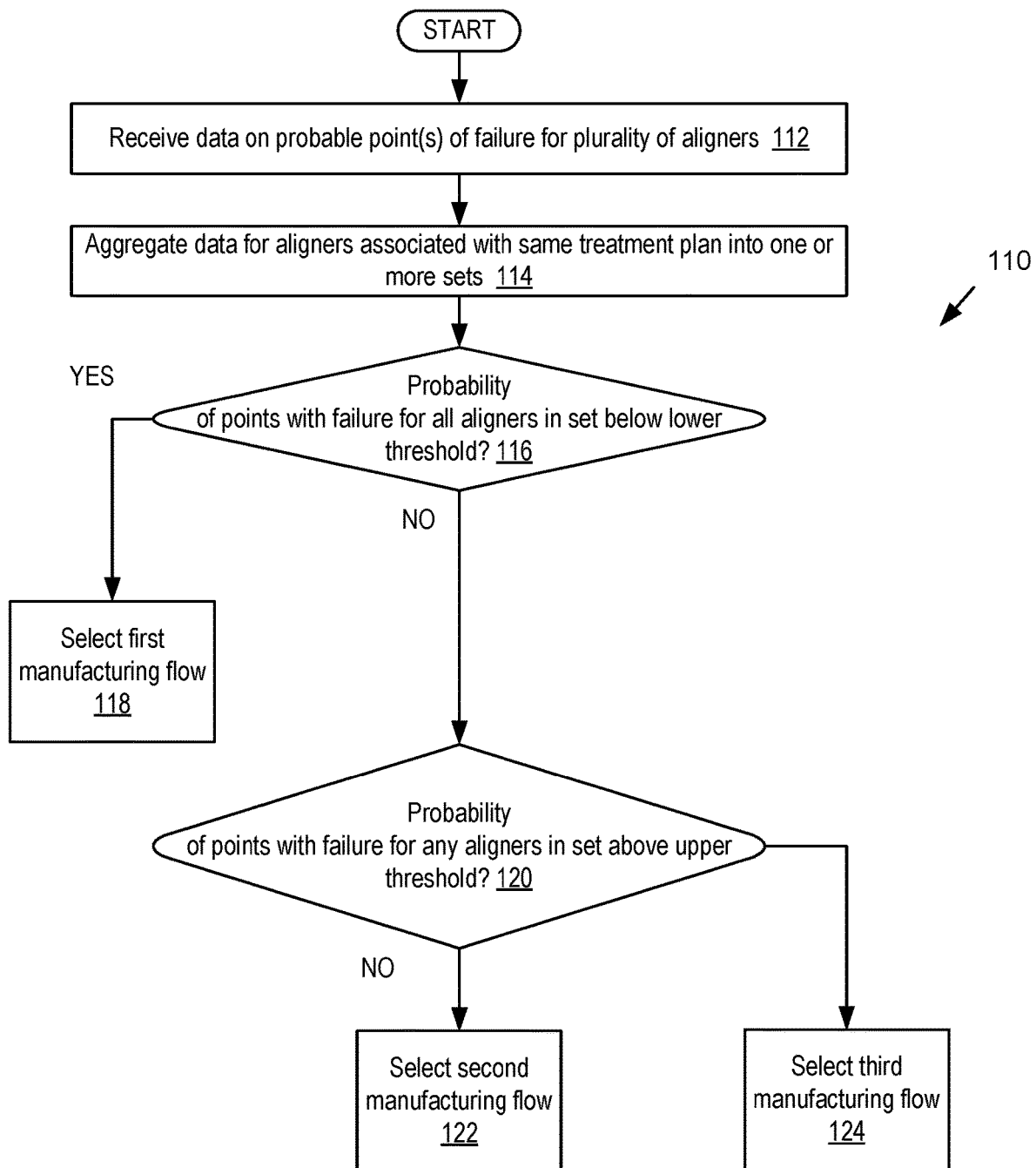
FIG. 1B illustrates a flow diagram of selecting a manufacturing flow for one or more aligners based on damage predictions for the one or more aligners, in accordance with one embodiment.

FIG. 1B illustrates a method 110 of selecting a manufacturing flow for one or more aligners. One or more operations of method 110 are performed by processing logic of a computing device. The processing logic may include hardware (e.g., circuitry, dedicated logic, programmable logic, microcode, etc.), software (e.g., instructions executed by a processing device), firmware, or a combination thereof. For example, one or more operations of method 110 may be performed by a processing device executing an aligner design analysis module 1450 of FIG. 14. It should be noted that the method 110 is described with reference to sets of aligners, such as aligners that are part of a treatment plan for a patient, or aligners that are associated with a treatment plan for a particular dental arch of the patient. However, in embodiments method 110 may be performed for each unique aligner for each patient's treatment plan, or for each unique aligner at key stages of the treatment plan. In embodiments, method 110 may be performed at block 108 of method 100.

At block 112 of method 110, processing logic receives data on probable points of failure for a plurality of aligners. The data may be for aligners associated with one or more orthodontic treatment plans for one or more patients. The data on the probability of points of failure may have been output by a) a trained machine learning model trained to identify aligners having probable points of damage, b) a numerical simulation associated with removal of the aligner from a mold of the dental arch of the patient, c) a numerical simulation associated with progressive damage to the aligner, d) a numerical simulation that simulates loading around weak spots in the aligner, e) a geometry evaluator that evaluates parameters associated with a geometry of the polymeric aligner, or f) a rules engine comprising one or more rules associated with parameters of aligners indicative of points of damage. In some embodiments, data on the probability of points of failure may have been generated by two or more of the aforementioned simulators, rule engines and/or machine learning models.

At block 114, processing logic aggregates the data for the aligners that is associated with the same treatment plan into one or more sets. In one embodiment, the failure probability data for all aligners associated with a treatment plan is aggregated into a single set. Alternatively, the failure probability data for aligners associated with the same treatment plan may be aggregated into two or more sets. For example, the data associated with a lower dental arch of a patient (e.g., data for each treatment stage of the lower dental arch) may be combined into a first data set, and the data associated with an upper dental arch of the patient may be combined into a second data set.

If probabilities of points of aligners being damaged are provided by two or more different techniques (e.g., by a machine learning model and a simulation output, or by two simulation outputs, or by geometry evaluation), then the predictions of the multiple techniques may be combined to improve an accuracy of the prediction. For example, data may be received for a single aligner, where that data includes a first probability of the aligner failing as output by a machine learning model and further includes a second probability of the aligner failing as output by a numerical simulation.

At block 116, each of the one or more data sets is assessed to determine whether all of the aligners in any of the data sets has a probability of damage/failure that is below a lower probability threshold. The lower threshold may have, for example, a value of a 2%, 5%, 10%, 15%, or 20% chance of a point of damage/failure. Aligner sets that have no aligners with points having a probability of damage/failure that meets or exceeds the lower threshold may be identified as particularly low risk aligner sets. Such low risk aligner sets may be fast tracked with minimal manufacturing steps, which may reduce a cost of manufacturing such aligner sets and speed up the manufacture process for such aligner sets. Accordingly, if the probability of points of failure for all aligners in a set are below the lower threshold, the method proceeds to block 118 and a first manufacturing flow is determined for that aligner set. The first manufacturing flow may be, for example, a fast track manufacturing flow. The fast track manufacturing flow may operate under the assumption that no exceptions will be performed, that no aligners in that manufacturing flow will undergo rework, and that the manufacture may be completed with minimal waiting in embodiments. However, if any aligners in an aligner set have any points with a probability of failure/damage that meets or exceeds the lower threshold, the method may continue to block 120.

In some embodiments, processing logic selects from two possible manufacturing flows, and the operations of block 116 are skipped, with the method proceeding from block 114 to block 120.

At block 120, each of the one or more data sets is assessed to determine whether any of the aligners in any of the data sets has a probability of damage/failure that is at or above an upper probability threshold. The upper threshold may have, for example, a value of a 45%, 50%, 55%, 60%, or 65% chance of a point of damage/failure. Aligner sets that have at least one aligner with at least one point having a probability of damage/failure that meets or exceeds the upper threshold may be identified as particularly high risk aligner sets. Such high risk aligner sets may be subject to increased scrutiny, slower manufacturing, added quality control steps, and so on, which may reduce the chance of the aligners in the set becoming damaged and/or increase a chance of detecting any damage in such aligner sets. Accordingly, if no aligners in an aligner set have any points with a probability of damage/failure at or above the upper threshold, the method continues to block 122, and a second manufacturing flow may be selected. If the probability of points of failure for one or more aligners in a set are above the upper threshold, the method proceeds to block 124 and a third manufacturing flow is determined for that aligner set. The second manufacturing flow may be a standard manufacturing flow for aligners. The third manufacturing flow may be a quality control manufacturing flow (e.g., that examines some or all of the aligners in the aligner set using an inspection station for image-based quality control). The third manufacturing flow may be performed by the most experienced technicians or operators in embodiments. In one embodiment, a cycle time for the third manufacturing flow is increased to provide an operator additional time to carefully handle the aligners (e.g., to remove aligners from molds). The first manufacturing work flow at block 118 may be a work flow with a lowest complexity. The second manufacturing work flow at block 122 may be a work flow with an intermediate level of complexity. The third manufacturing work flow at block 124 may be a work flow with a maximum level of complexity.

Figure 2A:
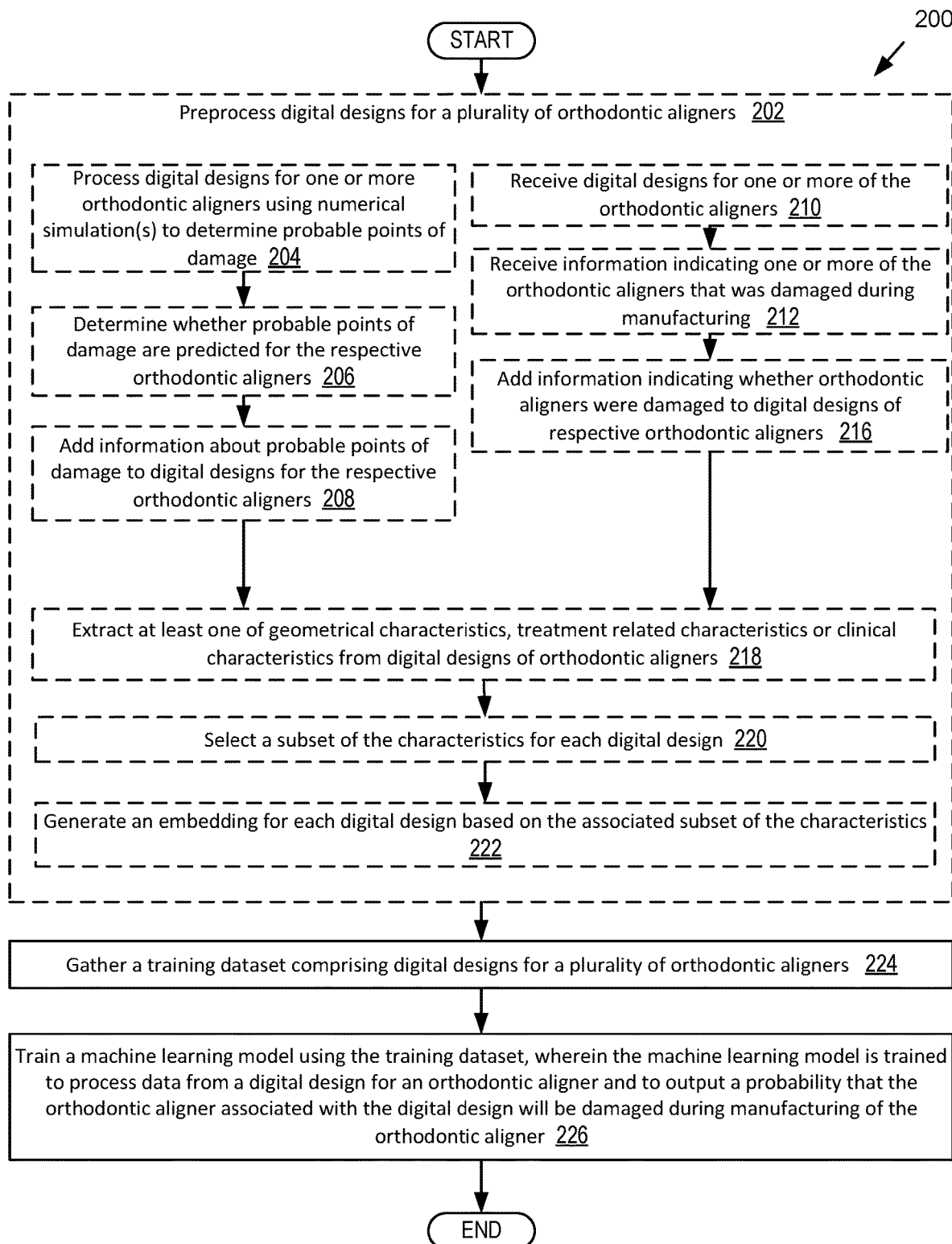
FIG. 2A illustrates a method of training a machine learning model to predict whether an orthodontic aligner will be damaged during manufacture of the orthodontic aligner, in accordance with one embodiment.

FIG. 2A illustrates a flow diagram for a method 200 of training a machine learning model to perform analysis on a digital design of an aligner, in accordance with one embodiment. The machine learning model may be trained to predict whether an orthodontic aligner will be damaged during manufacturing of the orthodontic aligner, in accordance with one embodiment.

One or more operations of method 200 are performed by processing logic of a computing device. The processing logic may include hardware (e.g., circuitry, dedicated logic, programmable logic, microcode, etc.), software (e.g., instructions executed by a processing device), firmware, or a combination thereof. For example, one or more operations of method 200 may be performed by a processing device executing an aligner design analysis module 1450 of FIG. 14.

At block 202 of method 200, processing logic may preprocess digital designs for a plurality of orthodontic aligners so that the digital designs may be used as training data for training a machine learning model. Some digital designs for orthodontic aligners may be associated with orthodontic aligners that have already been manufactured. For such digital designs, a clinical data store may store information indicating whether or not each of the associated respective orthodontic aligners was damaged during manufacturing. Other digital designs for orthodontic aligners may be associated with orthodontic aligners that have not yet been manufactured. Accordingly, there may be no information regarding whether orthodontic aligners associated with such digital designs were damaged during manufacturing.

In one embodiment, blocks 204-208 relate to preparing digital designs of orthodontic aligners that have not been manufactured (or for which damage information does not exist) for use in training a machine learning model. At block 204, processing logic may process digital designs for one or more orthodontic aligners using one or more numerical simulations to determine probable points of damage to the respective orthodontic aligners. Any of the numerical simulations described herein may be used to determine the probable points of failure/damage. Accordingly, probable points of damage for a digital design of an aligner may be determined by processing the digital design of the model using one or more of the methods set forth in FIGS. 3A-8C in embodiments.

As discussed above and further discussed below with reference to FIGS. 3A-5B a numerical simulation may be performed on the digital design of the aligner to simulate one or more forces and/or displacements on the aligner. In some embodiments, the forces simulate removing the aligner from a dental arch-like structure (e.g., teeth or the mold). The numerical simulation can determine when an amount of force required to remove the aligner from a dental arch-like structure reaches a value of stress or strain/stress or deformation energy, or deformation energy level at any point on the aligner that exceeds a threshold value, which may indicate that the particular point will fail. A strain may be determined based on a displacement, motion, or geometry change at the points, and the stress may be determined based on force applied to the aligner. In some embodiments, a strain or stress threshold may be used during the numerical simulation to determine when a point on the digital design of the aligner will likely fail. In this way, the numerical simulation may operate as a predictive model that predicts probable points of damage on the digital design of the aligner. These simulations may be run numerous times on multiple digital designs of aligners and labels may be included with the digital designs indicating whether or not the digital designs include one or more probable points of damage.

At block 206, processing logic may determine, for each of the digital designs, whether probable points of damage are predicted for the associated respective orthodontic aligners. At block 208, processing logic may add information about the probable points of damage to the digital designs for the respective orthodontic aligners. In some instances, this may include adding information about the locations of the probable points of failure and/or the probability of damage/failure for each of the points of probable failure. Additionally, processing logic may add information about the lack of probable points of failure for digital designs for orthodontic aligners that do not have any probable points of failure. In embodiments, probable points of failure may be those points on an orthodontic aligner with a probability of damage that exceeds a probability threshold, such as 50%, 60%, or some other value. The probable points of failure, and lack of probable points of failure, may serve as labels for digital designs of orthodontic aligners. For example, digital designs for which one or more probable points of failure are identified may be assigned a label of 1, indicating a prediction that the associated aligner will be damaged during manufacture. Digital designs for which no probable points of failure are identified may be assigned a label of 0, indicating a prediction that the associated aligner will not be damaged during manufacture.

In one embodiment, blocks 210-216 relate to preparing digital designs of orthodontic aligners that have been manufactured, and for which damage information exists, for use in training a machine learning model. At block 210, processing logic may receive digital designs for one or more orthodontic aligners. At block 212, processing logic may receive information indicating one or more of the orthodontic aligners that were damaged during manufacturing. Additionally, processing logic may receive information indicating one or more locations at which damage occurred in manufactured aligners and/or types of damage that occurred (e.g., warping, cracking, deformation, etc.). Actual points of damage for aligners may be reported by manufacturing technicians, by an automated manufacturing system and/or by patients in some embodiments.

The information pertaining to whether the aligners experienced points of damage may also be obtained from historical patient feedback. For example, patients may provide a report that specifies the aligner failed and/or the location of the damage may be determined (e.g., from the report, from scanning the aligner, etc.). Also, the patient may specify which aligner (e.g., top or bottom) at a particular stage of the treatment plan failed. In some instances, the patient may return the broken aligner to a site and the broken aligner may be scanned at the site to obtain an image of the digital design of the polymeric aligner including the location of the point of damage. As such, images of the broken aligners may be collected for image corpora (a set of image corpus, which may include a large set of images) and used as part of the training data. Information provided by the patient about the broken aligner or determined via scanned images may be correlated to determine the ID of the aligner, which can then be used to obtain the digital design of that particular aligner. The location of the point of damage may be placed in the digital design of the aligner with a label indicating there is a point of damage at that location.

At block 216, processing logic may add information about whether damage occurred (e.g., about points of damage) to the digital designs for the respective orthodontic aligners. In some instances, this may include adding information about the locations of detected points of failure/damage. Additionally, processing logic may add information about the lack of damage for digital designs for orthodontic aligners that were not damaged during manufacturing. The probable points of damage, and lack of points of damage, may serve as labels for digital designs of orthodontic aligners. For example, digital designs for which damage occurred may be assigned a label of 1, indicating that the associated aligner was damaged during manufacture. Digital designs for which no damage occurred may be assigned a label of 0, indicating that the associated aligner was not damaged during manufacture. Accordingly, actual points of damage on physical aligners may be added as labels or metadata to the associated digital designs of the aligners. In some instances, digital aligners are labeled with information indicating whether or not the associated physical aligners had one or more damaged points, but the actual locations of the damaged points are not indicated.

At block 218, processing logic may extract at least one of geometrical characteristics, treatment related characteristics or clinical characteristics from the digital designs of the orthodontic aligners. In one embodiment, the characteristics are extracted by a software module that analyzes three dimensional virtual models of dental arches and/or aligners, and that determines characteristics of the associated dental arches and/or aligners based on the analysis. The extracted characteristics may include many different characteristics, including characteristics that have no bearing on whether an aligner will become damaged as well as characteristics that may have some effect on whether an aligner will become damaged. Examples of geometrical characteristics include individual tooth shape for one or more teeth, location of teeth on a dental arch in relation to other teeth, jaw shape, and so on. Examples of treatment related characteristics include number of stages of treatment, number and positions of attachments to teeth, whether aligners are active or passive aligners, and so on. Examples of clinical characteristics include amount of tooth crowding, deep bite, level of malocclusion, and so on. In embodiments, the characteristics that are extracted by processing logic may be formatted as structured or tabular data. Accordingly, characteristics about the aligner associated with a digital design may be represented as structured or tabular data.

At block 220, a subset of the characteristics for each digital design may be selected. In one embodiment, the same characteristics are included the subsets for each of the digital designs. The subset of selected characteristics may be those characteristics that correlate to damage or manufacturing defects in aligners.

Table 1 below identifies numerous characteristics that may be extracted from a digital model of a dental arch or a digital model of an aligner, in accordance one embodiment. Table 1 further indicates, for one embodiment, whether each characteristic was included in the subset at block 220. Table 1 shows just a small sample of the many different types of characteristics that may be extracted from a digital model of a dental arch and/or a digital model of an aligner. While a majority of those characteristics that are shown are included in the subset, in some embodiments less than half (e.g., just a small fraction) of the total number of extracted characteristics may be included in the subset.

| Characteristics | Description of characteristics | In subset? |
| --- | --- | --- |
| Active aligner count | Number of active aligners (integer) | Yes |
| Left molar shift | Left molar's shift from ideal Class1 position divided by distance between ideal BiteClass2 and ideal BiteClass1 (%) | Yes |
| Left canine shift | Left canine's shift from ideal Class1 position divided by distance between ideal BiteClass2 and ideal BiteClass1 (%) | No |

| Characteristics | Description of characteristics | In subset? |
| --- | --- | --- |
| Right molar shift | Right molar's shift from ideal Class1 position divided by distance between ideal BiteClass2 and ideal BiteClass1 (%) | Yes |
| Right canine shift | Right canine's shift from ideal Class1 position divided by distance between ideal BiteClass2 and ideal BiteClass1 (%) | No |
| Canine average tooth width | Average width of canine teeth (mm) | Yes |
| Canine average tooth height | Average height of canine teeth (mm) | Yes |
| Canine ridge count | Total number of ridges on canines (integer) | No |
| Canine depth delta | Delta between initial depth and planned depth for a canine (mm) | Yes |
| Canine maximum angulation | Maximum tooth angulation of canines in one or more axes (degrees) | Yes |
| Canine maximum inclination | Maximum tooth inclination of canines (degrees) | Yes |
| Incisor attachment count | Total number of attachments on incisors (integer) | Yes |
| Incisor average crown height | Average height of crown height of incisors (mm) | Yes |
| Incisor maximum angulation | Maximum tooth angulation of incisors in one or more axes (degrees) | Yes |
| Incisor maximum inclination | Maximum tooth inclination of incisors (degrees) | Yes |
| Canine maximum prominence | Absolute distance between tooth front point and jaw arch along jaw occlusal plane for canines (mm) | Yes |
| Incisor maximum prominence | Absolute distance between tooth front point and jaw arch along jaw occlusal plane for incisors (mm) | Yes |
| Molar attachment count | Total number of attachments on molars (integer) | Yes |
| Molar average crown height | Average height of crown height of molars (mm) | Yes |
| Molar maximum prominence | Absolute distance between tooth front point and jaw arch along jaw occlusal plane for molars (mm) | Yes |
| Passive aligner count | Number of passive aligners (integer) | Yes |
| Final premolar crowding | Final premolar crowding minus sum of collision depths for all teeth pairs between first premolars of given jaw | Yes |
| Initial premolar crowding | Initial premolar crowding minus sum of collision depths for all teeth pairs between first premolars of given jaw | Yes |
| Premolar attachment count | Total number of attachments on premolars (integer) | Yes |
| Premolar avg. crown height | Average height of crown height of premolars (mm) | Yes |
| Premolar max angulation | Maximum tooth angulation of premolars in one or more axes (degrees) | Yes |
| Incisor max inclination | Maximum tooth inclination of premolars (degrees) | Yes |
| Intermolar distance | Distance between leftmost and rightmost back molars (mm) | Yes |
| Spee curve for molars | Spee curve depth for molars | Yes |

One possible extracted characteristic is the Spee curve (also referred to the curve of Spee), which is the curvature of the mandibular occlusal plane beginning at the premolar and following the buccal cusps of the posterior teeth, continuing to the terminal molar. In other words, the Spee curve is an anatomic curvature of the occlusal alignment of the teeth, beginning at the tip of the lower incisor, following the buccal cusps of the natural premolars and molars, and continuing to the anterior border of the ramus. The idea behind measuring this curvature is to find a circle in the sagittal plane in 2D space or to find a sphere in 3D space that best fits a set of tip points of the lower jaw. The radius and the angle between the segments connecting the center of this circle with the tip point of the terminal molar and the first incisor may be measures of curvature. It may be assumed that the larger the radius of the circle and the smaller the angle, the less pronounced the curvature of the jaw.

For finding the Spee curve in 2D space, the curvature may be measured separately for each side of the jaw arch. Each tip point may be projected onto a jaw midline plane (e.g., where the x coordinate equals zero). The problem of finding the center and the radius of the circle that best fits all the points may be solved as follows:
1) Compute an initial guess by averaging the x and y coordinates for all points;
2) Improve on the initial guess, such as by using a least squares estimator (e.g., based on the Euclidean distance between the points and the circle); and
3) Given computed residuals and a cost function, use least squares to final a local minimum of the cost function (e.g., using the Levenberg-Marquardt method) and return the circle's radius and coordinates of the center of the circle.

Processing logic may then find an angle between the segments connecting the center of the circle with the tip point of the terminal molar and the first incisor.

At block 222, processing logic may generate an embedding for each digital design for an orthodontic aligner based on the subset of the characteristics determined for that digital design. The embedding may have a structured or tabular data format in some embodiments.

In an alternative embodiment, the operations of block 218 and 220 may not be performed. Instead, one or more height maps may be generated from the digital design for the aligners (e.g., from the 3D digital model of the dental arch or of the aligner). The height maps may be generated by projecting the 3D digital model onto multiple different planes from multiple different perspectives. In such an embodiment, at block 222 the embeddings may be generated by combining the multiple height maps associated with a digital design for an aligner.

At block 224, processing logic gathers a training dataset comprising digital designs of a plurality of orthodontic aligners. The training dataset may include the embeddings generated at block 222 in an embodiment. Each embedding may be associated with metadata indicating whether the aligner associated with the embedding is labeled as a damaged aligner or as an undamaged aligner. The training dataset preferably contains thousands, tens of thousands, hundreds of thousands or more data points, where each data point is data (e.g., an embedding) associated with a different aligner. Digital designs of aligners with associated points of damage (as provided by real world data) and digital designs of aligners with associated probable points of damage (as provided by an output of a numerical simulation) may be used together to generate a robust machine learning model that can predict probable points of damage of new aligners from digital models of those aligners in some embodiments. The machine learning model or statistical model may also classify types of damage, degree of damage, and/or other information related to aligners in embodiments.

At block 226, processing logic trains a machine learning model using the training dataset. The machine learning model may be trained to process data (e.g., an embedding) from a digital design for an orthodontic aligner and to output a probability that the orthodontic aligner associated with the digital design will be damaged during manufacturing of the orthodontic aligner, will be damaged during clinical usage of the orthodontic aligner, will be damaged during shipping and handling of the orthodontic aligner, etc. In embodiments, the machine learning model is trained to have a rate of false positives to a desired target, for example 2% or less.

A machine learning model may refer to a model artifact that is created by a training engine using a training dataset (e.g., training input and corresponding target outputs or labels). Training may be performed using a set of training data including at least one of a) digital designs of a first set of aligners with labels indicating whether or not each of the first plurality of aligners experienced one or more points of damage or b) digital designs of a second set of aligners with labels indicating whether or not each of the second set of aligners include one or more probable points of damage. The machine learning model may be composed of a single level of linear or non-linear operations (e.g., a support vector machine (SVM) or a single level neural network) or may be a deep neural network that is composed of multiple levels of non-linear operations. Examples of deep networks and neural networks include convolutional neural networks and/or recurrent neural networks with one or more hidden layers. Some neural networks may be composed of interconnected nodes, where each node receives input from a previous node, performs one or more operations, and sends the resultant output to one or more other connected nodes for further processing.

Convolutional neural networks include architectures that may provide efficient image recognition. Convolutional neural networks may include several convolutional layers and subsampling layers that apply filters to portions of the image of the text to detect certain features (e.g., points of damage). That is, a convolutional neural network includes a convolution operation, which multiplies each image fragment by filters (e.g., matrices) element-by-element and sums the results in a similar position in an output image.

Recurrent neural networks may propagate data forwards, and also backwards, from later processing stages to earlier processing stages. Recurrent neural networks include functionality to process information sequences and store information about previous computations in the context of a hidden layer. As such, recurrent neural networks may have a "memory".

In some embodiments, the machine learning model may be a random forest classifier. A random forest classifier applies an ensemble learning method for classification by constructing multiple decision trees (e.g., hundreds to thousands of decision trees) during training that output classification decisions based on input data. A random forest classifier averages the decisions of multiple decision trees, and produces outputs based on the average. Different decision trees in the random forest classifier may be trained on different parts of the training dataset in embodiments. Each decision tree may be a predictive model that uses observations about input data (represented in branches of the decision tree) to reach a conclusion about the input data (represented in leaves of the decision tree). For example, each decision tree may be trained to determine a classification for a digital design for an aligner. In embodiments, the random forest classifier may be trained using a training algorithm such as feature bagging (also referred to as bootstrap aggregating) that selects, at each candidate split in the learning process, a random subset of features. An advantage of a trained random forest classifier is that after a classification is made, processing logic or a user can determine exactly why the classification was made by following the branches of the one or more decision trees that reached the classification decision.

In some embodiments, the machine learning model may be an XGBoost classifier. An XGBoost classifier is an implementation of a gradient boosted decision tree. In other embodiments, other gradient boosted decision trees may be used to implement the machine learning model. Boosting is an ensemble technique where new models are added to correct the errors made by existing models. Models are added sequentially until no further improvements can be made. Gradient boosting is an approach where new models are created that predict the residuals or errors of prior models, Results of multiple models are then added together to make a final prediction. It is called gradient boosting because it uses a gradient descent algorithm to minimize the loss when adding new models. In some embodiments, the machine leaning model may be a logistic regression model.

In embodiments in which a random forest classifier or gradient boosted decision tree classifier (e.g., XGBoost classifier) are trained on characteristics extracted from digital models of dental arches or aligners, the machine learning model may be trained to express the joint effect of the characteristics and identify aligners that are likely to be damaged or broken.

In some embodiments, the machine learning model may be periodically retrained using updated training datasets. For example, additional data on manufactured aligners may be continuously generated as new patients are treated. On some periodic or regular basis (e.g., every six months), processing logic may repeat the training of the machine learning model. By regularly retraining the machine learning model, new information, techniques and/or processes may be captured and reflected in the machine learning model, such as updated software, updated manufacturing flows, and so on. In some embodiments, training of the machine learning model may be ongoing or continuous based on a continuous inflow of new data. In some embodiments, different machine learning models are trained for aligners that are formed from different materials, for aligners that are manufactured using different manufacturing flows, and/or for aligners that have other parameters (e.g., direct fabrication vs. thermoforming). For example, a first machine learning model may be trained to predict probable points of damage on an aligner that is manufactured by thermoforming it over a mold, and a second machine learning model may be trained to predict probably point of damage on an aligner that is directly fabricated using 3D printing or other rapid prototyping techniques.

Figure 2B:
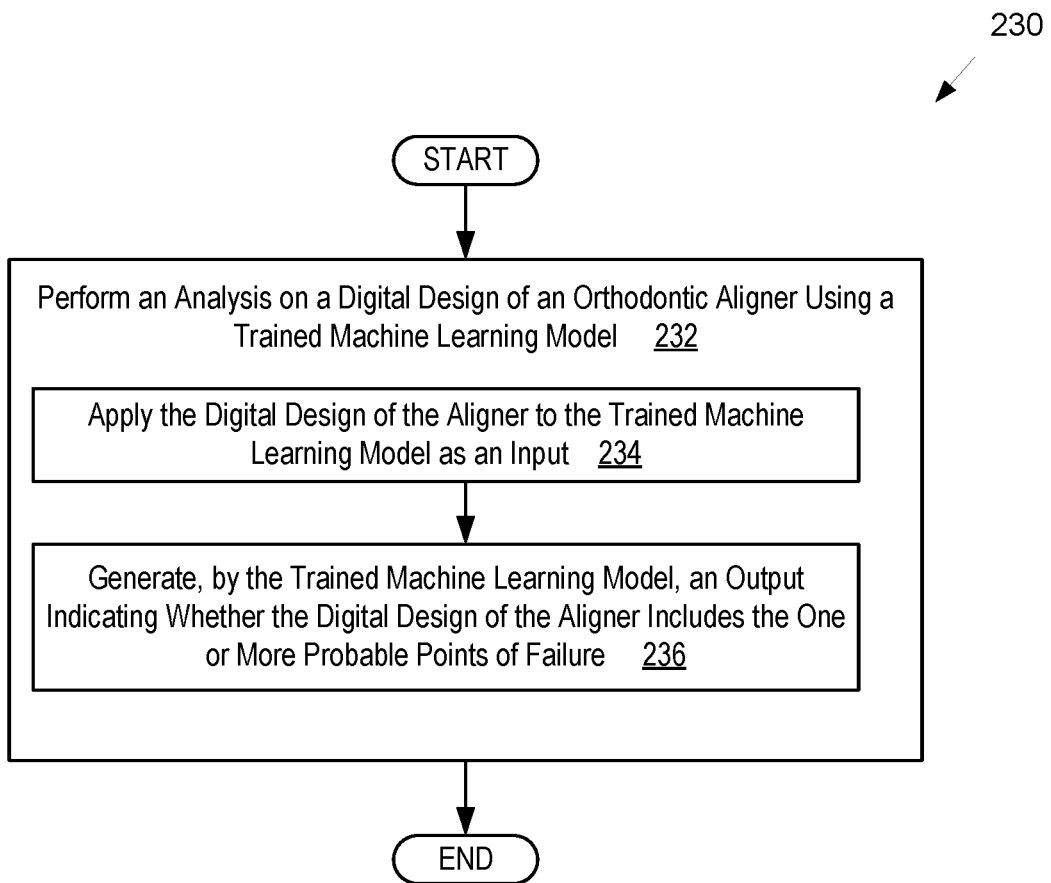
FIG. 2B illustrates a flow diagram for a method of performing analysis on a digital design of an orthodontic aligner using a trained machine learning model, in accordance with one embodiment.

FIG. 2B illustrates a flow diagram for a method 230 of performing analysis on a digital design of an aligner using a trained machine learning model, in accordance with one embodiment. One or more operations of method 230 are performed by processing logic of a computing device. The processing logic may include hardware (e.g., circuitry, dedicated logic, programmable logic, microcode, etc.), software (e.g., instructions executed by a processing device), firmware, or a combination thereof. For example, one or more operations of method 230 may be performed by a processing device executing an aligner design analysis module 1450 of FIG. 14. It should be noted that the method 230 may be performed for each unique aligner for each patient's treatment plan, or for each unique aligner at key stages of the treatment plan. Further, method 230 includes operations that may be performed during block 104 of FIG. 1A.

At block 232 of method 230, processing logic may perform an analysis on a digital design of an orthodontic aligner (e.g., a polymeric orthodontic aligner) using a trained machine learning model, which may have been trained in accordance with method 200. Performing the analysis on the digital design of the aligner using the trained machine learning model may include applying (block 234) the digital design of the aligner to the trained machine learning model as an input. Further, performing the analysis on the digital design of the aligner using the trained machine learning model may include generating (block 236), by the trained machine learning model, an output indicating whether the digital design of the aligner includes the one or more probable points of damage. If the digital design of the aligner includes the one or more probable points of damage, the output of the trained machine learning model may identify the locations of the one or more points of damage in some embodiments. The output of the trained machine learning model may additionally include recommendations of one or more of the corrective actions described above. Alternatively, the output of the trained machine learning model may be input into a further system or module (e.g., another trained machine learning model) along with the digital design of the aligner. The further system or module may then determine a recommended corrective action based on the digital design of the aligner and the predicted point(s) of damage.

After the trained machine learning model determines that one or more points of probable damage are predicted, the digital design of the aligner that includes the one or more probable points of damage may be further processed by performing a numerical simulation on the digital design of the polymeric aligner to verify whether the one or more probable points of damage are present in some embodiments. The numerical simulation may be any of the numerical simulations described herein. For example, the numerical simulation may a) simulate removal of the orthodontic aligner from a mold of a dental arch of a patient or b) simulate loading around weak spots in the orthodontic aligner in embodiments. Processing the digital model of the aligner using the numerical simulation may be computationally expensive and require much greater resources than processing the digital model of the aligner using the trained machine learning model. Accordingly, by first processing the digital model of the aligner using the trained machine learning model, and then limiting the use of the numerical simulation to testing digital models of aligners for which the trained machine learning model predicted a point of damage, resource utilization (e.g., memory and/or processor utilization) may be minimized. Additionally, in some embodiments the trained machine learning model determines the presence of one or more probable points of damage, but does not identify the location of such probable points of damage. By processing digital models of aligners for which the trained machine learning model has predicted a point of damage using the numerical simulation, the locations of the one or more points of damage may be identified, and corrective actions may be determined in some embodiments.

Figure 2C:
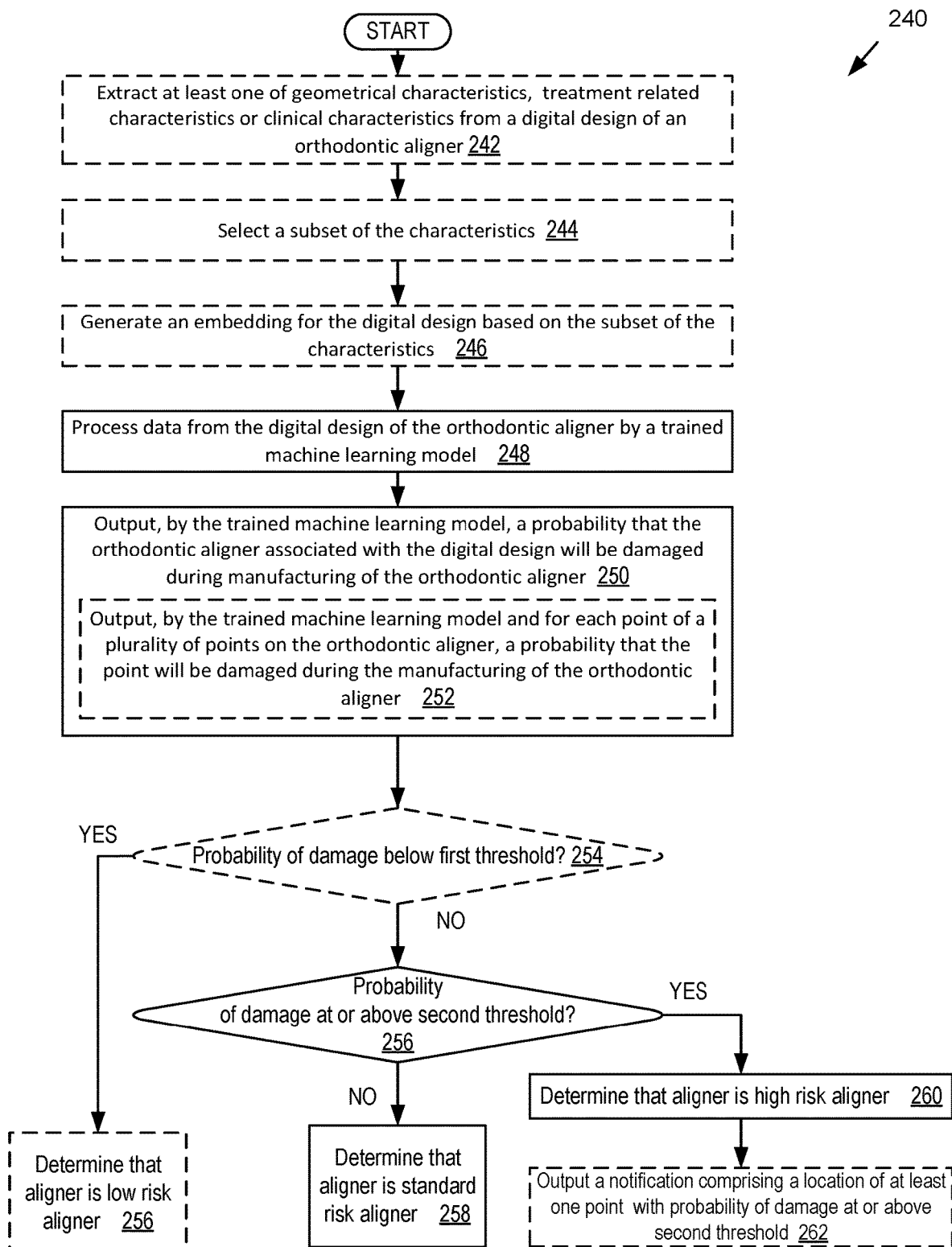
FIG. 2C illustrates a flow diagram for a method of determining whether an orthodontic aligner will become damaged (e.g., break) during or after manufacturing of the orthodontic aligner using a trained machine learning model, in accordance with one embodiment.

FIG. 2C illustrates a flow diagram for a method 240 of determining whether an orthodontic aligner will become damaged (e.g., break) during or after manufacturing of the orthodontic aligner using a trained machine learning model, in accordance with one embodiment. Examples of post-manufacturing damage include damage during clinical use of the aligner, damage during shipping and handling of the aligner, and so on. The machine learning model may have been trained according to method 200. One or more operations of method 240 are performed by processing logic of a computing device. The processing logic may include hardware (e.g., circuitry, dedicated logic, programmable logic, microcode, etc.), software (e.g., instructions executed by a processing device), firmware, or a combination thereof. For example, one or more operations of method 240 may be performed by a processing device executing an aligner design analysis module 1450 of FIG. 14. It should be noted that the method 240 may be performed for each unique aligner for each patient's treatment plan, or for each unique aligner at key stages of the treatment plan. Further, method 230 includes operations that may be performed during block 104 of FIG. 1A.

At block 242 of method 240, processing logic may extract geometrical characteristics, treatment related characteristics and/or clinical characteristics from a digital design of an orthodontic aligner in the manner set forth above with reference to method 200. At block 244, processing logic may select a subset of the characteristics. The subset of characteristics that are selected may correspond to a same subset of characteristics that were used to train the machine learning model. At block 246, processing logic may generate an embedding for the digital design based on the subset of the characteristics.

At block 248, processing logic processes data from the digital design of the orthodontic aligner using the trained machine learning model. The data from the digital design may include the embedding generated at block 246 in an embodiment. Alternatively, or additionally, the data from the digital design may include a three dimensional digital model of the aligner or a three dimensional digital model of a dental arch or mold to be used to manufacture the aligner. Alternatively, or additionally, the data from the digital design may include one or more height maps that are generated by projecting the three dimensional digital model of the dental arch or the aligner onto one or more planes.

At block 250, the trained machine learning model outputs a probability that the orthodontic aligner associated with the digital model will be damaged during manufacturing of the aligner or during later use of the aligner. The probability may be a value ranging from 0 to 1, where 1 may represent a 100% chance that the aligner will be damaged and a 0 represents a 0% chance that the aligner will be damaged.

In one embodiment, at block 252 the machine learning model further outputs information identifying the probability that specific points or locations of the orthodontic aligner will be damaged. For example, a separate probability value from 0 to 1 may be output for each of a plurality of points on the orthodontic aligner.

In one embodiment, at block 254 processing logic determines whether the probability of the orthodontic aligner being damaged is below a first threshold (or whether the probability of all points on the orthodontic aligner being damaged are below the first threshold). If the probability of the orthodontic aligner being damaged is below the first threshold, the method continues to block 256, and a determination may be made that the aligner is a low risk aligner. As in FIG. 1B, a first manufacturing flow for low risk aligners may then be selected for the aligner.

If at block 254 a determination is made that the probability of the orthodontic aligner is above the first threshold, the method continues to block 256. At block 256, processing logic determines whether the probability of the orthodontic aligner being damaged is above a second threshold (or whether the probability of any points on the orthodontic aligner being damaged are above the second threshold). The second threshold may be above the first threshold. For example, the first threshold may be 0.2%, 0.5%, 1%, 2%, 5%, of 10%, and the second threshold may be 15%, 20%, 25%, 30%, 40%, or 50%. If the probability of the orthodontic aligner being damaged is above the second threshold, the method continues to block 260. Otherwise, the method continues to block 258.

At block 258, a determination may be made that the aligner is a standard risk aligner. As in FIG. 1B, a second manufacturing flow for standard risk aligners may then be selected for the aligner.

At block 260, processing logic determines that the aligner is a high risk aligner. As in FIG. 1B, a third manufacturing flow for high risk aligners may then be selected for the aligner. In one embodiment, at block 262 processing logic may output a notification comprising a location of at least one point with a probability of damage at or above the second threshold. Such a notification may be output, for example, if the machine learning model output data indicating locations of points on the aligner and associated probabilities of those points becoming damaged.

In some embodiments, as shown in FIG. 2C, three different classifications may be determined for an aligner based on the probability that the aligner will be damaged during manufacturing or after manufacturing. These may include a low risk classification, a medium or standard risk classification, and a high risk classification. In other embodiments, aligners may be classified into a binary classification, including standard risk (or no damage predicted) and high risk (or damage predicted). In such embodiments, the operations of blocks 254 and 256 may be omitted.

Figure 2D:
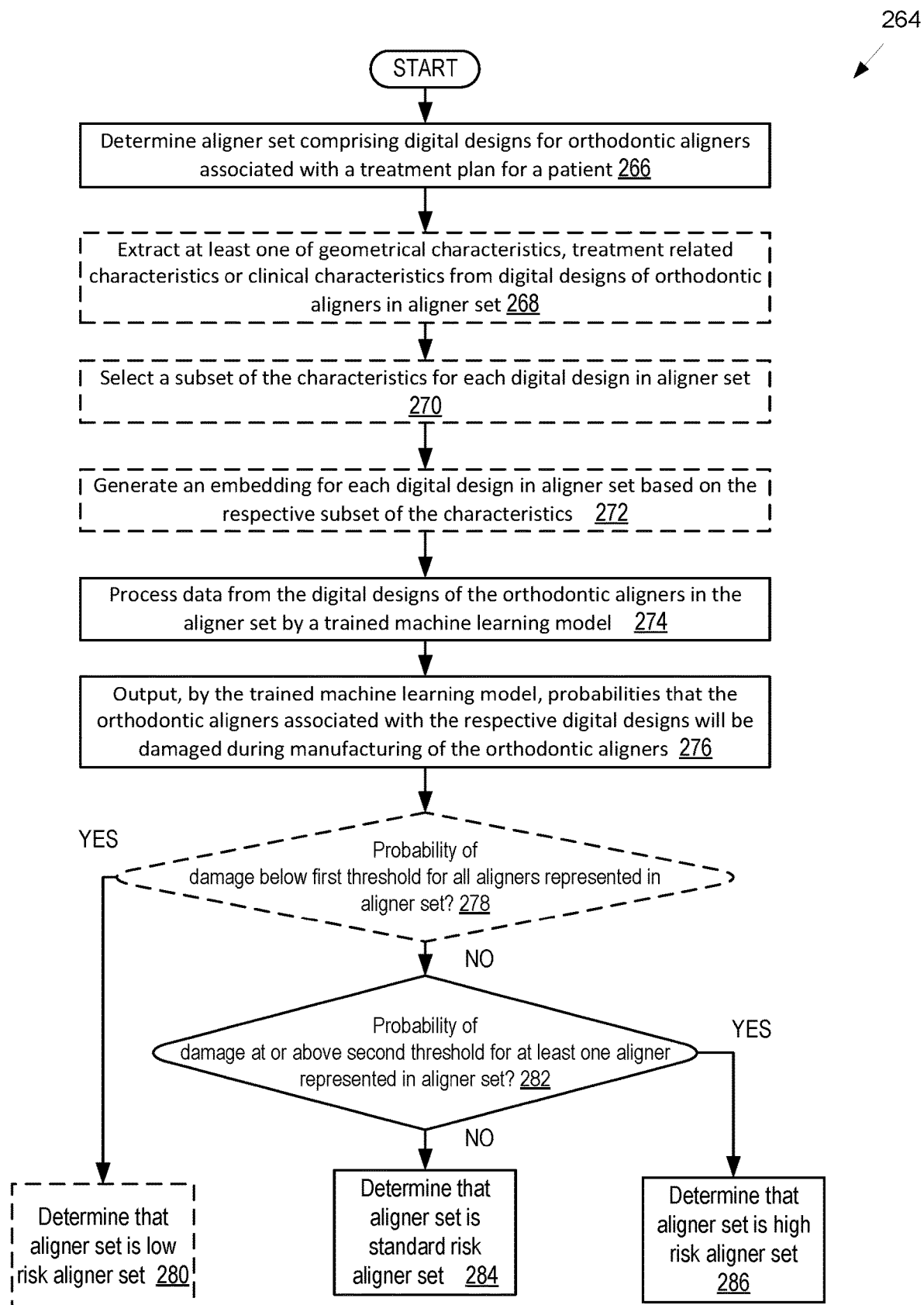
FIG. 2D illustrates a flow diagram for a method of determining whether any orthodontic aligner in a set of orthodontic aligners associated with a treatment plan for a patient will become damaged (e.g., break) using a trained machine learning model, in accordance with one embodiment.

FIG. 2D illustrates a flow diagram for a method 264 of determining whether any orthodontic aligner in a set of orthodontic aligners associated with a treatment plan for a patient will become damaged (e.g., break) during or after manufacturing of the set of orthodontic aligners using a trained machine learning model, in accordance with one embodiment. The machine learning model may have been trained according to method 200. One or more operations of method 264 are performed by processing logic of a computing device. The processing logic may include hardware (e.g., circuitry, dedicated logic, programmable logic, microcode, etc.), software (e.g., instructions executed by a processing device), firmware, or a combination thereof. For example, one or more operations of method 264 may be performed by a processing device executing an aligner design analysis module 1450 of FIG. 14. It should be noted that the method 264 may be performed for each treatment plan, or for the upper dental arch and lower dental arch of each treatment plan.

At block 266 of method 264, processing logic determines an aligner set comprising digital designs for orthodontic aligners associated with a treatment plan for a patient. For example, a treatment plan may divide orthodontic treatment of a patient into a sequence of stages, and a different orthodontic aligner may be designed for each stage of treatment. A single treatment plan may include any number of stages and associated digital designs for orthodontic aligners (e.g., up to 50 stages), and separate digital designs may be generated for the upper and lower dental arches for each stage. In one embodiment, the aligner set includes all of the digital designs for either the upper dental arch or the lower dental arch associated with a treatment plan for a patient. In one embodiment, the aligner set includes all digital designs of both the upper dental arch and the lower dental arch associated with the treatment plan for a patient.

At block 268, processing logic may extract geometrical characteristics, treatment related characteristics and/or clinical characteristics from the digital design of each orthodontic aligner in the aligner set in the manner set forth above with reference to method 200. At block 270, processing logic may select a subset of the characteristics. The subset of characteristics that are selected may correspond to a same subset of characteristics that were used to train the machine learning model. At block 272, processing logic may generate an embedding for each digital design in the aligner set based on the respective subset of the characteristics.

At block 274, processing logic processes data from the digital designs of the orthodontic aligners using the trained machine learning model. The data from the digital designs may include the embeddings generated at block 246 in an embodiment. Alternatively, or additionally, the data from the digital designs may include three dimensional digital models of the aligners or three dimensional digital models of a dental arch or mold to be used to manufacture the aligners. Alternatively, or additionally, the data from the digital designs may include one or more height maps that are generated by projecting the three dimensional digital models of the dental arch or the aligner onto one or more planes.

At block 276, the trained machine learning model outputs, for each digital design of an aligner in the aligner set, a probability that the aligner associated with the respective digital model will be damaged (e.g., during manufacturing of the aligner or during later use of the aligner). The probability may be a value ranging from 0 to 1, where 1 may represent a 100% chance that the aligner will be damaged and a 0 represents a 0% chance that the aligner will be damaged.

In one embodiment, at block 278 processing logic determines whether the probability of any orthodontic aligner being damaged is below a first threshold (or whether the probability of being damaged for all points on the orthodontic aligners are below the first threshold). If the probability of being damaged is below the first threshold for all the orthodontic aligners, the method continues to block 280, and a determination may be made that the aligner set is a low risk aligner set. As in FIG. 1B, a first manufacturing flow for a low risk aligner set may then be selected for the aligner set.

If at block 278 a determination is made that the probability of one or more orthodontic aligner being damaged is above the first threshold, the method continues to block 282. At block 282, processing logic determines whether the probability of at least one orthodontic aligner being damaged is at or above a second probability threshold (or whether the probability of any points on at least one orthodontic aligner being damaged are at or above the second threshold). The second threshold may be above the first threshold. For example, the first threshold may be 0.2%, 0.5%, 1%, 2%, 5%, of 10%, and the second threshold may be 15%, 20%, 25%, 30%, 40%, or 50%. If the probability of any orthodontic aligner in the aligner set being damaged is at or above the second threshold, the method continues to block 286. Otherwise, the method continues to block 284.

At block 284, a determination may be made that the aligner set is a standard risk aligner set. As in FIG. 1B, a second manufacturing flow for standard risk aligner sets may then be selected for the aligner set.

At block 286, processing logic determines that the aligner set is a high risk aligner set. As in FIG. 1B, a third manufacturing flow for high risk aligner sets may then be selected for the aligner set.

In some embodiments, as shown in FIG. 2D, three different classifications may be determined for an aligner set based on the probability that aligners in the aligner set will be damaged during manufacturing or after manufacturing. These may include a low risk classification, a medium or standard risk classification, and a high risk classification. In other embodiments, aligner sets may be classified into a binary classification, including standard risk (or no damage predicted) and high risk (or damage predicted). In such embodiments, the operations of blocks 254 and 256 may be omitted.

Figure 3A:
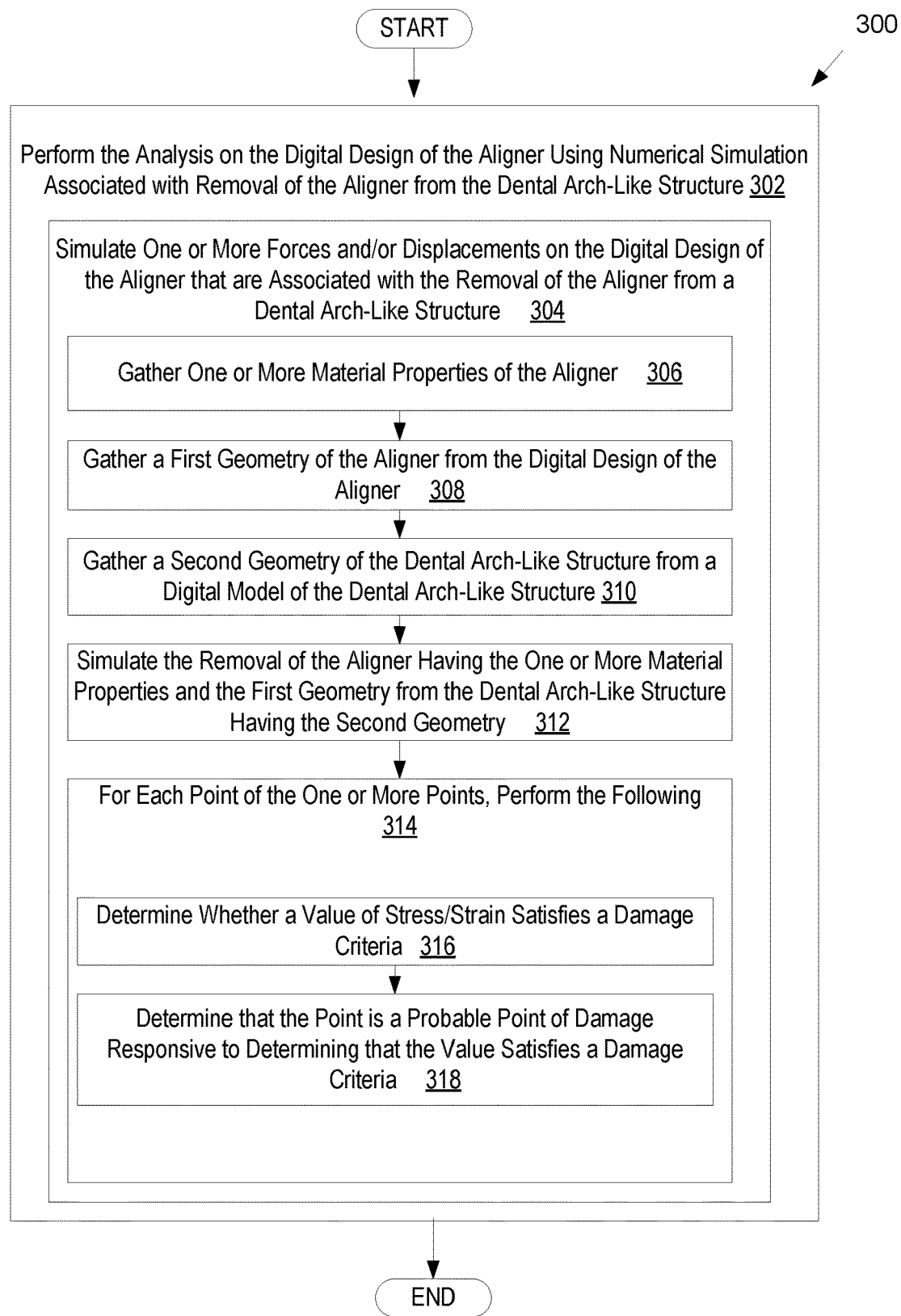
FIG. 3A illustrates a flow diagram for a method of performing analysis on a digital design of a polymeric aligner using numerical simulation, in accordance with one embodiment.

FIG. 3A illustrates a flow diagram for a method 300 of performing analysis on a digital design of an aligner (e.g., a polymeric aligner) using numerical simulation, in accordance with one embodiment. One or more operations of method 300 are performed by processing logic of a computing device. The processing logic may include hardware (e.g., circuitry, dedicated logic, programmable logic, microcode, etc.), software (e.g., instructions executed by a processing device), firmware, or a combination thereof. For example, one or more operations of method 300 may be performed by a processing device executing an aligner design analysis module 1450 of FIG. 14. It should be noted that the method 300 may be performed for each unique aligner for each patient's treatment plan, or for each unique aligner at key stages of the treatment plan. Further, method 300 includes operations that may be performed during block 104 of FIG. 1A.

At block 302, processing logic may perform the analysis on the digital design of the aligner using numerical simulation associated with removal of the polymeric aligner from tooth-like or dental arch-like structures (such as the mold or patient dentition). The numerical simulation may include finite element method, finite difference method, finite volume method, meshfree methods, smoothed-particle methods, combinations of these methods, or the like. Finite element method (also referred to as finite element analysis) may refer to a numerical method for solving partial differential equations, which can also be applied to perform structural analyses of aligners. The geometry of structure (in this case aligner) is discretized to a number of points or elements over a domain to solve a set of partial differential equations characterizing the constitutive relations of the aligner material, and solutions are explored in the finite dimensional functional space. Finite difference method may refer to a numerical method for solving differential equations by approximating them with difference equations and calculating approximate values at discrete points. Finite volume method may refer to a method for representing and evaluating partial differential equations in the form of algebraic equations. Finite volume method may also calculate values (e.g., strain, stress, force) at discrete places on a meshed geometry of the digital design of the aligner. "Finite volume" may refer to the small volume surrounding each point on a mesh. Meshfree methods may refer to methods that are based on interaction of nodes or points with all of the neighboring nodes or points. In other words, meshfree methods do not require connection between nodes of the simulation domain. The smoothed-particle Galerkin or hydrodynamics method may be forms of meshfree methods.

At block 304, processing logic may simulate one or more forces and/or displacements on the digital design of the aligner that are associated with removal of the aligner from the dental arch-like structure (e.g., mold or the dental arch of the patient). Simulating the one or more forces and/or displacements on the digital design of the aligner may include performing operations at blocks 306, 308, 310, 312, and 314. At block 306, processing logic may gather one or more material properties (also referred to as material property information) of the aligner. The material properties may include an amount or value of stress and/or strain that the material can sustain before cracking, breaking, deforming, warping, etc. One example of a material property of the material is the Young's Modulus of the material. In some embodiments, the material properties may not change between different digital designs of aligners because the aligners will be made of the same material (e.g., polymeric). Material properties may be included in a configuration of the aligner design analysis module 1450 in embodiments.

At block 308, processing logic may gather a first geometry of the aligner from the digital design of the aligner. The first geometry may be specific to each patient (and to each stage of treatment) and may be determined based on the dental arch of the patient. The first geometry may be obtained by generating the digital design of the aligner by manipulating a digital model of a dental arch-like structure (e.g., of a mold or dental arch of a patient). The digital model of the dental arch-like structure may represent the dental arch of the patient. The digital model of the mold may be offset to approximate a surface of the aligner and to generate the digital design of the aligner. As such, the digital design of the aligner may include cavities configured to receive teeth (referred to as tooth-receiving cavities or caps) of the patient and/or attachments on the teeth.

At block 310, processing logic may gather a second geometry of the dental arch-like structure from a digital model of the dental arch-like structure (e.g., mold). The digital model of the dental arch-like structure may be generated from information obtained by performing an intraoral scan of the patient during a consultation and/or from a treatment plan. For example, the dental arch of the patient may be digitized, via scanning, and modeled as the dental arch used to fabricate the mold. The second geometry may include information related to the dental arch of the patient, such as the tooth size, tooth shape, tooth orientation, distance between teeth, attachments on teeth, upper dental arch, lower dental arch, etc.

At block 312, processing logic may simulate the removal of the aligner having the one or more material properties and the first geometry from the dental arch-like structure having the second geometry by applying the one or more loads (e.g., one or more forces and/or displacements) to a set of points on the digital design of the aligner. The numerical simulation performed may include solving a series of partial differential equations that model applying one or more loads (e.g., forces and/or displacements) to the aligner having the material properties and the first geometry to remove the aligner from the dental arch-like structure having the second geometry. Further, the partial differential equations may calculate a stress or strain value at each point of the set of points on the digital design of the aligner and a determination may be made based on the stress or strain value calculated and the amount of force applied whether the point is a probable point of damage. The partial differential equations may be elastostatic or elastodynamic partial differential equations that calculate stress or strain states within the digital design of the aligner, and thus, predict breakage, warpage, deformation, etc. High polymeric strains/stresses may be factors that cause crack initiation and breakage, as well as warpage, deformation, and the like, in polymeric aligners. The partial differential equations may be represented as follows:

Find $u_i$ ($u \in \mathbb{R}^3$) such that:

$$\rho \frac{\partial^2 u_i}{\partial t^2} = \sigma_{ij,i} + f_i \text{ in } \Omega \times [0, T], i, j = 1, 2, 3$$

With boundary conditions:

$u_i(x,t) = u_i^g(x,t)$ at $x \in \partial \Omega_{u_i}$ $\sigma_{ij} n_j = \bar{t}_i(x,t)$ at $x \in \partial \Omega_{\bar{t}_i}$ And initial conditions:

$u_i(x,0) = u_{i0}(x)$ at $x \in \partial \Omega_{u_i}$ $v_i(x,0) = v_{i0}(x)$ at $x \in \partial \Omega_{u_i}$ Given $u_i^g, \bar{t}_i, f_i, u_{i0}, v_{i0}, \sigma_{ij} = \mathbb{C}_{ijkl} \varepsilon_{kl}, \varepsilon_{kl} = \frac{1}{x}\left(\frac{\partial u_k}{\partial x_l} + \frac{\partial u_l}{\partial x_k}\right), \rho$ $\partial \Omega = \partial \Omega_{u_i} \cup \partial \Omega_{\bar{t}_i}, \partial \Omega_{u_i} \cap \partial \Omega_{\bar{t}_i} = \phi, i = 1, 2, 3$ Where u is the 3D displacement field, $u_i^g$ is the Dirichlet boundary condition, $\bar{t}_i$ is the Neumann boundary condition, $f_i$ is the applied body force, $u_{i0}, v_{i0}$ are the initial displacement and velocities, $\sigma_{ij}$ and $\varepsilon_{kl}$ are the stress and strain tensors, $\mathbb{C}_{ijkl}$ is the elasticity tensor, $\rho$ is the material density, $\Omega$ is the domain of interest. Note that $$\frac{\partial^2 u_i}{\partial t^2} = 0$$

can be set, and the elastostatics problem can be solved.

At block 314, for each point of the set of points, processing logic may perform operations at blocks 316, and 318. At block 316, processing logic may determine whether a value of the stress and/or strain satisfies a damage criteria for each of the points by solving the partial differential equations described above. The damage criteria may be satisfied when the value of the stress and/or strain exceeds a threshold value. The partial differential equations may be used to calculate a strain/stress or deformation energy value at each point of the set of points and an amount of resistive force involved in removing the aligner from the mold at the point. Because the second geometry of the dental arch-like structure is used in the numerical simulation, information relating to the attachments may be correlated with the amount of resistive force. The resistive force associated with removing the digital design of the aligner at the point, and information related to the second geometry of the dental arch-like structure of the dental arch (tooth size, tooth shape, tooth numbers, distance between teeth, attachment types, attachment sizes, attachment numbers, etc.) associated with the point and the resistive force may be stored in a lookup table in some embodiments. The lookup table may be referenced later by simplified models that do not account for the second geometry of the dental arch-like structure. Accordingly, the lookup table may be populated prior to running simplified models that rely on the resistive force as part of their calculations, as described further below.

At block 318, processing logic may determine that the point is a probable point of damage responsive to determining that the value of the strain and/or stress satisfies the damage criteria (e.g., the value of local deformation (strains and stresses) exceeds the threshold (e.g., 1-20% strain or 0.5-20 MPa stress)). If the strain and/or stress value calculated at the point that results from the force exceeds the threshold, then a crack may initiate and breakage may result, the strain/stress or deformation energy may cause warpage of the aligner, deformation of the aligner, or the like. The threshold that is defined for the strain/stress or deformation energy may relate to yield criteria such as von Mises or max/min principal stress/strain or deformation energy that the polymeric material will fail when the strain/stress or deformation energy value reaches a critical value, or may be any suitable configurable threshold.

Figure 3B:
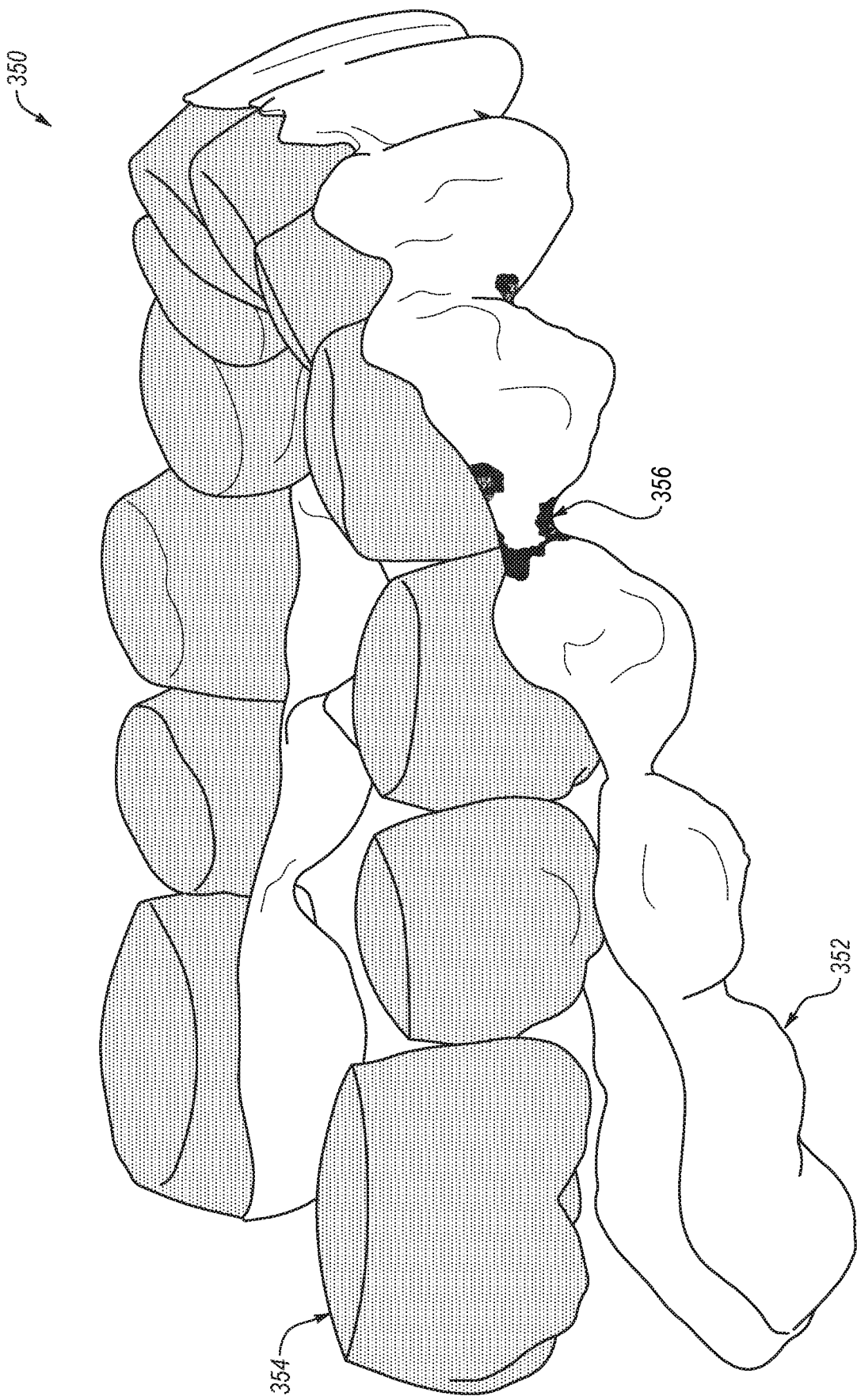
FIG. 3B illustrates an example numerical simulation associated with removal of a digital design of a polymeric aligner from a dental arch-like structure, in accordance with one embodiment.

FIG. 3B illustrates an example numerical simulation 350 associated with removal of a digital design of an aligner 352 from a digital model of a dental arch-like structure 354, in accordance with one embodiment. The numerical simulation 350 graphically represents the solving of the partial differential equations as one or more forces and/or displacements are applied to the digital design of the aligner 352 to remove the digital design of the aligner 352 from the digital model of the dental arch-like structure 354. As depicted, a set of points (represented as triangles in the digital model of the aligner 352) are included in the digital design of the aligner 352 and the partial differential equations calculates a stress or strain value at each of the points, as well as the amount of resistive force involved in removing the digital design of the aligner 352 from the digital model of the dental arch-like structure (e.g., mold) 354 at that point. The numerical simulation 350 may use color-coded shading related to the strain or stress value. A first color, shading or hashing may represent a stress or strain value below a threshold and a second color, shading or hashing may represent a stress or strain value that exceeds the threshold. Any number of colors, shadings and/or hashes may be used to represent various strain/stress or deformation energy values along a scale. For example, processing logic may calculate a strain value for points 356 that is below the threshold value, and thus, shade the points the first color (e.g., blue) or first hashing, which indicates that the points 356 are not probable points of damage because their strain or stress value does not exceed the threshold value. In some embodiments, the shading may be based on the amount of resistive force involved in removing the digital design of the aligner 352 from the digital model of the dental arch-like structure (e.g., mold) 354. If the amount of resistive force exceeds a threshold value, then a probable point of damage may be identified and those points may be shaded the second color (e.g., red) or hashing.

Figure 4A:
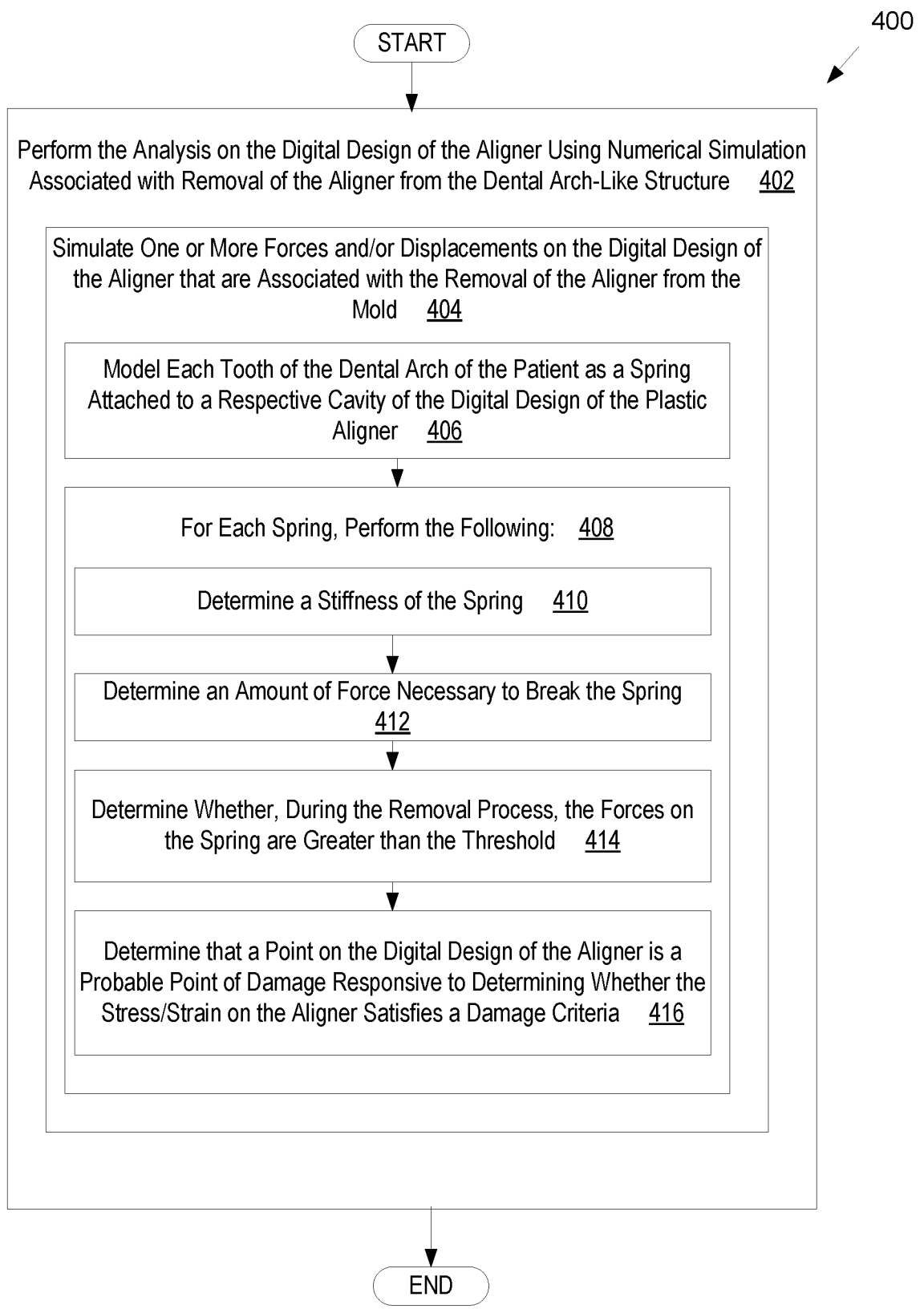
FIG. 4A illustrates a flow diagram for a method of performing analysis on a digital design of a polymeric aligner using numerical simulation by modeling teeth and bonded attachments of a dental arch as springs, in accordance with one embodiment.

FIG. 4A illustrates a flow diagram for a method 400 of performing analysis on a digital design of an aligner (e.g., a polymeric aligner) using numerical simulation by modeling teeth and bonded attachments of a dental arch as springs, in accordance with one embodiment. One or more operations of method 400 are performed by processing logic of a computing device. The processing logic may include hardware (e.g., circuitry, dedicated logic, programmable logic, microcode, etc.), software (e.g., instructions executed by a processing device), firmware, or a combination thereof. For example, one or more operations of method 400 may be performed by a processing device executing an aligner design analysis module 1450 of FIG. 14. It should be noted that the method 400 may be performed for each unique aligner for each patient's treatment plan, or for each unique aligner at key stages of the treatment plan. Further, method 400 includes operations that may be performed during block 104 of FIG. 1A.

At block 402, processing logic may perform the analysis on the digital design of the aligner using numerical simulation associated with removal of the aligner from tooth-like or dental arch-like structures (such as the mold or patient dentition). The numerical simulation may include finite element analysis, finite element method, finite difference method, finite volume method, meshfree methods, smooth particle method, or the like.

At block 404, processing logic may simulate one or more forces and/or displacements on the digital design of the aligner that are associated with removal of the aligner from the dental arch-like structure. Simulating the one or more forces and/or displacements on the digital design of the aligner may include performing operations at blocks 406 and 408. At block 406, processing logic may model each tooth of the dental arch of the patient as a potentially breakable connector (e.g., spring) attached to a respective cavity of the digital design of the polymeric aligner. Modeling each tooth as a spring may be computationally less expensive and time consuming than using the second geometry of the digital model of the mold. The modeled springs may be used to determine reaction strains and stresses and determining the effects of those strains and stresses at portions of the digital design of the polymeric aligner. The calibration of the spring parameters can be determined by various techniques such as experiments and more detailed computational models.

At block 408, for each spring, processing logic may perform operations at blocks 410, 412, 414, and 416. At block 410, processing logic may determine a stiffness of the spring based on the resistive force associated with the tooth being modeled and a geometry of the tooth and/or any attachment associated with the tooth that the spring models. In some embodiments, the resistive force may be obtained from the lookup table described above without running the numerical simulation described with reference to FIG. 3A that uses the second geometry of the dental arch-like structure represented by the digital model of the dental arch-like structure. For example, the lookup table may store information that the digital design of the polymeric aligner removed from a particular tooth with 0 attachments breaks at 1 Newton (N) of applied force, the digital design of the polymeric aligner removed from a particular tooth with 1 attachment breaks at 3 N of applied force, the digital design of the polymeric aligner removed from a particular tooth with 2 attachments breaks at 5 N of applied force, etc. In some embodiments, the resistive force may be dynamically calculated using the numerical simulation described with reference to FIG. 3A. The geometry of an attachment and associated tooth may include an undercut of the attachment and/or the tooth. The undercut of the attachment may refer to a height of a lower surface of attachment. A height of the undercut of the attachment can be used to determine a distance that the digital design of the polymeric aligner needs to move to detach from the attachment at the tooth. The stiffness may be determined by dividing the resistive force by the distance of the undercut. The determined stiffness may be measured in Newtons per millimeter (N/mm). For example, a connector stiffness may be 30 N/mm (3 N of resistive force divided by 0.1 mm distance of the undercut).

At block 412, processing logic may determine an amount of force necessary to break the spring by performing the numerical simulation of removing the digital design of the aligner from the spring. In some embodiments, the partial differential equations described above may be used to perform the numerical simulation of removing the digital design of the aligner from the spring. In some instances, a vertical force associated with the spring is used in the partial differential equations and linear operations may be used, as opposed to non-linear operations used in the partial differential equations described with reference to method 300 of FIG. 3A. The partial differential equations may input the spring stiffness and/or the material properties of the aligner to determine the required force. Also, the partial differential equations may compute a strain/stress or deformation energy value at points of the digital design of the aligner that are associated with the spring while the removal of the digital design of the aligner from the spring is being simulated.

At block 414, processing logic may determine whether, during the removal process, the forces on the spring are greater than a threshold amount of force. If the forces are greater than the threshold, then the spring may break. If the forces are greater than the threshold amount of force, one or more strain/stress or deformation energy values at one or more points on the digital design of the aligner may exceed a threshold strain/stress or deformation energy value caused by the excessive force.

At block 416, processing logic may determine that a point on the digital design of the aligner is a probable point of damage responsive to determining whether the stress/strain or deformation energy on the aligner satisfies a damage criteria. The stress/strain or deformation energy may satisfy the damage criteria when a value of the stress/strain or deformation energy exceeds a threshold value. In an embodiment, processing logic may determine that a point on the digital design of the aligner is a probable point of damage responsive to determining that the amount of force required to break the spring associated with the point exceeds the threshold amount of force. One or more corrective actions may be performed in response to determining that there is a probable point of damage. In some embodiments, the digital design of the aligner may be input into the trained machine learning model to verify the probable point of damage.

Figure 4B:
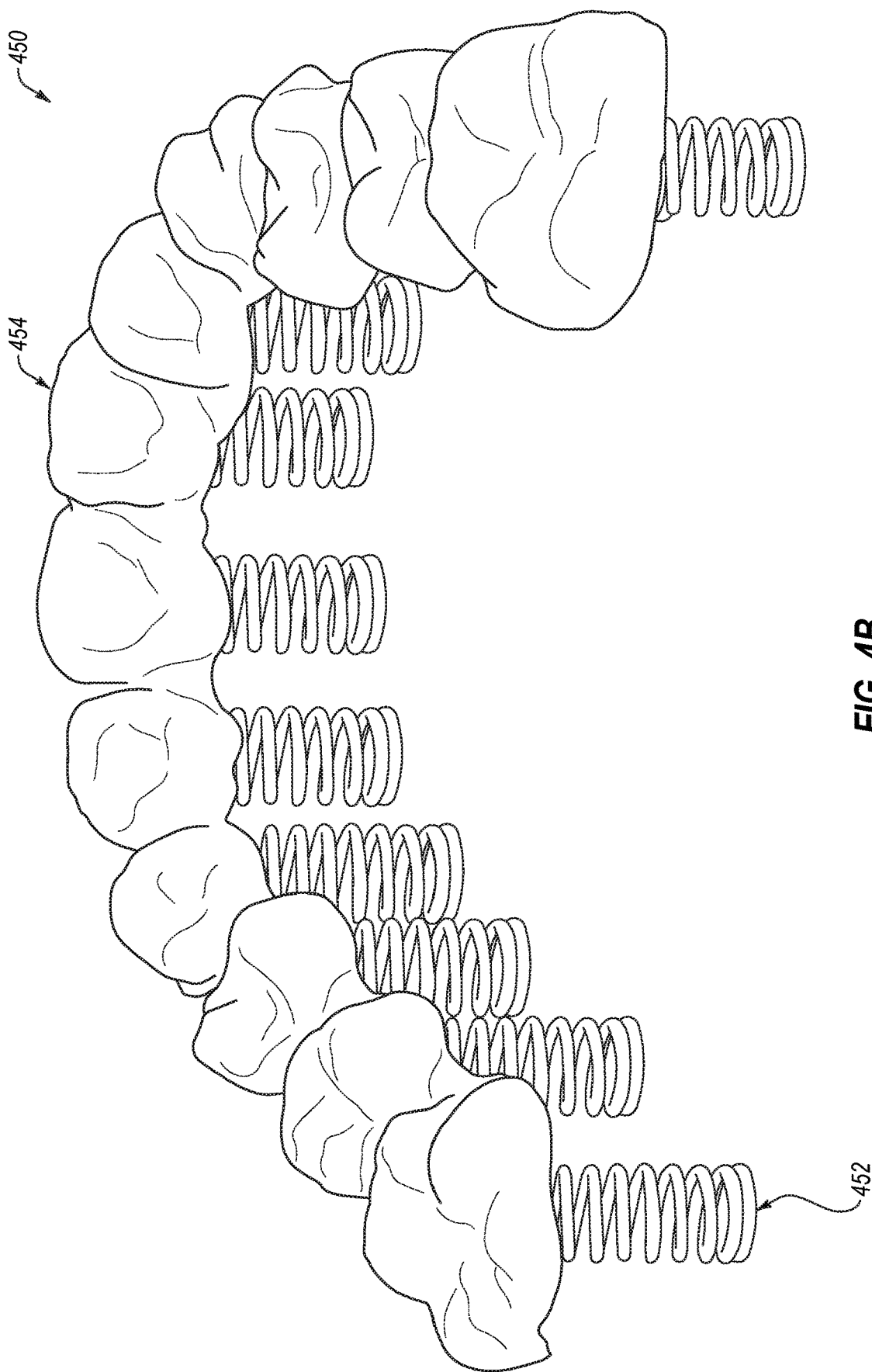
FIG. 4B illustrates an example numerical simulation that models teeth of the dental arch of the patient as springs, in accordance with one embodiment, in accordance with one embodiment.

FIG. 4B illustrates an example numerical simulation 450 that models teeth of the dental arch of the patient as springs 452, in accordance with one embodiment. As depicted, each spring 452 is inserted into a respective cavity of a digital design of the polymeric aligner 454 just as a tooth would be when the aligner is worn or attached to a mold. Each spring 452 may have a stiffness that is determined based on the resistive force associated with removing the digital design of the aligner from a respective tooth that may have attachments, and a geometry of an undercut of an attachment on the teeth. The numerical simulation may simulate removing the digital design of the aligner from each of the springs by applying one or more forces and/or displacements to lift the digital design of the aligner from the springs. If the force required to break the spring is more than a threshold amount of force, then the processing logic may determine a probable point of damage is present at a portion of the digital design of the aligner associated with that spring. It should be understood that the numerical simulation is calculated concurrently for every spring 452 while the digital design of the aligner is being removed.

Figure 5A:
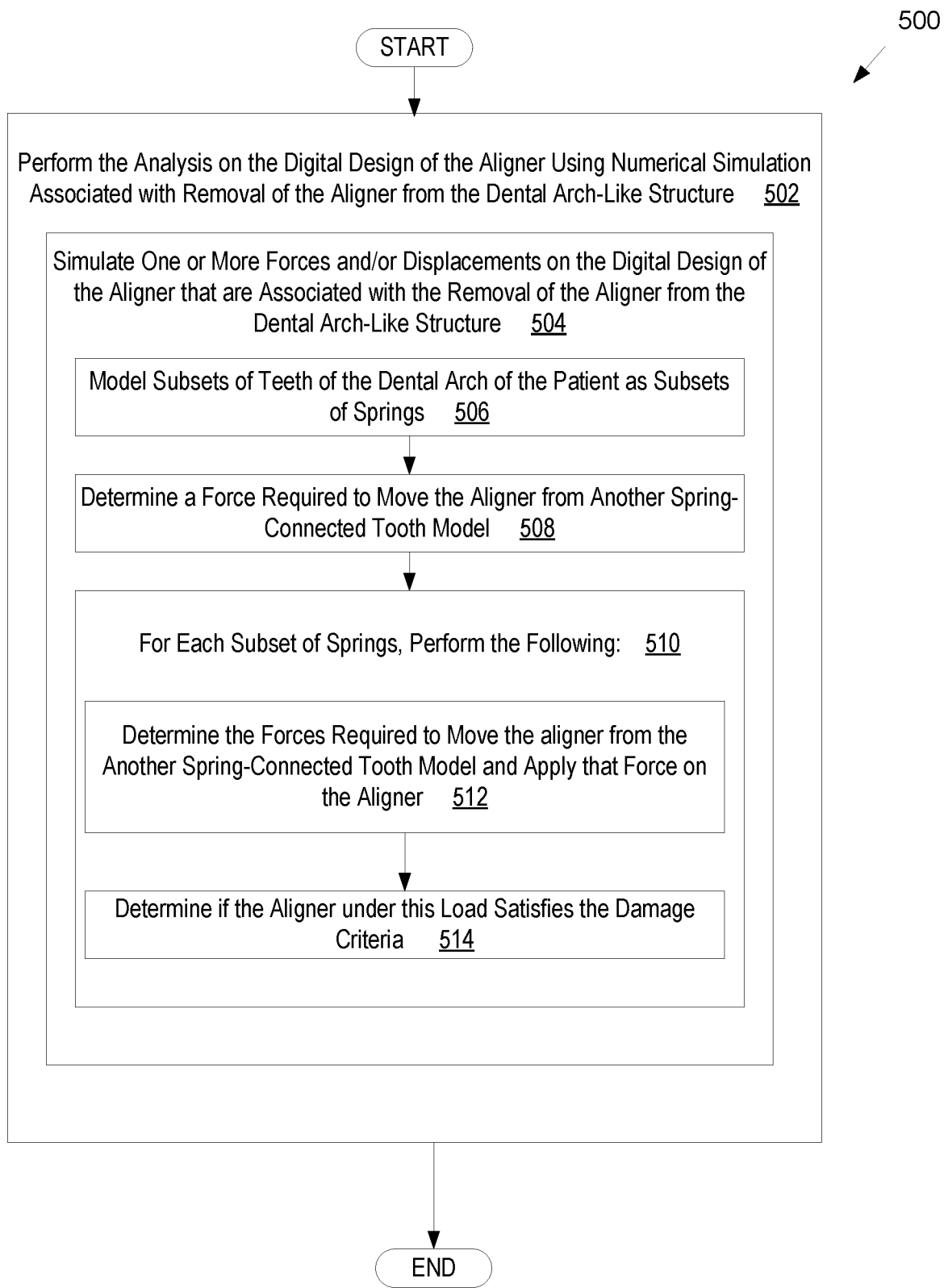
FIG. 5A illustrates a flow diagram for a method of performing analysis on a digital design of a polymeric aligner using numerical simulation by modeling a subset of teeth and bonded attachments of a dental arch as springs, in accordance with one embodiment.

FIG. 5A illustrates a flow diagram for a method 500 of performing analysis on a digital design of an aligner (e.g., a polymeric aligner) using numerical simulation by modeling a subset of teeth and bonded attachments of a dental arch as springs, in accordance with one embodiment. One or more operations of method 500 are performed by processing logic of a computing device. The processing logic may include hardware (e.g., circuitry, dedicated logic, programmable logic, microcode, etc.), software (e.g., instructions executed by a processing device), firmware, or a combination thereof. For example, one or more operations of method 500 may be performed by a processing device executing an aligner design analysis module 1450 of FIG. 14. It should be noted that the method 500 may be performed for each unique aligner for each patient's treatment plan, or for each unique aligner at key stages of the treatment plan. Further, method 500 includes operations that may be performed during block 104 of FIG. 1A.

At block 502, processing logic may perform the analysis on the digital design of the aligner using numerical simulation associated with removal of the aligner from the dental arch-like structure. The numerical simulation may include finite element analysis, finite element method, finite difference method, finite volume method, meshfree methods, smooth particle galerkin method, or the like.

At block 504, processing logic may simulate one or more forces and/or displacements on the digital design of the aligner that are associated with removal of the aligner from the dental arch-like structure (e.g., mold or the dental arch of the patient). Simulating the one or more forces and/or displacements on the digital design of the aligner may include performing operations at blocks 506, 508, and 510. At block 506, processing logic may model subsets of teeth of the dental arch of the patient as subsets of springs. Each spring of the subsets of springs may be attached to a respective cavity of the digital design of the aligner. It should be understood that not every tooth in the dental arch of the patient is modeled as a spring in this embodiment. Each of the subset of springs may model at least one different tooth than another subset of springs. The subsets of springs are used in different numerical simulations of removing the aligner from the dental arch-like structure. By only performing the numerical simulation using a subset of springs, less computations are concurrently performed and the numerical simulation may perform faster than performing the numerical simulation on every spring modeling every tooth of the dental arch. The method 500 may iterate through performing the numerical analysis on different subsets of springs until every spring has been involved in a numerical simulation of removing the digital design of the aligner.

At block 508, processing logic may determine a force required to move the aligner from another spring-connected tooth model (e.g., the model described with reference to the method 400 in FIG. 4A). At block 510, for each spring of a subset of springs in a simulation, processing logic may perform operations at block 512 and 514. At block 512, processing logic may determine the forces required to move the aligner from the another spring-connected tooth model and apply that force on the aligner. At block 514, processing logic may determine if the aligner under this load satisfies the damage criteria. The damage criteria may relate to a value of stress/strain or deformation energy exceeding a threshold value. In an embodiment, processing logic may determine that a point on the digital design of the aligner is a probable point of damage responsive to determining that the amount of force required to break the spring associated with the point exceeds the threshold amount of force. One or more corrective actions may be performed in response to determining that there is a probable point of damage. In some embodiments, the digital design of the aligner may be input into the trained machine learning model to verify the probable point of damage.

Figure 5B:
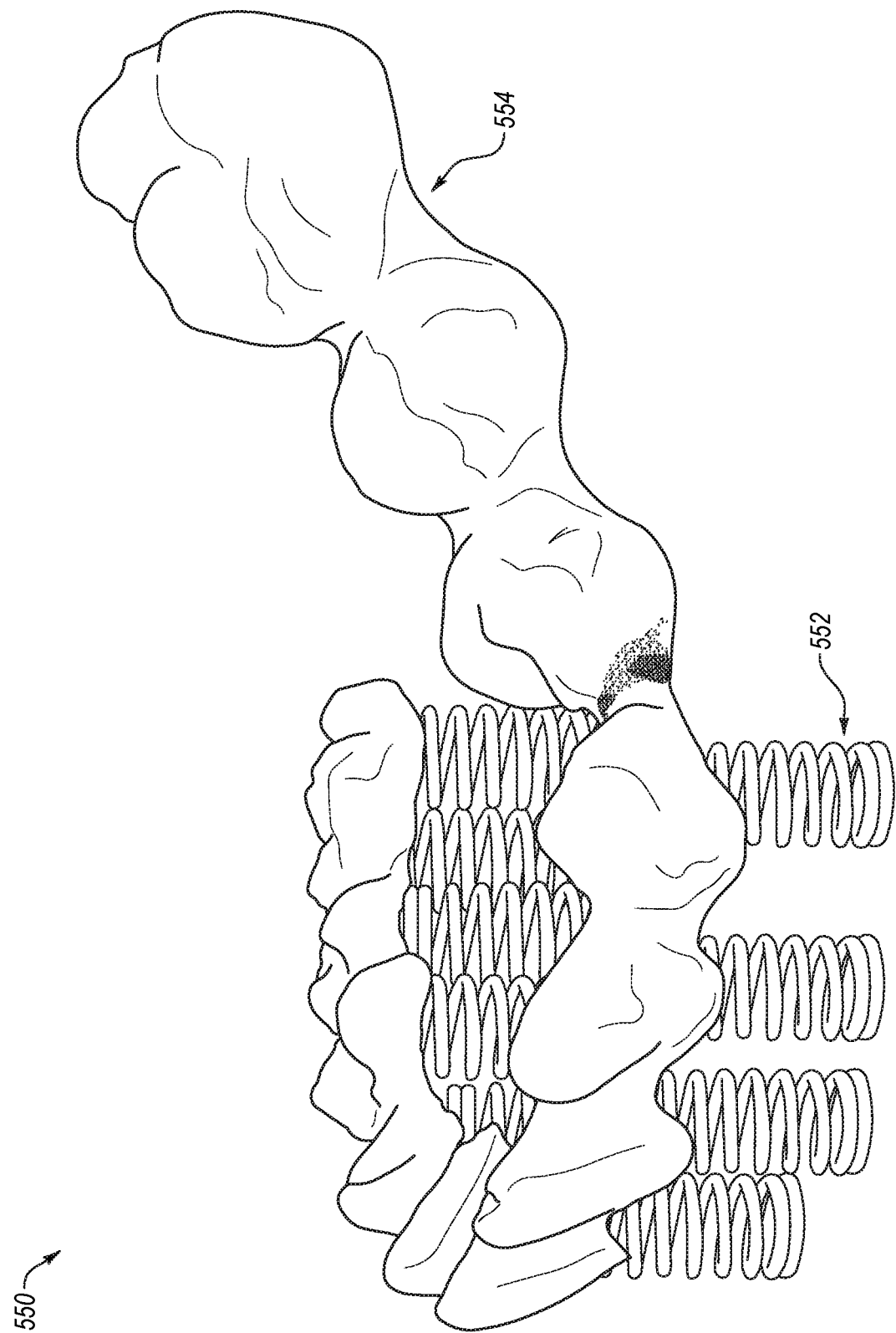
FIG. 5B illustrates an example numerical simulation that models a subset of teeth of the dental arch of the patient as springs, in accordance with one embodiment, in accordance with one embodiment.

FIG. 5B illustrates an example numerical simulation 550 that models a subset of teeth of the dental arch of the patient as springs 552, in accordance with one embodiment. As depicted, a subset of springs 552 are inserted into respective cavities of a digital design of the aligner 554 just as a tooth would be when the aligner is worn or attached to a mold. Springs are not included in some of the cavities of the digital design of the aligner 554 in the depicted numerical simulation 550. Different subsets of springs may be modeled in different numerical simulations until every modeled spring for every tooth is involved in a numerical simulation of removing the digital design of the aligner 554. Each spring 552 may have a stiffness that is determined based on the resistive force associated with removing the digital design of the aligner from a respective tooth that may have attachments, and a geometry of an undercut of an attachment on the teeth. The numerical simulation may simulate removing the digital design of the aligner from the subset of springs by applying one or more forces to lift the digital design of the polymeric aligner from the subset of springs. If a vale of stress/strain or deformation energy at any point on the spring satisfies a damage criteria by exceeding a threshold value, then the processing logic may determine a probable point of damage is present at a portion of the digital design of the aligner associated with that first spring. It should be understood that the numerical simulation is calculated concurrently for every spring 552 in the subset of springs while the digital design of the aligner is being removed.

Figure 6A:
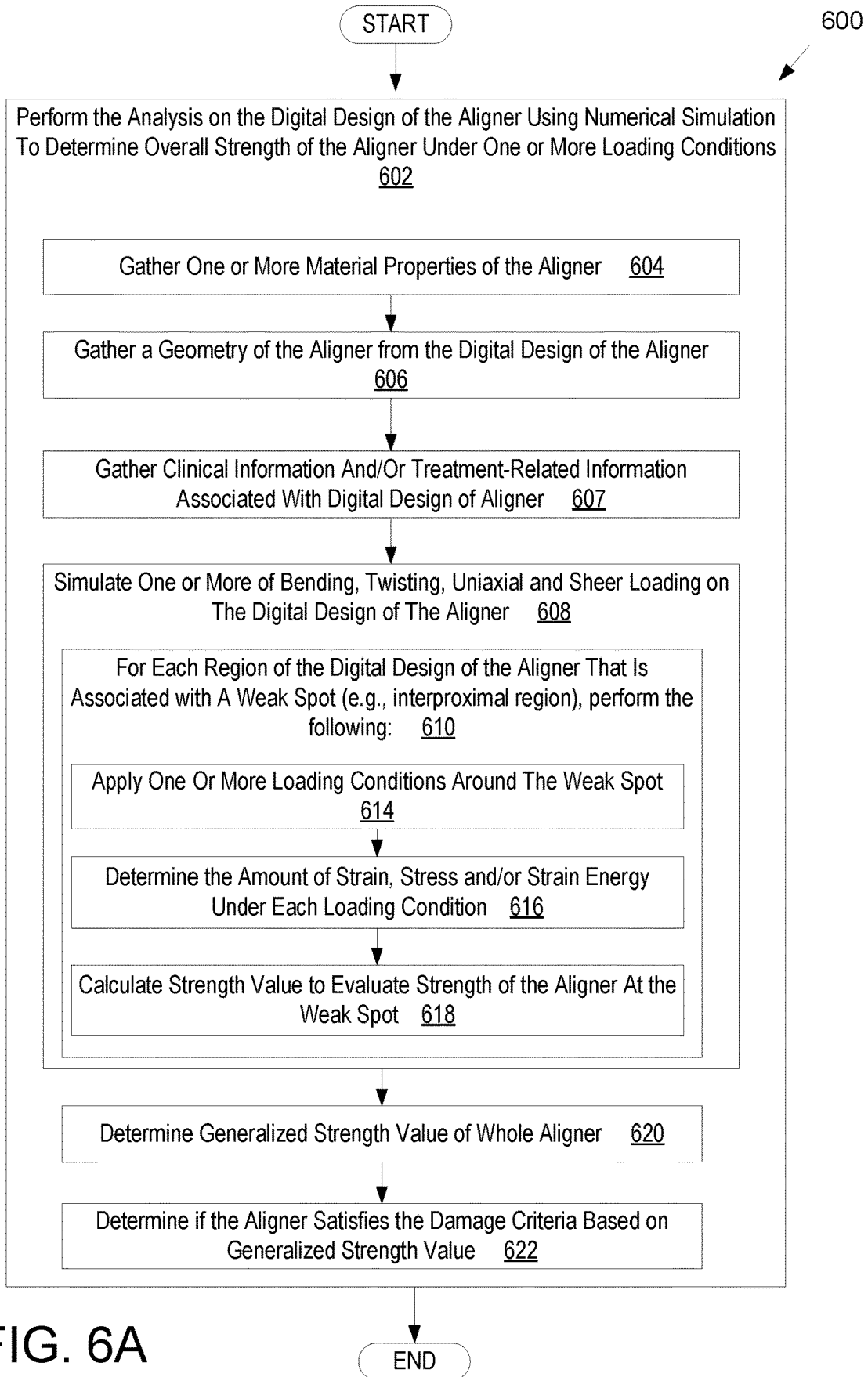
FIG. 6A illustrates a flow diagram for a method of performing analysis on a digital design of an aligner (e.g., a polymeric aligner) using numerical simulation, in accordance with one embodiment.

FIG. 6A illustrates a flow diagram for a method 600 of performing analysis on a digital design of an aligner (e.g., a polymeric aligner) using numerical simulation, in accordance with one embodiment. One or more operations of method 600 are performed by processing logic of a computing device. The processing logic may include hardware (e.g., circuitry, dedicated logic, programmable logic, microcode, etc.), software (e.g., instructions executed by a processing device), firmware, or a combination thereof. For example, one or more operations of method 600 may be performed by a processing device executing an aligner design analysis module 1450 of FIG. 14. It should be noted that the method 600 may be performed for each unique aligner for each patient's treatment plan, or for each unique aligner at key stages of the treatment plan. Further, method 600 includes operations that may be performed during block 104 of FIG. 1A.

At block 602, processing logic may perform the analysis on the digital design of the aligner using numerical simulation to determine an overall strength of the aligner under one or more loading conditions. The numerical simulation may include finite element method, finite difference method, finite volume method, meshfree methods, smoothed-particle methods, combinations of these methods, or the like.

At block 604, processing logic may gather one or more material properties (also referred to as material property information) of the aligner. The material properties may include an amount or value of stress and/or strain that the material can sustain before cracking, breaking, deforming, warping, etc. One example of a material property of the material is the Young's Modulus of the material. In some embodiments, the material properties may not change between different digital designs of aligners because the aligners will be made of the same material (e.g., polymeric). Material properties may be included in a configuration of the aligner design analysis module 1450 in embodiments.

At block 606, processing logic may gather a geometry of the aligner from the digital design of the aligner. The geometry may be specific to each patient (and to each stage of treatment) and may be determined based on the dental arch of the patient. The geometry may be obtained by generating the digital design of the aligner by manipulating a digital model of a dental arch-like structure (e.g., of a mold or dental arch of a patient). The digital model of the dental arch-like structure may represent the dental arch of the patient. The digital model of the dental arch-like structure may be offset to approximate a surface of the aligner and to generate the digital design of the aligner. As such, the digital design of the aligner may include cavities configured to receive teeth (referred to as tooth-receiving cavities or caps) of the patient and/or attachments on the teeth.

At block 607, processing logic may gather clinical information and/or treatment-related information associated with the aligner (and with the digital design of the aligner). The clinical information may include at least one of tooth crowding information, tooth undercut information, tooth geometry information, tooth size, tooth shape, tooth numbers, or distance between teeth, for example. The treatment-related information may include at least one of numbers of attachments associated with one or more of the plurality of tooth receiving cavities, types of attachments associated with one or more of the plurality of tooth receiving cavities, placement locations of attachments on teeth, or precision cut information associated with one or more of the interproximal regions. In some embodiments, such information is included in a lookup table that may be referenced by processing logic and/or by the simulation.

At block 608, processing logic may simulate one or more loads on the digital design of the aligner (e.g., on the geometry of the digital design of the aligner). The simulated loads may include one or more of a bending load, a twisting load, a uniaxial tension load, a uniaxial compression load, a shear load, and/or another load. The simulated load may be a simulated force, moment, or displacement (e.g., translation and/or rotation) in embodiments. Simulating the one or more loads on the digital design of the aligner may include performing operations at blocks 610, 614, 616, and 618.

At block 610, processing logic may select a region of the digital design of the aligner, and may then proceed to perform the operations of blocks 614-618 to test a strength associated with the selected region. At block 610, each of a set of regions may be selected, and the operations of blocks 614-618 may be repeated for each of the regions. The selected regions may each be weak spots of the aligner, such as interproximal regions of the aligner.

Figure 6B:
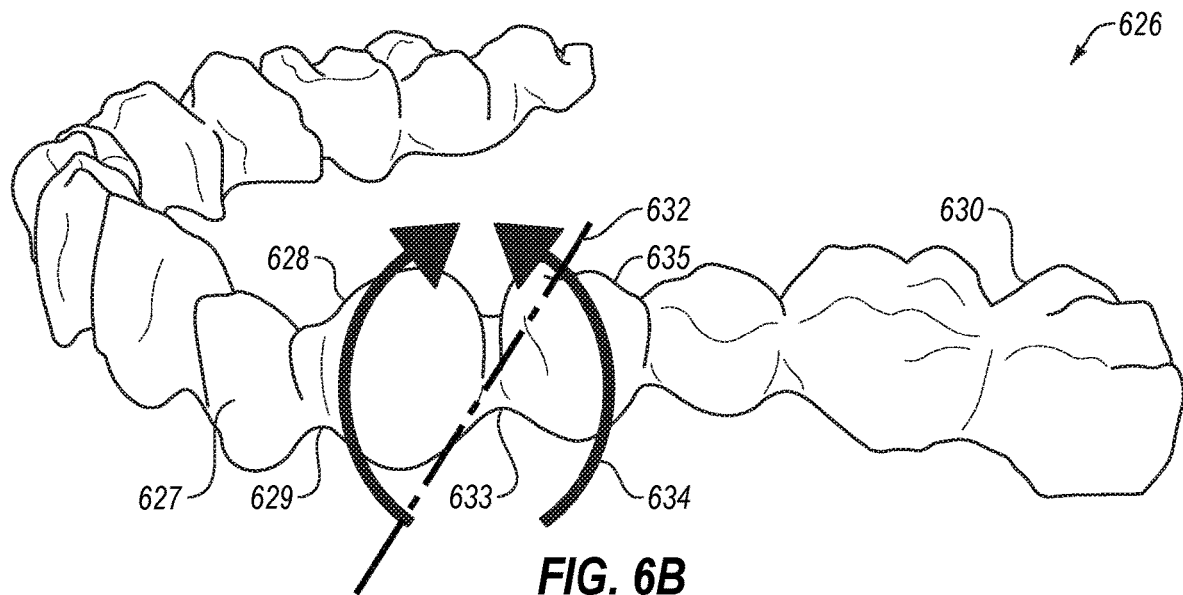
FIG. 6B illustrates application of a bending load around a region of an aligner, in accordance with one embodiment.
Figure 6C:
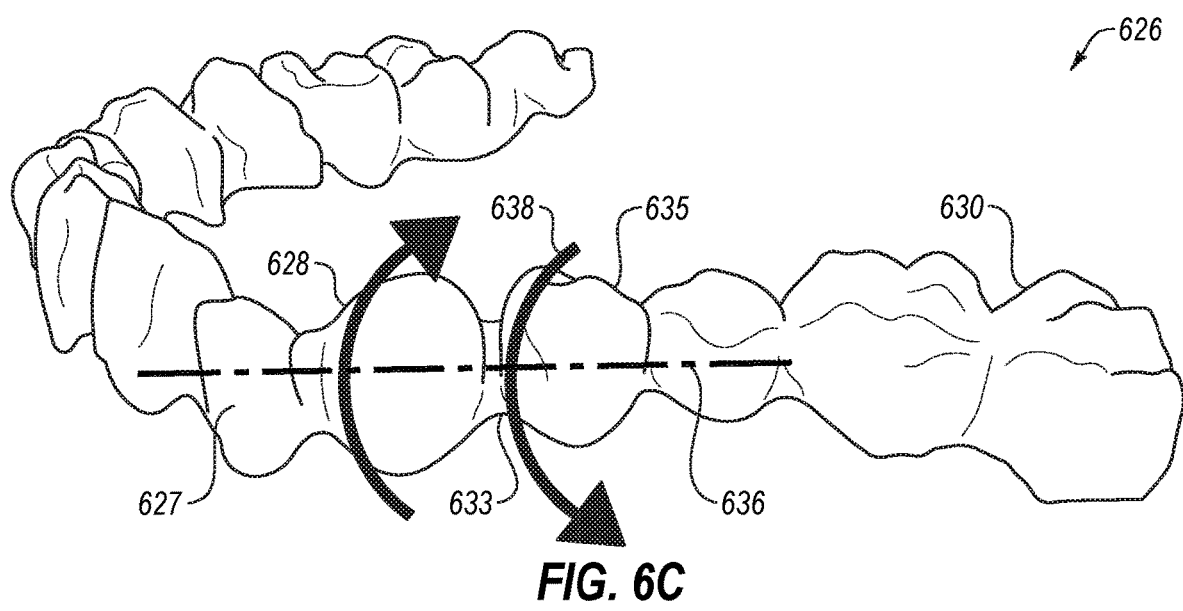
FIG. 6C illustrates application of a twisting load around a region of an aligner, in accordance with one embodiment.
Figure 6D:
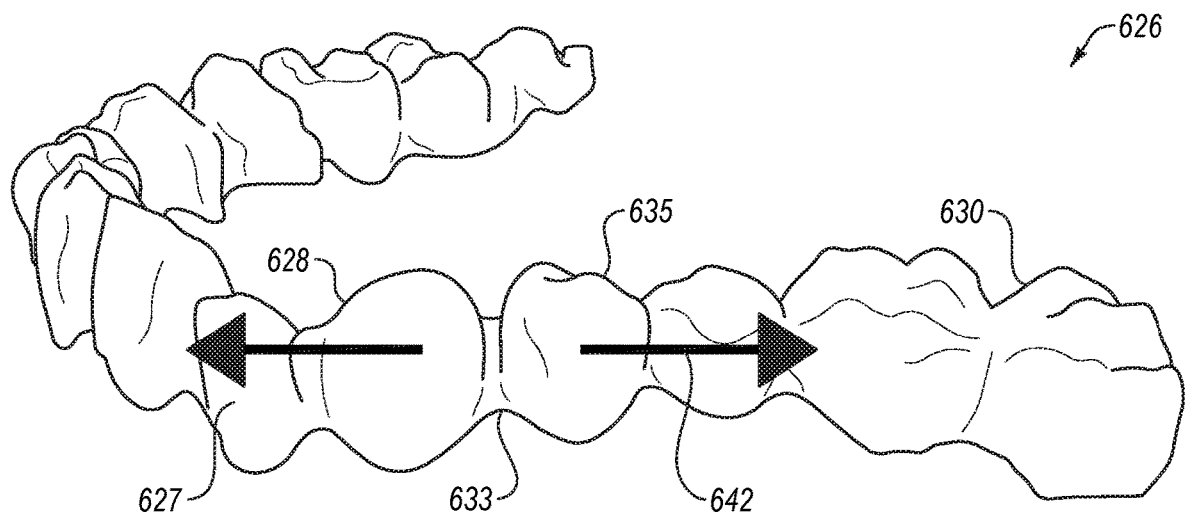
FIG. 6D illustrates application of a uniaxis tension load around a region of an aligner, in accordance with one embodiment.
Figure 6E:
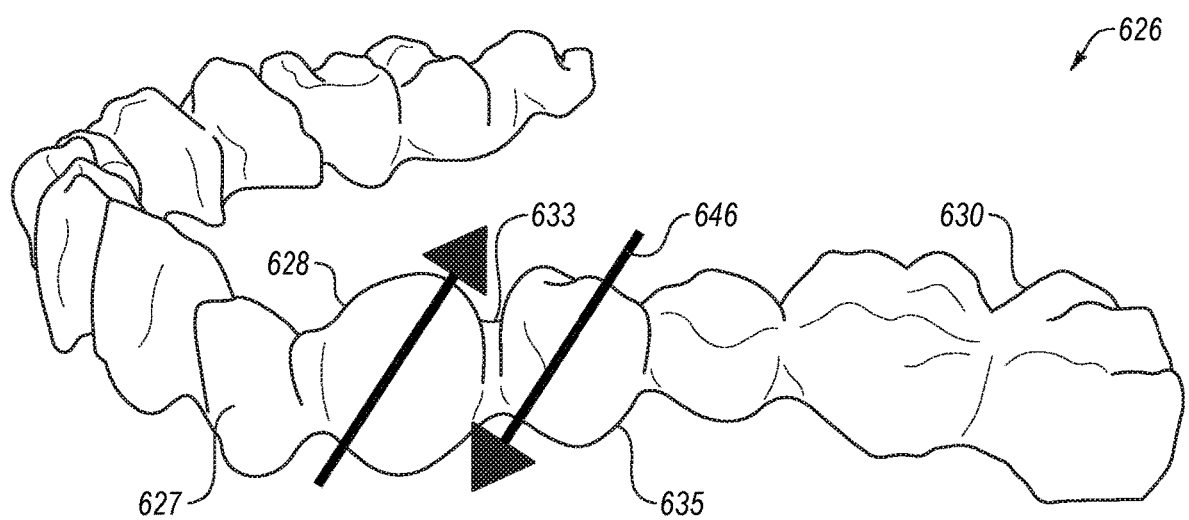
FIG. 6E illustrates application of a shear load around a region of an aligner, in accordance with one embodiment.
Figure 6F:
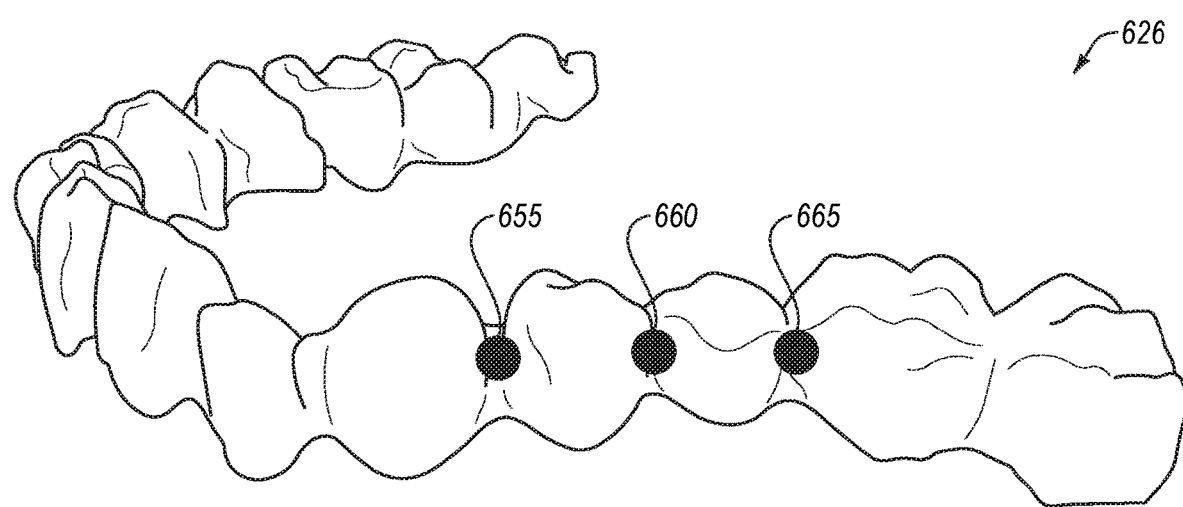
FIG. 6F illustrates weak spots of an aligner, in accordance with one embodiment.

FIG. 6F illustrates weak spots 655, 660, 665 of an aligner 626, in accordance with one embodiment. The weak spots may correspond to interproximal regions of the aligner.

Returning to FIG. 6A, at block 614, processing logic applies one or more loading conditions around a selected region (e.g., around a weak spot or interproximal region. As indicated above, the loading conditions may include a bending load, a twisting load, a uniaxial tension load, a uniaxial compression load, and/or a shear load, which may be applied separately or together. In one embodiment, the load is a moment or force, such as a lifting force, a bending force, a twisting force, a shear force, a tension force, or a compression force. In such an embodiment in which a force or moment is applied, a strain and/or a strain energy may be computed. In one embodiment, the load is a displacement (e.g., a translational displacement and/or a rotational displacement), and a stress may be computed.

A loading condition around a region may be simulated by applying first boundary conditions to one or more regions on a first side of the region and by applying second boundary conditions to one or more additional regions on a second side of the region. For example, a loading condition around an interproximal region may be simulated by fixing one or more first tooth-receiving cavities on a first side of the interproximal region in place and applying a load to one or more second tooth-receiving cavities on a second side of the interproximal region. In one embodiment, the load is applied to occlusal surfaces of the one or more second tooth-receiving cavities.

Clinical information and/or treatment-related information may be correlated with a magnitude of a load that needs to be applied to remove a region of the aligner (e.g., a tooth-receiving cavity of the aligner) from an associated tooth-like structure. For example, the number of attachments on one or more tooth-like structures that are adjacent to a tooth-receiving cavity may affect a resistive force associated with removing the aligner from the dental arch at the tooth-receiving cavity. To account for such interactions in the simulation, an amount of load that is applied around a region (e.g., around an interproximal region) may be based on the number of attachments associated with one or more teeth that are adjacent to the region. Other clinical information and/or treatment related information may also be used to adjust a magnitude of the load that is applied. Such information may include, for example, jaw shape, tooth size, tooth shape, tooth numbers, tooth position, attachment types, attachment sizes, attachment numbers, etc.

FIG. 6B illustrates application of a bending load 634 around a region 633 of an aligner 626, in accordance with one embodiment. The region 633 may be an interproximal region connecting a first tooth-receiving cavity (cap) 628 and a second tooth-receiving cavity (cap) 635. The bending load 634 may be applied about an axis 632 that runs through the region 633. For example, the bending load 634 at interproximal region 633 may be simulated by fixing first tooth-receiving cavity 628 and/or a third tooth-receiving cavity 627 on a first side of the interproximal region 633 in place (e.g., by setting a 0 displacement boundary condition) and applying a load to second tooth-receiving cavity 630 on a second side of the interproximal region 633 (e.g., by setting a force boundary condition or a displacement boundary condition for the second tooth-receiving cavity). In one embodiment, the load is applied to tooth-receiving cavity 630, which may be a most terminal tooth-receiving cavity of the aligner 626. In another embodiment, the bending load 634 is applied to tooth-receiving cavity 635, which is adjacent to tooth-receiving cavity 628. In order to simulate application of a load on a next interproximal region 629, the boundary conditions on tooth-receiving cavity 628 may be removed, and boundary conditions may be set for tooth-receiving cavity 627. The load may then again be applied to tooth-receiving cavity 630.

As mentioned, a magnitude of the load, which might include force, moment, torque, displacement, rotation and so on, that is applied to determine a strain, stress and/or strain energy at a region (e.g., at an interproximal region) may be based on clinical information and/or treatment-related information. In one embodiment, the amount of load to apply around interproximal region 633 is based at least in part on a number of attachments associated with tooth-receiving cavity 628 (e.g., a number of attachments to be placed on a tooth that will mate with tooth-receiving cavity 628) and/or a number of attachments associated with tooth-receiving cavity 627. The presence of attachments on the teeth associated with these tooth-receiving cavities 627, 628 may increase an amount of force that is necessary to remove the aligner from a mold. Accordingly, the load that is simulated for the interproximal region 633 may be increased an amount based on the number of attachments associated with tooth-receiving cavity 627 and/or tooth-receiving cavity 628. In one embodiment, a force of 1 Newton (N) is applied to simulate loading around interproximal region 633 if there are no attachments associated with tooth-receiving cavity 627 and/or if there are no attachments associated with tooth-receiving cavity 628. In one embodiment, for each attachment associated with tooth-receiving cavity 627, a magnitude of the force applied is increased by one Newton, or by another amount, to test the strain at interproximal region 633. In one embodiment, for each attachment associated with tooth-receiving cavity 628, a magnitude of the force is increased by one Newton, or by another amount, to test the strain at interproximal region 633.

FIG. 6C illustrates application of a twisting load 638 around a region of aligner 626, in accordance with one embodiment. The region 633 may be an interproximal region connecting first tooth-receiving cavity (cap) 628 and second tooth receiving cavity (cap) 635. The twisting load 638 may be applied about an axis 636 that runs through the region 633. For example, the twisting load 638 at interproximal region 633 may be simulated by fixing first tooth-receiving cavity 628 and/or third tooth-receiving cavity 627 on a first side of the interproximal region 633 in place (e.g., by setting a 0 displacement boundary condition) and applying a load or displacement to second tooth-receiving cavity 630 on a second side of the interproximal region 633 (e.g., by setting a force boundary condition or a displacement boundary condition for the second tooth-receiving cavity). In one embodiment, the load is applied to tooth-receiving cavity 630, which may be a most terminal tooth-receiving cavity of the aligner 626. In another embodiment, the twisting load 634 is applied to tooth receiving cavity 635, which is adjacent to tooth-receiving cavity 628.

FIG. 6D illustrates application of a uniaxis tension load 642 around a region 633 of aligner 626, in accordance with one embodiment. The region 633 may be an interproximal region connecting first tooth-receiving cavity (cap) 628 and second tooth receiving cavity (cap) 635. The uniaxial tension load 642 may be applied along an axis that runs through the region 633. For example, the uniaxial tension load 642 at interproximal region 633 may be simulated by fixing first tooth-receiving cavity 628 and/or third tooth-receiving cavity 627 on a first side of the interproximal region 633 in place (e.g., by setting a 0 displacement boundary condition) and applying a load to second tooth-receiving cavity 630 on a second side of the interproximal region 633 (e.g., by setting a force boundary condition or a displacement boundary condition for the second tooth-receiving cavity). In one embodiment, the load is applied to tooth-receiving cavity 630, which may be a most terminal tooth-receiving cavity of the aligner 626. In another embodiment, the uniaxis tension load 642 is applied to tooth receiving cavity 635, which is adjacent to tooth-receiving cavity 628.

FIG. 6E illustrates application of a shear load 646 around a region 633 of an aligner, in accordance with one embodiment. The region 633 may be an interproximal region connecting first tooth-receiving cavity (cap) 628 and second tooth receiving cavity (cap) 635. In an example, the shear load 646 at interproximal region 633 may be simulated by fixing first tooth-receiving cavity 628 and/or third tooth-receiving cavity 627 on a first side of the interproximal region 633 in place (e.g., by setting a 0 displacement boundary condition) and applying a load to second tooth-receiving cavity 630 on a second side of the interproximal region 633 (e.g., by setting a force boundary condition or a displacement boundary condition for the second tooth-receiving cavity). In one embodiment, the load is applied to tooth-receiving cavity 630, which may be a most terminal tooth-receiving cavity of the aligner 626. In another embodiment, the shear load 646 is applied to tooth receiving cavity 635, which is adjacent to tooth-receiving cavity 628.

Some loads that may be applied may include a combination of bending, twisting, lifting, shear, compression and/or tension in embodiments. For example, a load that is applied to one or more regions of the aligner may include a first magnitude along an x-axis (e.g., in a buccal direction), a second magnitude along a y-axis (e.g., in a mesial direction) and/or a third magnitude along a z-axis (e.g., in a vertical direction). For example, a load may include a 0 N force along the x-axis, a 0.2 N force along the y-axis, and a 1 N force along the z-axis. The example load may additionally or alternatively include rotational forces about one or more of the x-axis, y-axis and/or z-axis. For example, the example load may include a force of 0 N about the x-axis, a force of 0.2-1.0 N about the y-axis, and a force of 0 N about the z-axis.

Returning to FIG. 6A, at block 616, an amount of strain, stress and/or strain energy (e.g., strain energy density) is determined for each of the simulated loading conditions using the numerical simulation. The amount of strain, stress and/or stress energy may be determined based on the loading conditions and the material property information. Additionally, one or more derived values may be derived from the strain, stress and/or strain energy density. The numerical simulation performed may include solving a series of partial differential equations that model applying one or more loads (e.g., forces and/or displacements) to the aligner having the material properties and the geometry. Further, the partial differential equations may calculate a stress or strain value at the selected region (e.g., at the weak spot or interproximal region). The partial differential equations may be elastostatic or elastodynamic partial differential equations that calculate stress, strain energy and/or strain states within the digital design of the aligner, which may be used to predict breakage, warpage, deformation, etc. In one embodiment, the amount of strain, stress and/or strain energy is determined for an edge of the aligner at the region (e.g., where the region interfaces with a outline of the aligner).

At block 618, processing logic calculates a strength value for the region (e.g., weak spot or interproximal region) based on the determined amount of strain, stress and/or strain energy (e.g., strain energy density) for one or more of the simulated loads. The strength value may additionally or alternatively be based on one or more derived values that are derived from at least one of the strain, the stress and/or strain energy density. In one embodiment, the strength value for the region is based on the strain, stress and/or strain energy density calculated for each of multiple different loading conditions. For example, the strength value for the region may be based on a maximum strain, stress and/or strain energy density from the strains, stresses and/or strain energy density values computed for the region.

A determination may be made based on the strength value for the region whether the region is or includes a probable point of damage. For example, if the maximum calculated stress, strain and/or strain energy density for the region exceeds a threshold, then the region may be identified as a probable point of damage for the aligner.

At block 620, processing logic may determine a generalized strength value of the whole aligner. The generalized strength value may be based on the determined strength values of each of the tested regions. In one embodiment, the strength value corresponds to a minimum strength value of the tested regions.

At block 622, processing logic may determine whether the strength value satisfies a damage criterion or criteria. The damage criteria may be satisfied when the value of the stress and/or strain and/or strain energy density exceeds a threshold value. The partial differential equations may be used to calculate a strain/stress, strain energy density and/or deformation energy value at each tested region.

At block 622, processing logic may determine that the aligner includes one or more probable point of damage responsive to determining that the strength value satisfies the damage criteria (e.g., the value of local deformation (strains and stresses) exceeds the threshold (e.g., 1-20% strain or 0.5-20 MPa stress)). If the strain and/or stress value calculated at the point that results from the force exceeds the threshold, then a crack may initiate and breakage may result, the strain/stress or deformation energy may cause warpage of the aligner, deformation of the aligner, or the like. The threshold that is defined for the strain/stress, strain energy density and/or deformation energy may relate to yield criteria such as von Mises that the polymeric material will fail when the strain/stress or deformation energy value reaches a critical value, or may be any suitable configurable threshold.

If the aligner has a generalized strength value that satisfies the damage criteria (e.g., one or more regions of the aligner have a strain, stress and/or strain energy that exceeds a threshold), then it may be determined that the aligner includes one or more probable points of damage. Responsive to determining that the aligner includes one or more probable points of damage, processing logic may select for the aligner a manufacturing flow for aligners comprising one or more probable points of failure, such as described with reference to FIG. 1B. Alternatively, responsive to determining that the aligner includes one or more probable points of damage, processing logic may implement one or more corrective actions as described above in order to generate a modified digital model of the aligner. Some examples of modifying the digital model of the aligner include modifying a outline radius of the digital model of the aligner (e.g., at an interproximal region that is a probable point of damage), modifying a thickness of a portion of the digital model of the aligner (e.g., at an interproximal region that is a probable point of damage), modifying a geometry of the digital model of the aligner (e.g., at or around an interproximal region that is a probable point of damage), and inserting an indicator in the digital model of the aligner, wherein the indicator represents a recommended place to begin removing the aligner from a mold of the dental arch. In another example, processing logic may generate a modified digital model of a dental arch by modifying one or more attachments on one or more teeth in the digital model of the dental arch, and may then generate the modified digital model of the aligner based on the modified digital model of the dental arch. In another example, processing logic may generate a modified digital model of the dental arch by adding a new virtual filler or enlarging an existing virtual filler to a location on the digital model of the dental arch that is associated with the interproximal region that is the probable point of damage, and may then generate the modified digital model of the aligner based on the modified digital model of the dental arch.

Figure 7A:
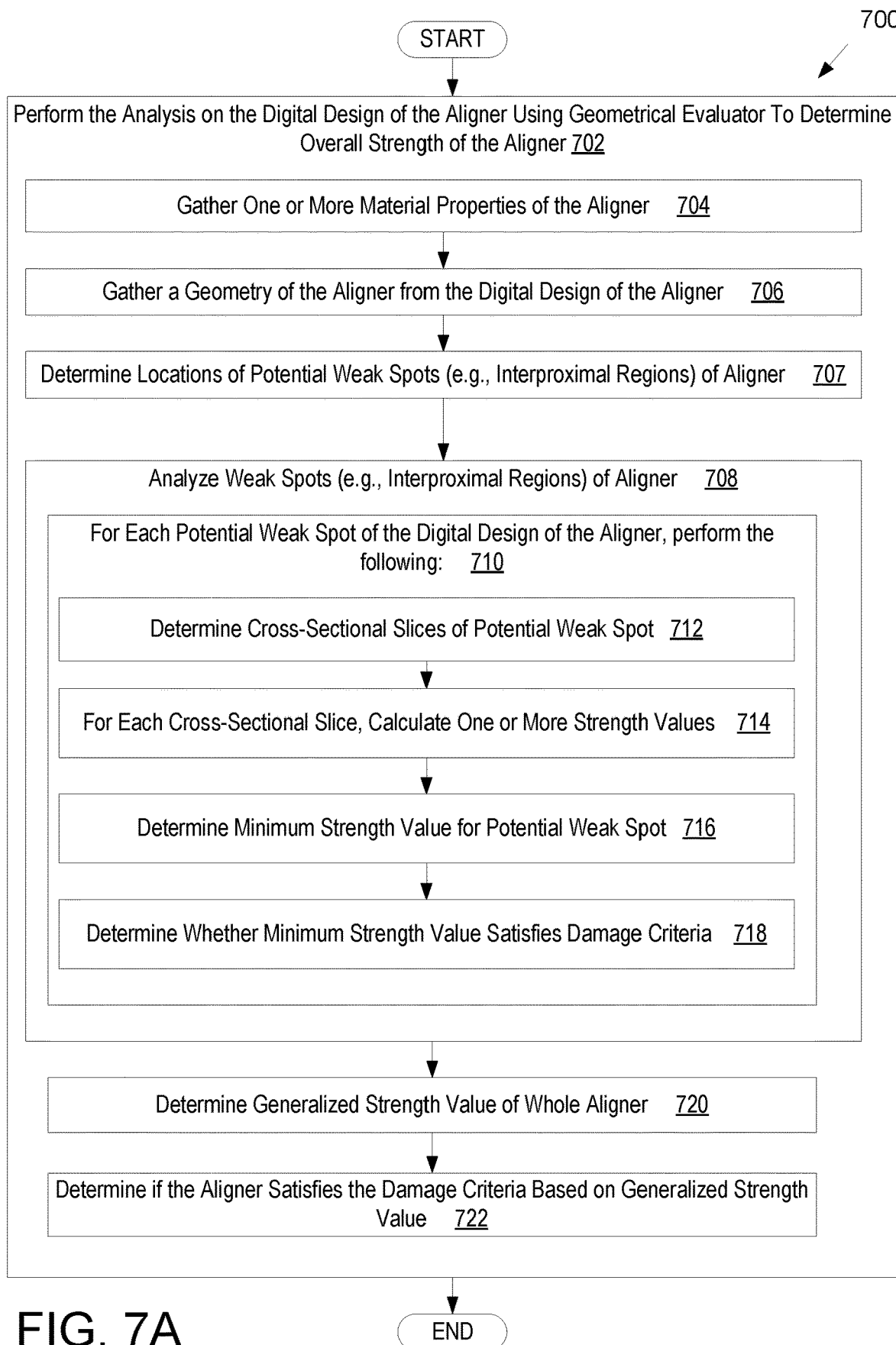
FIG. 7A illustrates a flow diagram for a method of performing analysis on a digital design of an aligner (e.g., a polymeric aligner) using a geometrical evaluator, in accordance with one embodiment.

FIG. 7A illustrates a flow diagram for a method 700 of performing analysis on a digital design of an aligner (e.g., a polymeric aligner) using a geometrical evaluator, in accordance with one embodiment. The geometrical evaluator may be considered as one type of numerical simulation in embodiments. One or more operations of method 700 are performed by processing logic of a computing device. The processing logic may include hardware (e.g., circuitry, dedicated logic, programmable logic, microcode, etc.), software (e.g., instructions executed by a processing device), firmware, or a combination thereof. For example, one or more operations of method 700 may be performed by a processing device executing an aligner design analysis module 1450 of FIG. 14. It should be noted that the method 700 may be performed for each unique aligner for each patient's treatment plan, or for each unique aligner at key stages of the treatment plan. Further, method 600 includes operations that may be performed during block 104 of FIG. 1A.

At block 702, processing logic may perform the analysis on the digital design of the aligner using a geometrical evaluator (e.g., a numerical simulation) to determine an overall strength of the aligner. The geometrical evaluator may determine one or more geometrical properties of the digital design of the aligner at one or more regions of the aligner (e.g., at one or more interproximal regions and/or other weak spots of the digital design of the aligner), and may compute a stress or stiffness, or strength based on the one or more geometrical properties and material properties of a material to be used to manufacture the aligner in embodiments.

At block 704, processing logic may gather one or more material properties (also referred to as material property information) of the aligner. The material properties may include an amount or value of stress and/or strain that the material can sustain before cracking, breaking, deforming, warping, etc. One example of a material property of the material is the Young's Modulus of the material. In some embodiments, the material properties may not change between different digital designs of aligners because the aligners will be made of the same material (e.g., polymeric). Material properties may be included in a configuration of the aligner design analysis module 1450 in embodiments.

At block 706, processing logic may gather a geometry of the aligner from the digital design of the aligner. The geometry may be specific to each patient (and to each stage of treatment) and may be determined based on the dental arch of the patient. The geometry may be obtained by generating the digital design of the aligner by manipulating a digital model of a dental arch-like structure (e.g., of a mold or dental arch of a patient). The digital model of the dental arch-like structure may represent the dental arch of the patient. The digital model of the dental arch-like structure may be offset to approximate a surface of the aligner and to generate the digital design of the aligner. As such, the digital design of the aligner may include cavities configured to receive teeth (referred to as tooth-receiving cavities or caps) of the patient and/or attachments on the teeth.

At block 707, processing logic may determine locations of the potential weak spots such as interproximal regions of the aligner. It is to note that the potential weak spots usually appear at interproximal regions due to weak connection. However, it can exist in other spots as in different dentitions. In one embodiment, the locations of the interproximal regions are determined by first determining centers of the tooth-receiving cavities of the aligner. Lines may then be computed between the centers of each pair of adjacent tooth-receiving cavities. For each pair of adjacent tooth-receiving cavities, a midpoint of the line drawn between the centers of the tooth-receiving cavities may be a midpoint of the interproximal region connecting those two tooth-receiving cavities. The interproximal region connecting the two adjacent tooth-receiving cavities may include the area around the midpoint of the line (e.g., from a first offset in a first direction along the line from the midpoint to a second offset in a second direction along the line from the midpoint).

At block 708, processing logic may analyze the determined potential weak spots (e.g., interproximal regions) of the aligner. Analysis of the potential weak spots may include computing geometrical values of the potential weak spots (e.g., area moments of inertia) and/or computing stresses based on one or more loads applied to the potential weak spots. Analyzing the potential weak spots of the aligner may include performing operations at blocks 710, 712, 714, 716, and 718.

At block 710, processing logic may select a potential weak spot (e.g., an interproximal region) of the digital design of the aligner, and may then proceed to perform the operations of blocks 712-718 to test a strength associated with the selected potential weak spot. At block 710, each of a set of potential weak spots may be selected, and the operations of blocks 712-718 may be repeated for each of the potential weak spots. The selected potential weak spots may be interproximal regions of the aligner in some embodiments.

Figure 7B:
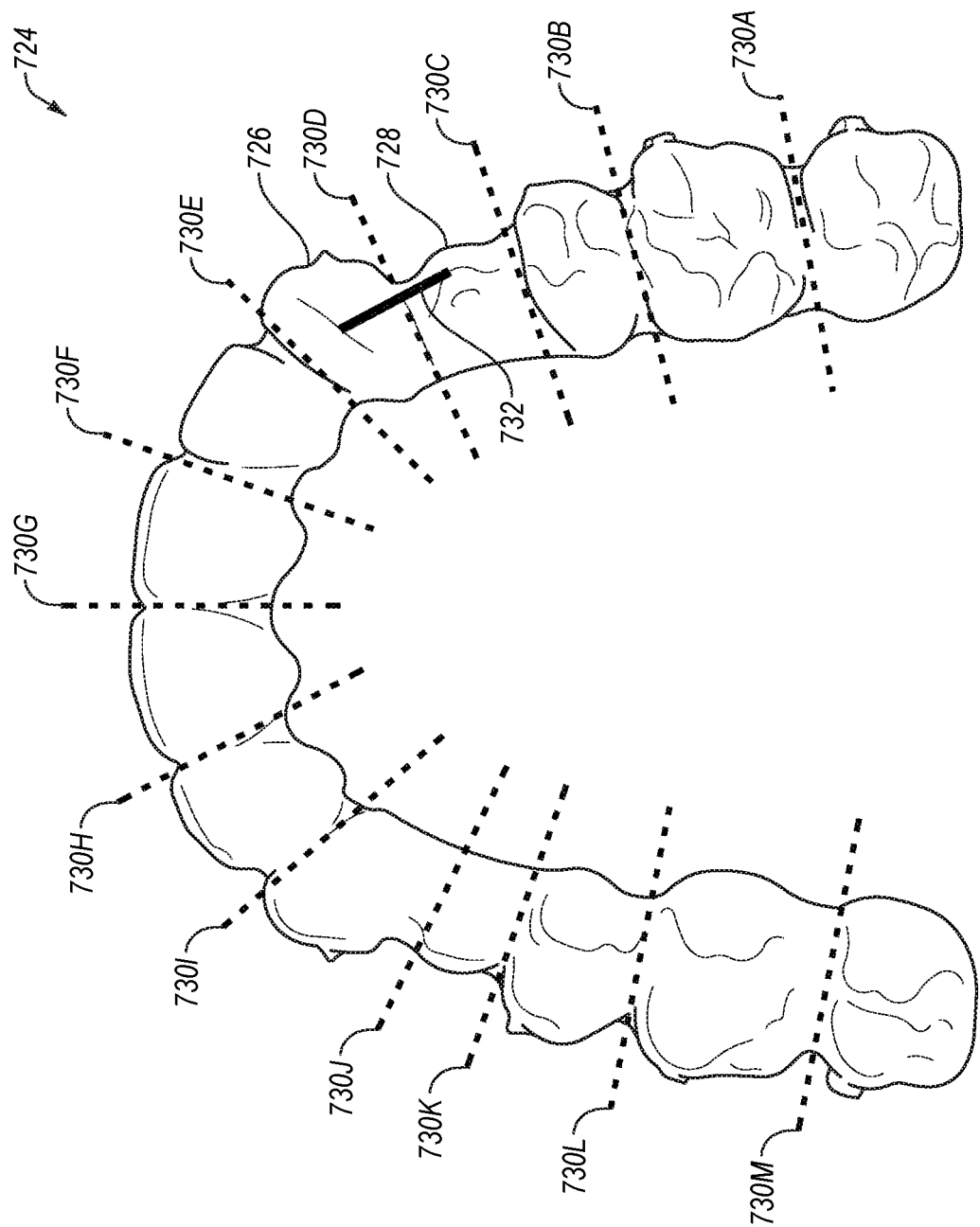
FIG. 7B illustrates an aligner including teeth-receiving cavities and interproximal regions between pairs of teeth-receiving cavities, in accordance with one embodiment.

FIG. 7B illustrates an aligner 724 including teeth-receiving cavities and interproximal regions 730A-M between pairs of teeth-receiving cavities, in accordance with one embodiment. The location of each interproximal region 730A-M may have been determined as set forth above. For example, a center of a first tooth-receiving cavity 726 and a center of a second tooth-receiving cavity 728 may be determined. A line 732 may then be drawn between the center of the first tooth-receiving cavity 726 and the center of the second tooth-receiving cavity 728. The interproximal region 730D may then be determined to be at approximately the midpoint of the line 732. The other interproximal region locations may be similarly determined.

Returning to FIG. 7A, at block 712, processing logic determines one or more cross-sectional slices for a selected potential weak spot. In one embodiment, one or more of the cross-sectional slices are through the midpoint of the potential weak spot (e.g., through the midpoint of an interproximal region). Additional cross-sectional slices may then be taken at locations that are offset from the midpoint along the line. In one embodiment, 5, 10, 15 or 20 cross-sectional slices are generated. Alternatively, other numbers of cross-sectional slices may be generated.

Each cross sectional slice may define a plane comprising a first axis and a second axis. The first axis for each plane may be perpendicular to the line drawn between the centers of the tooth-receiving cavities that the interproximal region in question separates, and may further be perpendicular to a z-axis (where the z-axis is a vertical axis and/or an axis that is normal to an occlusal plane defined by the aligner). A second axis of the planes defined by the cross-sectional slices may be the z-axis. Alternatively, a second axis of the plane for one or more planes defined by cross-sectional slices may be at an angle to the z-axis. In order to determine a cross-sectional slice, processing logic may determine an additional line that is perpendicular to the line connecting the centers of the tooth-receiving cavities and that is perpendicular to the z-axis. A plane may then be determined having a first axis defined by the additional line and having a second axis that is parallel to the z-axis or that is at an angle to the z-axis. The digital model of the aligner may then be sliced by the plane, generating a cross-sectional slice.

Figure 7C:
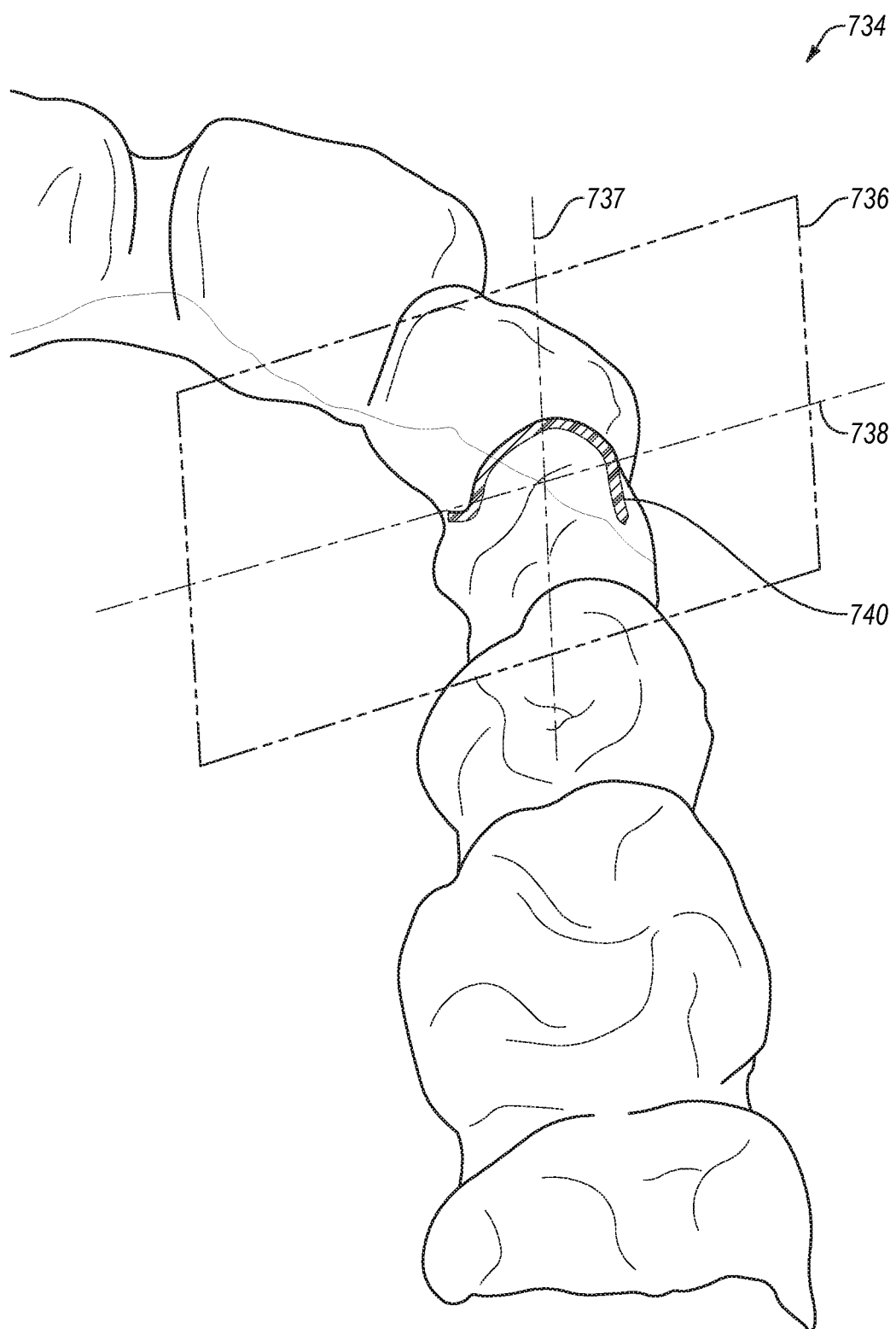
FIG. 7C illustrates a cross-sectional slice taken of an aligner, in accordance with one embodiment.

FIG. 7C illustrates a cross-sectional slice 740 taken of an aligner 734, in accordance with one embodiment. The cross-sectional slice 740 is taken at an interproximal region of the aligner 734 by slicing through the aligner at a plane 736 defined by a first axis 738 and a second axis 737.

Returning to FIG. 7A, at block 714, for each determined cross-sectional slice, one or more strength values are calculated. Such values may be based, for example, on a stress, a strain, a strain energy, or one or more derived values that are derived from the stress, strain and/or strain energy. In one embodiment, one or more area moments of inertia are computed for each slice. The area moment of inertia of a cross-section of aligner is computed separately for each axis of interest. For example, the area moment of inertia of a cross-section may be determined with reference to the first axis of the plane defined by the cross-sectional slice (e.g., x-axis or buccal-lingual axis), with reference to the second axis of the plane defined by the cross-sectional slice (e.g., z-axis or occlusal normal axis), with reference to a third axis that is normal to the plane defined by the cross-sectional slice (e.g., y-axis), and/or with reference to a line on the plane defined by the cross-sectional slice (e.g., the line defined by the equation x=z). The area moment of inertia of a cross sectional slice of the aligner related to an axis may be calculated by:

$$I = \int\int_R x^2 dA$$

Where I is the area moment of inertia, where x is the perpendicular distance from the axis to the element dA, where dA is an elemental area, and where R is an arbitrary shape.

For each area moment of inertia I, one or more stress values a may then be determined. A stress a associated with the area moment of inertia may be computed by:

$$\sigma = \frac{M*d}{I}$$

Where d is the distance to the axis from a point on the aligner, and where M is a moment or force applied at the point.

A maximum stress $\sigma_{max}$ may be computed for each area moment of inertia by:

$$\sigma_{max} = \frac{M*d_{max}}{I}$$

where $d_{max}$ is the largest distance to the axis from any point on the aligner. In some embodiments, the material properties of the material to be used to manufacture the aligner may also be used in the computation of the stress and the maximum stress.

Figure 7D:
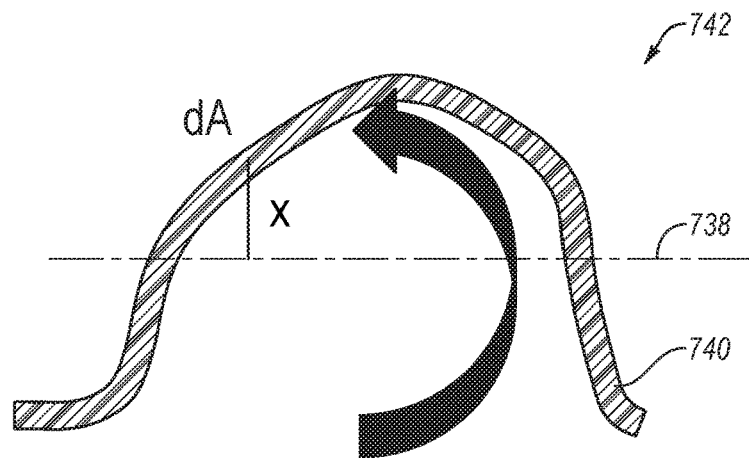
FIG. 7D illustrates a bending load applied around a first axis of the cross-sectional slice of FIG. 7C, in accordance with one embodiment.

FIG. 7D illustrates a bending load 742 applied around a first axis 738 of the cross-sectional slice 740 of FIG. 7C, in accordance with one embodiment. As shown, the area moment of inertia is computed for the cross-sectional slice

740 at the first axis 738. A bending force or moment about the axis 738 is then computed using the area moment of inertia at the first axis 738.

Figure 7E:
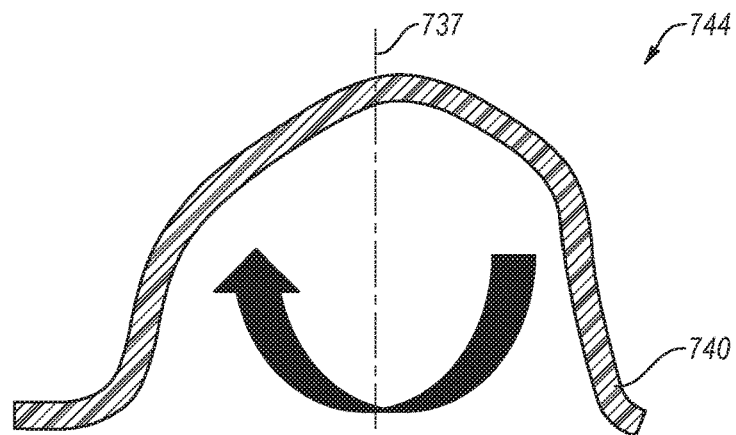
FIG. 7E illustrates a bending load applied around a second axis of the cross-sectional slice of FIG. 7C, in accordance with one embodiment.

FIG. 7E illustrates a bending load 744 applied around a second axis 737 (e.g., of the cross-sectional slice 740 of FIG. 7C, in accordance with one embodiment. As shown, the area moment of inertia is computed for the cross-sectional slice 740 at the second axis 737. A bending force or moment about the axis 737 is then computed using the area moment of inertia at the second axis 737.

Figure 7F:
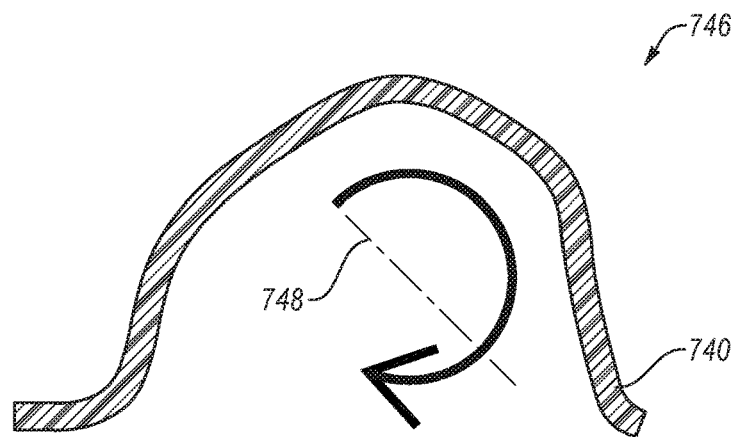
FIG. 7F illustrates a torsion load applied around a third axis normal to the cross-sectional slice of FIG. 7C, in accordance with one embodiment.

FIG. 7F illustrates a torsion load 746 applied around a third axis 748 normal to the cross-sectional slice 740 of FIG. 7C, in accordance with one embodiment. As shown, the area moment of inertia is computed for the cross-sectional slice 740 at the third axis 748. A torsion force or moment about the axis 748 is then computed using the area moment of inertia at the third axis 748.

Returning to FIG. 7A, at block 716, processing logic calculates a minimum strength value for the potential weak spot. In one embodiment, the minimum strength value is computed based on the minimum area moment of inertia and/or the maximum stress computed for the potential weak spot. As noted, multiple cross-sectional slices are generated for the potential weak spot, and multiple area moments of inertia are computed for each cross-sectional slice. Additionally, a maximum stress value may be determined for each area moment of inertia. A minimum area moment of inertia and/or a maximum stress may be determined from the multiple area moments of inertia and/or multiple stress values that are computed for a potential weak spot. The minimum strength value may be, or may be based on, the minimum area moment of inertia and/or the maximum stress computed for the potential weak spot. In one embodiment, a minimum strength value and/or a maximum stress value is selected for each of the types of area moments of inertia that are computed. Accordingly, if four different area moments of inertia are computed, then the minimum strength value may be based on a combination of four different minimum area moments of inertia (e.g., for 4 different axes) and/or on a combination for four different maximum stresses (e.g., for the 4 different axes).

At block 718, processing logic may determine whether the minimum strength value for the potential weak spot (e.g., interproximal region) satisfies one or more damage criteria. The damage criteria may include a stress threshold and/or an area moment of inertia threshold. If the minimum area moment of inertia is below an area moment of inertia threshold and/or if the maximum stress is at or above the stress threshold, then the damage criteria may be satisfied. Processing logic may determine that the potential weak spot is a probable point of damage if the damage criteria are satisfied.

At block 720, processing logic may determine a generalized strength value of the whole aligner. The generalized strength value may be based on the determined strength values of each of the tested potential weak spots. In one embodiment, the strength value corresponds to a minimum strength value of the tested interproximal regions.

At block 722, processing logic may determine whether the strength value satisfies a damage criterion or criteria. The damage criteria may be satisfied when the maximum stress value for any potential weak spot exceeds a stress threshold value and/or when the minimum area moment of inertia for any potential weak spot is below an area moment of inertia threshold.

If the aligner has a generalized strength value that satisfies the damage criteria, then it may be determined that the aligner includes one or more probable points of damage. Responsive to determining that the aligner includes one or more probable points of damage, processing logic may select for the aligner a manufacturing flow for aligners comprising one or more probable points of failure, such as described with reference to FIG. 1B. Alternatively, responsive to determining that the aligner includes one or more probable points of damage, processing logic may implement one or more corrective actions as described above in order to generate a modified digital model of the aligner. Some examples of modifying the digital model of the aligner include modifying a outline radius of the digital model of the aligner (e.g., at an interproximal region that is a probable point of damage), modifying a thickness of a portion of the digital model of the aligner (e.g., at an interproximal region that is a probable point of damage), modifying a geometry of the digital model of the aligner (e.g., at or around an interproximal region that is a probable point of damage), and inserting an indicator in the digital model of the aligner, wherein the indicator represents a recommended place to begin removing the aligner from a mold of the dental arch. In another example, processing logic may generate a modified digital model of a dental arch by modifying one or more attachments on one or more teeth in the digital model of the dental arch, and may then generate the modified digital model of the aligner based on the modified digital model of the dental arch. In another example, processing logic may generate a modified digital model of the dental arch by adding a new virtual filler or enlarging an existing virtual filler to a location on the digital model of the dental arch that is associated with the interproximal region that is the probable point of damage, and may then generate the modified digital model of the aligner based on the modified digital model of the dental arch.

The metrics used in method 700 can either be used directly to predict the probability of aligner/retainer breakage (as discussed above), or can be used as features for training the machine learning model. For example, the area moments of inertia and/or the strain values determined for each of the interproximal regions may be used as inputs to train a machine learning model to predict probable points of damage, as discussed herein above. These metrics may be used along with, or instead of, the metrics previously discussed with reference to training of the machine learning model. For example, embeddings in a training dataset may each include a collection of area moments of inertia and/or strain values associated with one or more interproximal regions of an aligner, and may include a label indicating whether the aligner experienced a point of damage and/or indicating a location of the point of damage (e.g., a particular interproximal region that was damaged).

Figure 7G:
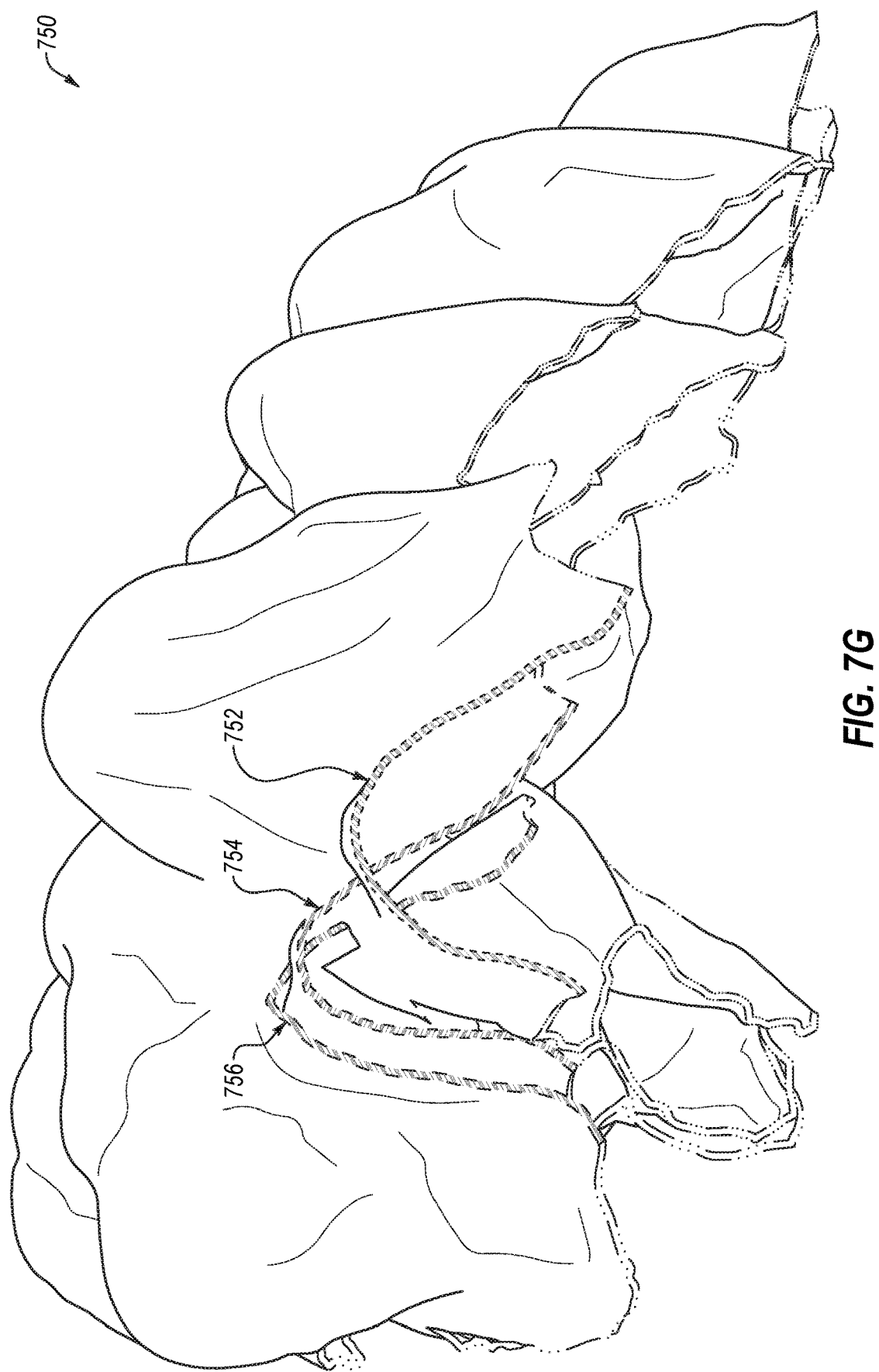
FIG. 7G illustrates an overlay of three different aligners for a dental arch, wherein each of the aligners is associated with a different stage of treatment of the dental arch, in accordance with one embodiment.

FIG. 7G illustrates a superimposition 750 of three different aligners for a dental arch, wherein each of the aligners is associated with a different stage of treatment of the dental arch, in accordance with one embodiment. A first cross-section 752 of a first aligner associated with a first stage of treatment has a relatively wide base and short peak. In comparison, a second cross-section 754 of a second aligner associated with a thirteenth stage of treatment has a narrower base and a taller peak. In further comparison, a third cross-section 756 of a third aligner associated with a twenty sixth stage of treatment has an even narrower base and an even taller peak. Analyses of the three different cross sections would yield a highest area moment of inertia and a lowest stress for the first cross-section 752 and a lowest area moment of inertia and a highest stress for the third cross-section 756. Accordingly, the third aligner may be identified as comprising a probable point of damage and the first aligner may be identified as not comprising a probable point of damage in an example.

There are multiple different loads that are applied on an aligner during its lifetime. Such loads include those caused by a one-time removal of the aligner from a mold used to form the aligner, those caused by insertion and removal of the aligner from a patient's dental arch, and those caused by chewing and/or grinding a patient's teeth together while an aligner is worn and those caused by handling and shipping. For example, during the removal process of the aligner from the mold, some damage (e.g., permanent deformation or strain) may or may not occur to one or more points on the aligner. During intended use, a patient may insert and remove the aligner a few times a day for certain days from one day to 3 weeks. Also, even if it is not recommended for patients to wear aligners while eating, they may still do so. Additionally, while wearing aligners patients may grind their teeth. Each of the aforementioned loads may cause some small amount of damage to the aligner depending on their intensity and amount of occurrence. Initiation and evolution of damage in a point/region might eventually lead to crack initiation and propagation and eventually complete failure/breakage. To predict if a certain aligner design might break or to optimize the shape of the aligner to reduce probability of damage and/or failure, method 800 of FIG. 8A may be performed.

Figure 8A:
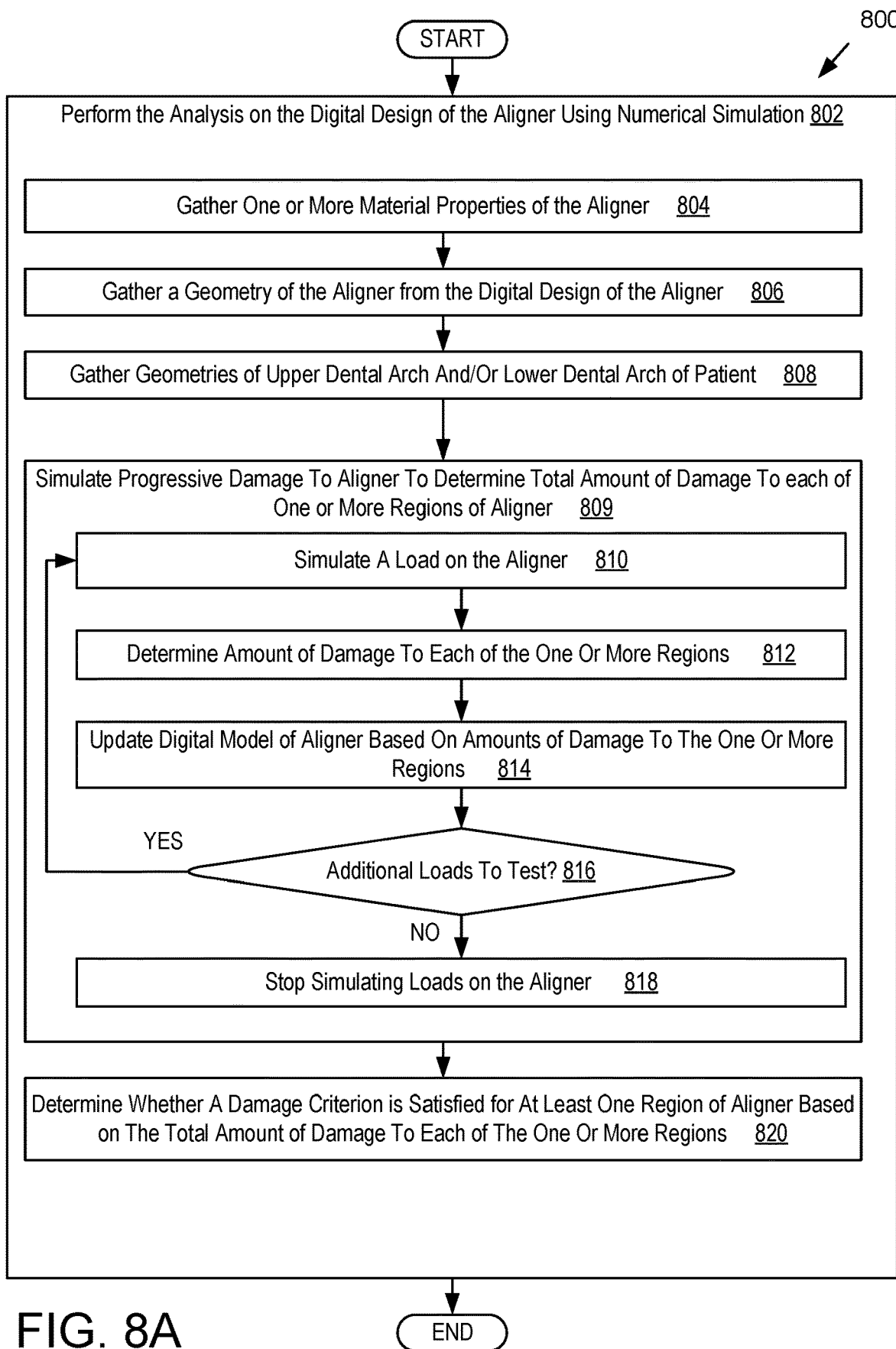
FIG. 8A illustrates a flow diagram for a method 800 of performing analysis on a digital design of an aligner (e.g., a polymeric aligner) using numerical simulation that simulates a sequence of loads on the aligner, in accordance with one embodiment.

FIG. 8A illustrates a flow diagram for a method 800 of performing analysis on a digital design of an aligner (e.g., a polymeric aligner) using numerical simulation that simulates a sequence of loads on the aligner, in accordance with one embodiment. One or more operations of method 800 are performed by processing logic of a computing device. The processing logic may include hardware (e.g., circuitry, dedicated logic, programmable logic, microcode, etc.), software (e.g., instructions executed by a processing device), firmware, or a combination thereof. For example, one or more operations of method 800 may be performed by a processing device executing an aligner design analysis module 1450 of FIG. 14. It should be noted that the method 800 may be performed for each unique aligner for each patient's treatment plan, or for each unique aligner at key stages of the treatment plan. Further, method 800 includes operations that may be performed during block 104 of FIG. 1A. Method 800 may simulate sequential loadings and any associated caused damage from initial manufacture to final use of an aligner. Such a simulation allows processing logic to predict damage initiation, damage evolution, and/or failure/breakage.

At block 802, processing logic may perform the analysis on the digital design of the aligner using numerical simulation. The numerical simulation may include finite element method, finite difference method, finite volume method, meshfree methods, smoothed-particle methods, combinations of these methods, or the like.

At block 804, processing logic may gather one or more material properties (also referred to as material property information) of the aligner. The material properties may include an amount or value of stress and/or strain that the material can sustain before cracking, breaking, deforming, warping, etc. for example elastic modulus, Poisson ratio, yield strength, strain-stress curve, etc. In one embodiment, the material properties include an undamaged response curve and/or a progressive damage curve associated with the material. Material properties may be included in a configuration of the aligner design analysis module 1450 in embodiments.

At block 806, processing logic may gather a first geometry of the aligner from the digital design of the aligner. In embodiments, this may include gathering the digital design of the aligner. The first geometry may be specific to each patient (and to each stage of treatment) and may be determined based on the dental arch of the patient. The first geometry may be obtained by generating the digital design of the aligner by manipulating a digital model of a dental arch-like structure (e.g., of a mold or dental arch of a patient). The digital model of the dental arch-like structure may represent the dental arch of the patient. The digital model of the dental arch-like structure may be offset to approximate a surface of the aligner and to generate the digital design of the aligner. As such, the digital design of the aligner may include cavities configured to receive teeth (referred to as tooth-receiving cavities or caps) of the patient and/or attachments on the teeth.

At block 808, processing logic may gather a second geometry of the dental arch-like structure from a digital model of the dental arch-like structure (e.g., mold). In embodiments, this may include gathering the digital model of the dental arch-like structure. The digital model of the dental arch-like structure may be generated from information obtained by performing an intraoral scan of the patient during a consultation and/or from a treatment plan. For example, the dental arch of the patient may be digitized, via scanning, and modeled as the dental arch used to fabricate the mold. The second geometry may include information related to the dental arch of the patient, such as the tooth size, tooth shape, tooth orientation, distance between teeth, attachments on teeth, upper dental arch, lower dental arch, etc. The dental arch-like structure may represent an upper dental arch or a lower dental arch of a patient at a stage of treatment.

At block 808, processing logic may additionally gather a third geometry of an opposing dental arch-like structure from a digital model of the opposing dental arch-like structure (e.g., mold). In embodiments, this may include gathering the digital model of the opposing dental arch-like structure. The digital model of the opposing dental arch-like structure may be generated from information obtained by performing an intraoral scan of the patient during a consultation and/or from a treatment plan. The third geometry may include information related to the opposing dental arch of the patient, such as the tooth size, tooth shape, tooth orientation, distance between teeth, attachments on teeth, upper dental arch, lower dental arch, etc. The opposing dental arch-like structure may represent an upper dental arch or a lower dental arch of a patient at a stage of treatment.

At block 809, processing logic may simulate progressive damage to the aligner to determine a total amount of damage to each of one or more regions of the aligner. Processing logic may simulate a sequence of one or more forces and/or displacements on the digital design of the aligner that are associated with removal of the aligner from the dental arch-like structure (e.g., mold or the dental arch of the patient), placement of the aligner on the dental arch-like structure, chewing, and so on. Simulating the one or more forces and/or displacements on the digital design of the aligner may include performing operations at blocks 810, 812, 814, 816, and 818.

At block 810, processing logic may simulate a load on the aligner. The load that is simulated may be any of the loads that have been previously discussed (e.g., with reference to FIGS. 3A-7G). Additionally, the load may be simulated using any of the techniques and/or numerical simulations that were previously discussed (e.g., with reference to FIGS.

3A-7G). In one embodiment, the simulated load simulates the removal of the aligner having the one or more material properties and the first geometry from the dental arch-like structure having the second geometry by applying the one or more loads (e.g., one or more forces and/or displacements) to a set of points on the digital design of the aligner (e.g., as discussed with reference to FIGS. 3A-3B, FIGS. 4A-4B, FIGS. 5A-5B, or FIGS. 6A-6F). In one embodiment, the simulated load simulates placement of the aligner on the dental arch-like structure. Such a simulation of a load may be performed, for example, using an inverse of the forces that are applied to remove the aligner from the dental arch-like structure. In one embodiment, the simulated load simulates chewing forces on the aligner, which is discussed in greater detail below with reference to FIG. 8C. In embodiments, the load that is applied includes one or more forces or moments.

At block 812, processing logic determines an amount of damage to each of the one or more regions of the aligner. This may include determining amounts of damage for every region and/or point of the aligner. Damage to regions/points may be determined by first determining an amount of strain at each region/point as discussed above (e.g., with reference to FIGS. 3A-6F). The points on the aligner may be able to endure up to a threshold amount of strain without incurring damage or becoming permanently deformed. However, strain at a point that exceeds the threshold amount of strain may cause damage to the point on the aligner. Accordingly, the measured strain at a point/region of the aligner may be divided into elastic strain and plastic strain. Elastic strain may be temporary strain that is reduced to 0 after force is no longer applied to the aligner. Plastic strain may be permanent strain that may cause a permanent deformation of the aligner. Any amount of plastic strain at a point/region of the aligner may result in an amount of damage to the aligner at that point/region. The amount of damage may be based on a magnitude of the plastic strain. In one embodiment, the amount of damage has a value of 0 to 1, wherein 0 indicates no damage and 1 indicates breakage. The 0 damage value may represent 0% damage, and the 1 damage value may represent 100% damage.

At block 814, processing logic may update the digital model of the aligner based on the amounts of damage (e.g., amounts of plastic strain) at the respective points on the aligner. For each point/region on the aligner, an amount of damage may be recorded. This may be referred to as a damage initiation value applied to the point. Ideally, most or all regions/points on the aligner will have zero damage. The digital model may be updated so that a subsequent simulation of another load on the aligner will be applied to a modified digital model of the aligner, where any damage (e.g., plastic strain) that has already occurred is accounted for in a starting condition of the aligner as included in the modified digital model of the aligner. Additionally, the digital model may be updated by adjusting a geometry of the digital model to account for the plastic strain and reflect any permanent deformation of the aligner associated with the plastic strain.

At block 816, processing logic determines whether any further loads on the aligner are to be simulated. If no additional load on the aligner is to be simulated, the method continues to block 818, and processing logic stops simulating loads on the aligner. If a further load on the aligner is to be simulated, then the method returns to block 810, and another load on the aligner is simulated. In embodiments, a sequence of many different loads may be simulated on the aligner. With each simulation, an amount of damage due to the simulated load may be used to update the digital model of the aligner. This may cause plastic strain to accumulate at certain points of the aligner, which may ultimately lead to those points of the aligner becoming broken or deformed to a magnitude that the aligner no longer serves its intended purpose. In one embodiment, the sequence of simulations of loads on the aligner includes:

1) a simulation of a one-time removal of the aligner from a mold of the dental arch used to form the aligner;
2) repeated simulations of removal of the aligner from the dental arch of the patient and insertion of the aligner onto the dental arch of the patient (e.g., between 10-200 successive simulations of removal and insertion of the aligner); and/or
3) repeated simulations of chewing loads on the aligner.

Different simulation techniques described herein may be used in sequence. For example, the techniques described with reference to FIGS. 3A-3B may be used initially to simulate removal of the aligner from the mold of the dental arch, and the techniques described with reference to FIGS. 4A-4B or FIGS. 6A-6F may subsequently be used to simulate application of the aligner onto the dental arch of the patient and/or removal of the aligner from the dental arch of the patient.

At block 820, processing logic determines whether a damage criterion is satisfied for at least one region/point of the aligner based on the total amount of damage to each of the one or more regions. In one embodiment, the damage criterion is a total amount of accumulated strain. In one embodiment, the damage criterion is 0 damage (e.g., any amount of damage to any point on the aligner causes the aligner to satisfy the damage criterion). In one embodiment, the damage criterion is 2% damage, 5% damage, 10% damage, 15% damage or 20% damage. If the damage criterion is satisfied, then processing logic may initiate one or more corrective actions and/or may select a specific manufacturing flow for the aligner that is associated with aligners with probable points of damage, as discussed in detail earlier in this application.

In some embodiments, the operations of block 820 may be performed after each load is simulated on the aligner. If at any point a damage criterion is satisfied for the aligner, then further simulation on the aligner may not be performed. This may enable processing logic to track a damage evolution path of the aligner and determine at what point during the aligner's life it might fail as well as which of the loadings is most detrimental to the aligner.

Figure 8B:
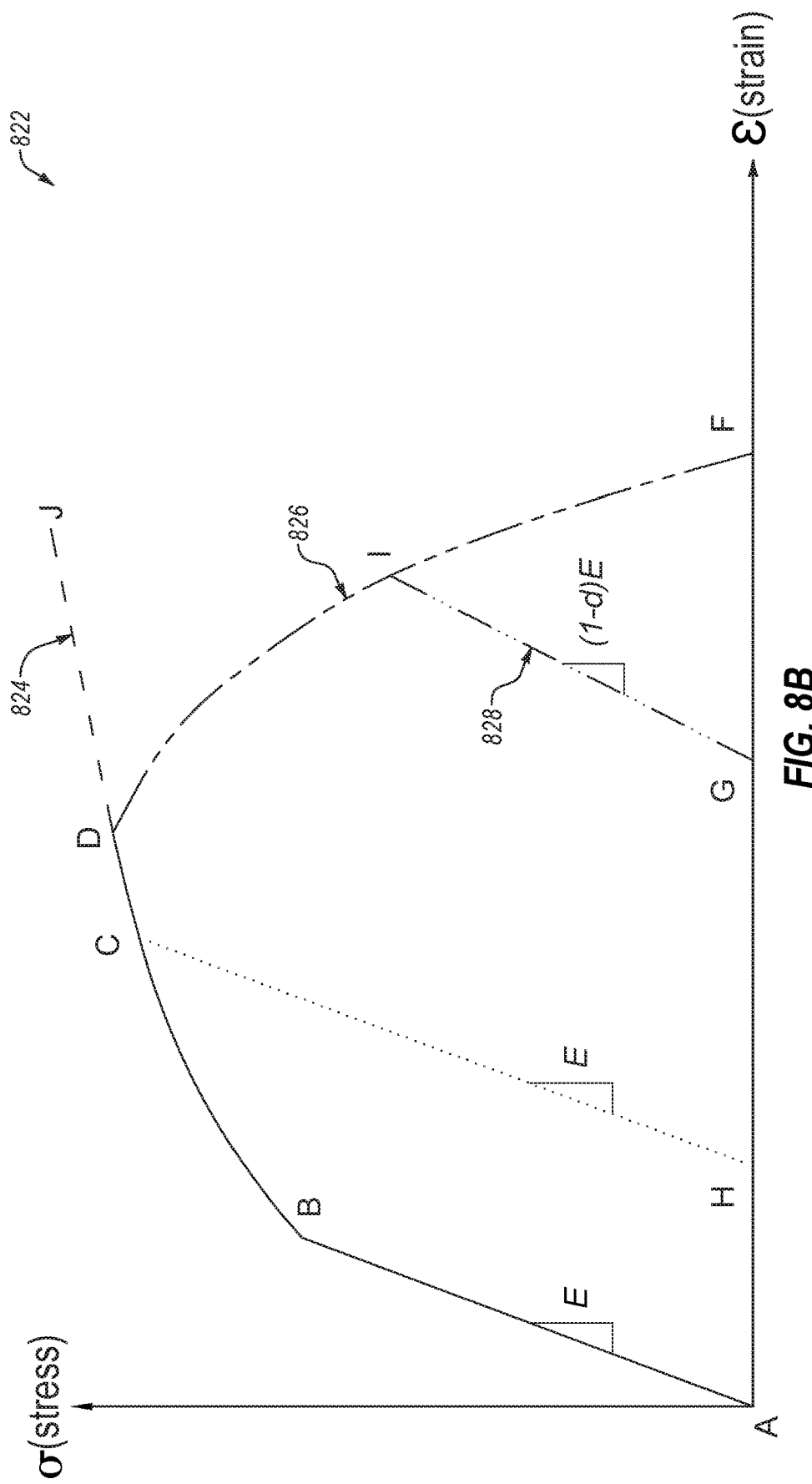
FIG. 8B illustrates a stress strain curve for an aligner, in accordance with one embodiment. Stress (a) may represent force and strain (c) may represent displacement.

FIG. 8B illustrates a stress/strain curve 822 for an aligner, in accordance with one embodiment. Stress (a) may represent force and strain (c) may represent displacement. The stress/strain curve 822 may include an undamaged response curve 824 (between points A, B, D and J) as well as a damage response curve (also referred to as a progressive damage curve) 826 (between points D and F). As force is applied to a point of the aligner, stress increases and the strain also increases according to the undamaged response curve 824 up until the amount of strain reaches an amount sufficient to cause damage initiation (labeled D on the stress/strain curve 822). Between point A and point B, the strain increases linearly with increases in stress according to material properties of the aligner at a rate associated with an elastic modulus or Young's modulus (E) (which is also the slope of the line of the strain stress curve between points A and B). If an amount of strain is equal to or less than the strain at point B, then after a load that causes the strain is removed from the aligner, the strain returns to point A (zero strain). The region between points A and B is called the plastic region, and any strain between point A and point B is elastic strain.

When the strain exceeds point B, the slope changes according to the undamaged response curve 824 up until the strain reaches the damage initiation value at point D. Any strain beyond point B represents plastic strain. Accordingly, the region between points B and D is the plastic region. If the strain is between point B and point D (e.g., at point C), then when the stress is no longer applied to the aligner the strain reduces to a non-zero strain based on the elastic modulus or Young's modulus € (and the initial slope). In the illustrated example, after a stress causes a strain that reaches point C is no longer applied, the strain reduces to point H, which then represents the plastic strain or permanent deformation at the point of the aligner. If further stress is then applied, the strain increases from point H to point C, and then continues along the undamaged response curve 824 as strain increases up to point D.

The portion of the undamaged response curve 824 between points D and J represent what the curve would look like if no damage were to occur. However, past point D damage occurs to the aligner, which follows the damage response curve 826 between points D and F. Any strain that is past point D will cause the material properties of the aligner material to change at the damaged point, which includes a lowered elasticity at that point. This is reflected in a less steep slope for the strain stress response.

In the illustrated example the strain is shown to increase to point I. Once the load is no longer applied and the stress reduces to zero, the strain reduces from point I to point G according to a new slope. The new slope may be computed according to the equation:

$$S=(1-d)E$$

Where S is the new slope for the strain stress curve, d is an amount of damage (from 0 to 1), and E is the elastic modulus. This reflects a degradation of the elasticity of the aligner material at the point that is damaged. If further stress is applied, strain would then increase from point G until point I is reached according to the new slope S. Further increase in the strain would cause the strain to continue to follow the damage response curve 826. If the strain ever reaches point F, then the aligner breaks or cracks at the point.

Figure 8C:
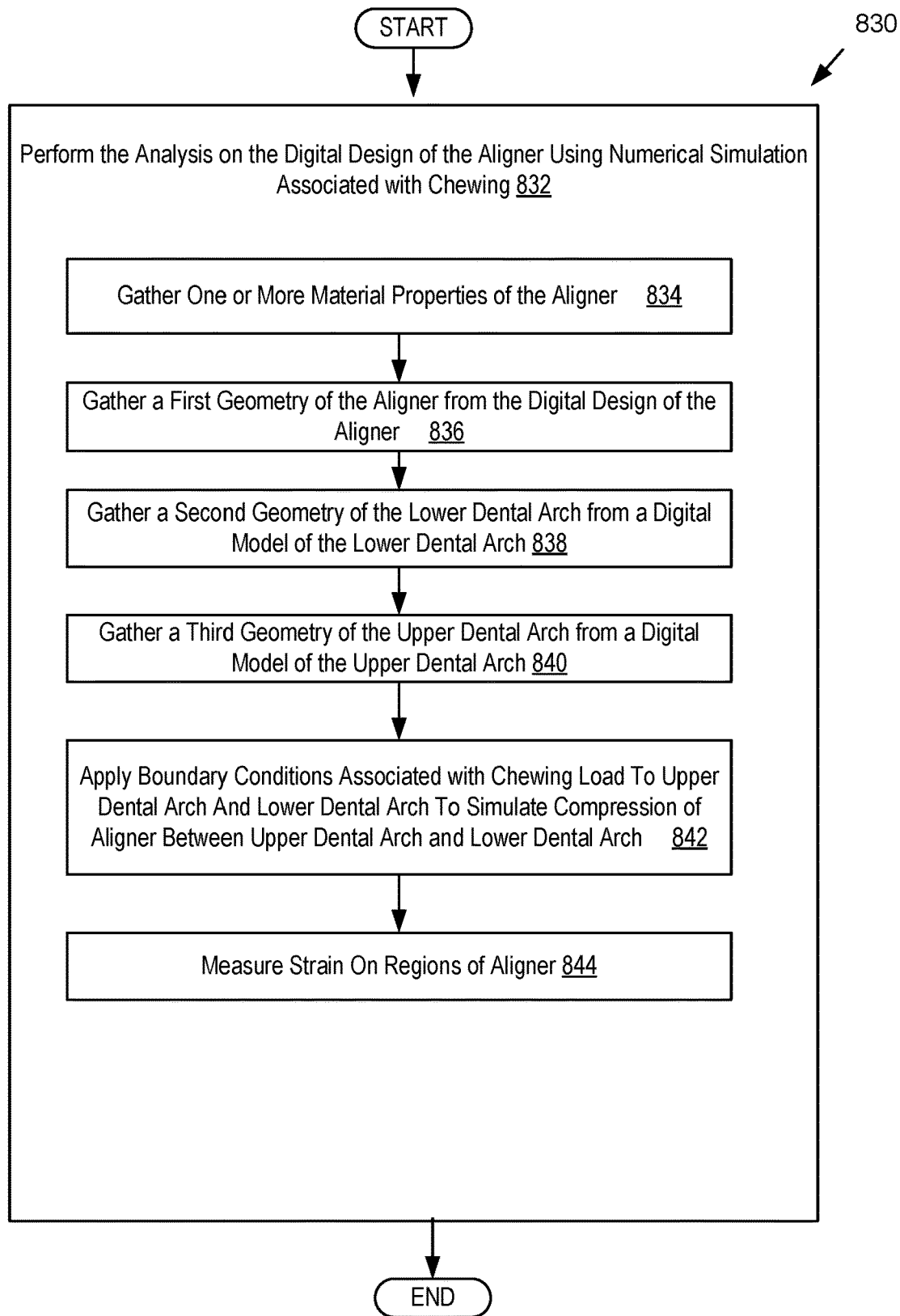
FIG. 8C illustrates a flow diagram for a method of performing analysis on a digital design of an aligner (e.g., a polymeric aligner) using numerical simulation associated with chewing and/or grinding of teeth, in accordance with one embodiment.

FIG. 8C illustrates a flow diagram for a method 830 of performing analysis on a digital design of an aligner (e.g., a polymeric aligner) using numerical simulation associated with chewing and/or grinding of teeth, in accordance with one embodiment. One or more operations of method 830 are performed by processing logic of a computing device. The processing logic may include hardware (e.g., circuitry, dedicated logic, programmable logic, microcode, etc.), software (e.g., instructions executed by a processing device), firmware, or a combination thereof. For example, one or more operations of method 830 may be performed by a processing device executing an aligner design analysis module 1450 of FIG. 14. It should be noted that the method 830 may be performed for each unique aligner for each patient's treatment plan, or for each unique aligner at key stages of the treatment plan. Further, method 830 includes operations that may be performed during block 104 of FIG. 1A.

At block 832, processing logic may perform the analysis on the digital design of the aligner using numerical simulation associated with chewing and/or tooth grinding. The numerical simulation may include finite element method, finite difference method, finite volume method, meshfree methods, smoothed-particle methods, combinations of these methods, or the like.

At block 834, processing logic may gather one or more material properties (also referred to as material property information) of the aligner. The material properties may include an amount or value of stress and/or strain that the material can sustain before cracking, breaking, deforming, warping, etc. One example of a material property of the material is the Young's Modulus of the material. In some embodiments, the material properties may not change between different digital designs of aligners because the aligners will be made of the same material (e.g., polymeric).

At block 836, processing logic may gather a first geometry of the aligner from the digital design of the aligner. In embodiments, this may include gathering the digital design of the aligner. The first geometry may be specific to each patient (and to each stage of treatment) and may be determined based on the dental arch of the patient. The first geometry may be obtained by generating the digital design of the aligner by manipulating a digital model of a dental arch-like structure (e.g., of a mold or dental arch of a patient). The digital model of the dental arch-like structure may represent the dental arch of the patient. The digital model of the dental arch-like structure may be offset to approximate a surface of the aligner and to generate the digital design of the aligner. As such, the digital design of the aligner may include cavities configured to receive teeth (referred to as tooth-receiving cavities or caps) of the patient and/or attachments on the teeth.

At block 838, processing logic may gather a second geometry of the dental arch-like structure from a digital model of the dental arch-like structure (e.g., mold). In embodiments, this may include gathering the digital model of the dental arch-like structure. The digital model of the dental arch-like structure may be generated from information obtained by performing an intraoral scan of the patient during a consultation and/or from a treatment plan. For example, the dental arch of the patient may be digitized, via scanning, and modeled as the dental arch used to fabricate the mold. The second geometry may include information related to the dental arch of the patient, such as the tooth size, tooth shape, tooth orientation, distance between teeth, attachments on teeth, upper dental arch, lower dental arch, etc. The dental arch-like structure may represent an upper dental arch or a lower dental arch of a patient at a stage of treatment.

At block 840, processing logic may additionally gather a third geometry of an opposing dental arch-like structure from a digital model of the opposing dental arch-like structure (e.g., mold). In embodiments, this may include gathering the digital model of the opposing dental arch-like structure. The digital model of the opposing dental arch-like structure may be generated from information obtained by performing an intraoral scan of the patient during a consultation and/or from a treatment plan. The third geometry may include information related to the opposing dental arch of the patient, such as the tooth size, tooth shape, tooth orientation, distance between teeth, attachments on teeth, upper dental arch, lower dental arch, etc. The opposing dental arch-like structure may represent an upper dental arch or a lower dental arch of a patient at a stage of treatment.

At block 842, processing logic may apply boundary conditions associated with a chewing load (or a tooth grinding load) to both the upper and lower dental arch of the patient (e.g., to the second geometry of the digital model of the dental arch-like structure and to the third geometry of the digital model of the opposing dental arch-like structure). In an embodiment, the boundary conditions for the upper dental arch is a fixed position (e.g., zero displacement), and the boundary conditions for the lower dental arch is application of a load (e.g., a force) to one or more points on the lower dental arch. In another embodiment, the boundary conditions for the lower dental arch is a fixed position (zero displacement) and the boundary conditions for the upper dental arch is application of a load to one or more points on the upper dental arch. These applied boundary conditions may simulate compression of the aligner between the upper dental arch and the lower dental arch. In embodiments, approximately 0-2000 Newtons of force may be applied to one dental arch in the direction of the opposing dental arch. Depending on the shape of the teeth, the size of the teeth, the heights of the teeth, patient gender, patient age, and so on, compressive forces, and thus strain, may be distributed unevenly across the various points of the aligner.

At block 844, processing logic may measure a strain on the various regions or points of the aligner. The strain may then be used to assess whether any points on the aligner are probable points of damage.

Figure 9:
FIG. 9 illustrates a flow diagram for a method for implementing one or more corrective actions to a polymeric aligner based on a simulated removal of the polymeric aligner from a dental arch.

FIG. 9 illustrates a flow diagram for a method 900 for implementing one or more corrective actions to an aligner (e.g., a polymeric aligner) based on a result one or more loads on the aligner. One or more operations of method 900 are performed by processing logic of a computing device. The processing logic may include hardware (e.g., circuitry, dedicated logic, programmable logic, microcode, etc.), software (e.g., instructions executed by a processing device), firmware, or a combination thereof. For example, one or more operations of method 900 may be performed by a processing device executing an aligner design analysis module 1450 of FIG. 14. It should be noted that the method 900 may be performed for each unique aligner for each patient's treatment plan, or for each unique aligner at key stages of the treatment plan. Further, method 900 includes operations that may be performed during block 104 of FIG. 1A.

At block 902, processing logic may simulate a load on the aligner using any of the techniques set forth herein above. For example, processing logic may simulate a removal of a polymeric aligner from a dental-arch like structure (e.g., mold or dental arch of a patient) using a first digital model and a second digital model. The first digital model represents a digital arch-like structure of a patient and the second digital model represents a polymeric aligner to be supported by the dental arch-like structure and specifies one or more physical properties of the polymeric aligner at one or more regions of the polymeric aligner.

At block 904, processing logic may determine a likeliness that one or more values at the one or more regions will satisfy one or more damage criteria. The values may represent a strain and/or stress or any other quantities derived from those quantities determined at the one or more regions during the simulated load on the aligner (e.g., during the simulated removal of the polymeric aligner from the dental arch using the first digital model and the second digital model). The damage criteria may be satisfied when the one or more values exceed a threshold value. The threshold value may have been determined based on a trained machine learning model based on breakage data, in one embodiment. The determination at block 904 may be based on an interaction of the dental arch-like structure and the one or more physical properties of the polymeric aligner, and the interaction being due to the simulated removal, in one embodiment.

At block 906, in response to analyzing the digital model of the aligner for one or more likely points of physical damage based on the determination of the likeliness of the one or more values satisfying the one or more damage criteria, processing logic may determine whether to implement one or more corrective actions for the aligner. If a determination is made to implement one or more corrective actions, processing logic may implement the one or more corrective actions on the aligner.

Figure 10:
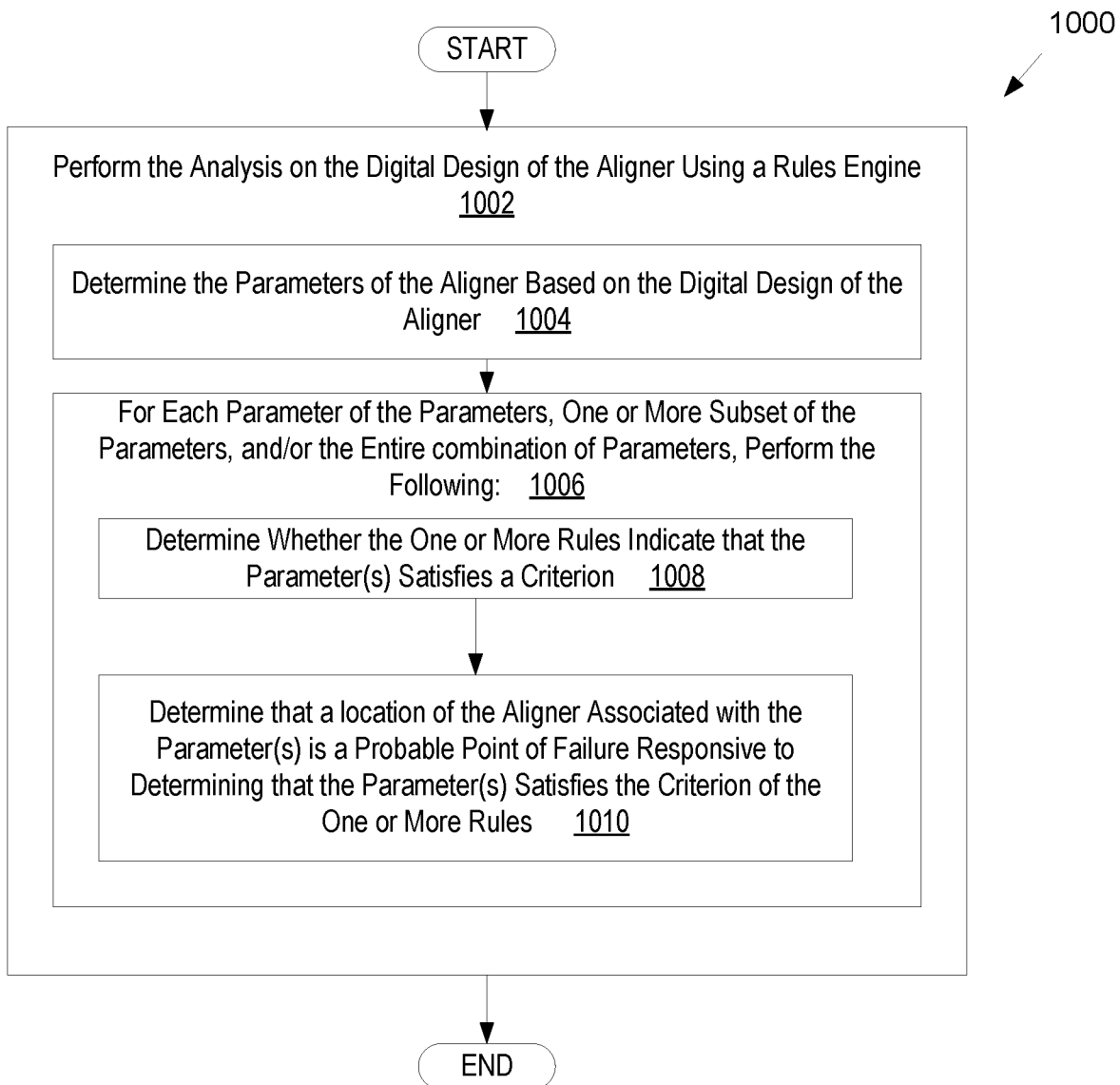
FIG. 10 illustrates a flow diagram for a method of performing analysis on a digital design of a polymeric aligner using a rules engine, in accordance with one embodiment.

FIG. 10 illustrates a flow diagram for a method 1000 of performing analysis on a digital design of an aligner (e.g., a polymeric aligner) using a rules engine, in accordance with one embodiment. One or more operations of method 1000 are performed by processing logic of a computing device. The processing logic may include hardware (e.g., circuitry, dedicated logic, programmable logic, microcode, etc.), software (e.g., instructions executed by a processing device), firmware, or a combination thereof. For example, one or more operations of method 1000 may be performed by a processing device executing an aligner design analysis module 1450 of FIG. 14. It should be noted that the method 1000 may be performed for each unique aligner for each patient's treatment plan, or for each unique aligner at key stages of the treatment plan. Further, method 1000 includes operations that may be performed during block 104 of FIG. 1A.

The rules engine may use one or more rules that are determined based on observations, output of numerical simulation, or the like. For example, customers may provide reports that describe an aligner that broke during removal, manufacturing technician may observe aligner breakage during removal of the aligners from molds, and so forth. Hundreds or thousands of observations of aligners that broke as a result of force being applied may be used to determine patterns or combinations of features included in the broken aligners that may have caused the breakage. The rules may be determined that specify there is a probable point of damage when the patterns or combinations of features are present in subsequent designs. Further, the numerical simulation may be executed and identify probable points of damage as output. The output from hundreds or thousands of numerical simulations may be aggregated and patterns or combinations of features may be identified that are associated with the probable points of damage. The rules may be determined that specify there is a probable point of damage when the patterns or combinations of features are present in subsequent designs.

At block 1002, processing logic may perform the analysis on the digital design of the aligner using a rules engine including one or more rules associated with parameters of the aligners indicative of points of damage, which may include performing operations at blocks 1004 and 1006. The rules may include rules associated with sets of parameters (e.g., multiple features within a threshold proximity with one another) and/or with individual parameters. At block 1004, processing logic may determine the parameters of the aligner based on the digital design of the polymeric aligner. The parameters may include at least one of an angle of a cutline at locations of the aligner associated with an interproximal region of the dental arch of the patient, a curvature of the aligner, a thickness of the aligner, an undercut height associated with an attachment of a tooth of the tooth of the dental arch of the patient, whether features are present in the aligner, a distance between features of the aligner associated with attachments of teeth of the dental arch of the patient, a number of the features of the aligner, and/or a combination of the features of the aligner. Any one or more of these parameters may be indicative of a probable point of damage in the digital design of the aligner as determined from historical patient feedback, the trained machine learning model, and/or running any of the numerical simulations described above. The rules may be created based on one or more of the parameters.

At block 1006, for each parameter of the parameters, processing logic may perform operations at blocks 1008 and 1010. Processing logic may additionally perform the operations at blocks 1008 and 1010 based on one or more combinations of parameters and/or based on all of the identified parameters. At block 1008, processing logic may determine whether the one or more rules indicate that the parameter (or set of parameters) satisfies a criterion. The criterion may relate to a threshold value being exceeded by the parameter or a presence of certain features indicated by the parameter or parameters. For example, if there is an attachment on a certain tooth and another attachment on a neighboring tooth, the rule may indicate there is a probable point of damage between the two teeth. In another example, if an angle of a cutline is more than a threshold angle, the rule may indicate there is a probable point of damage at the location of the cutline. Rules may also be associated with particular teeth. For example, different threshold angles for the cutline may be associated with interproximal regions between different pairs of teeth.

Accordingly, at block 1010, processing logic may determine that a location of the digital design of the aligner associated with the parameter is a probable point of damage responsive to determining that the parameter satisfies the criteria of the one or more rules. One or more corrective actions may be performed in response to determining that there is a probable point of damage. In some embodiments, the digital design of the aligner may be input into the trained machine learning model to verify the probable point of damage, any of the numerical simulations described above may be performed on the digital design of the aligner, or both.

Figure 11:
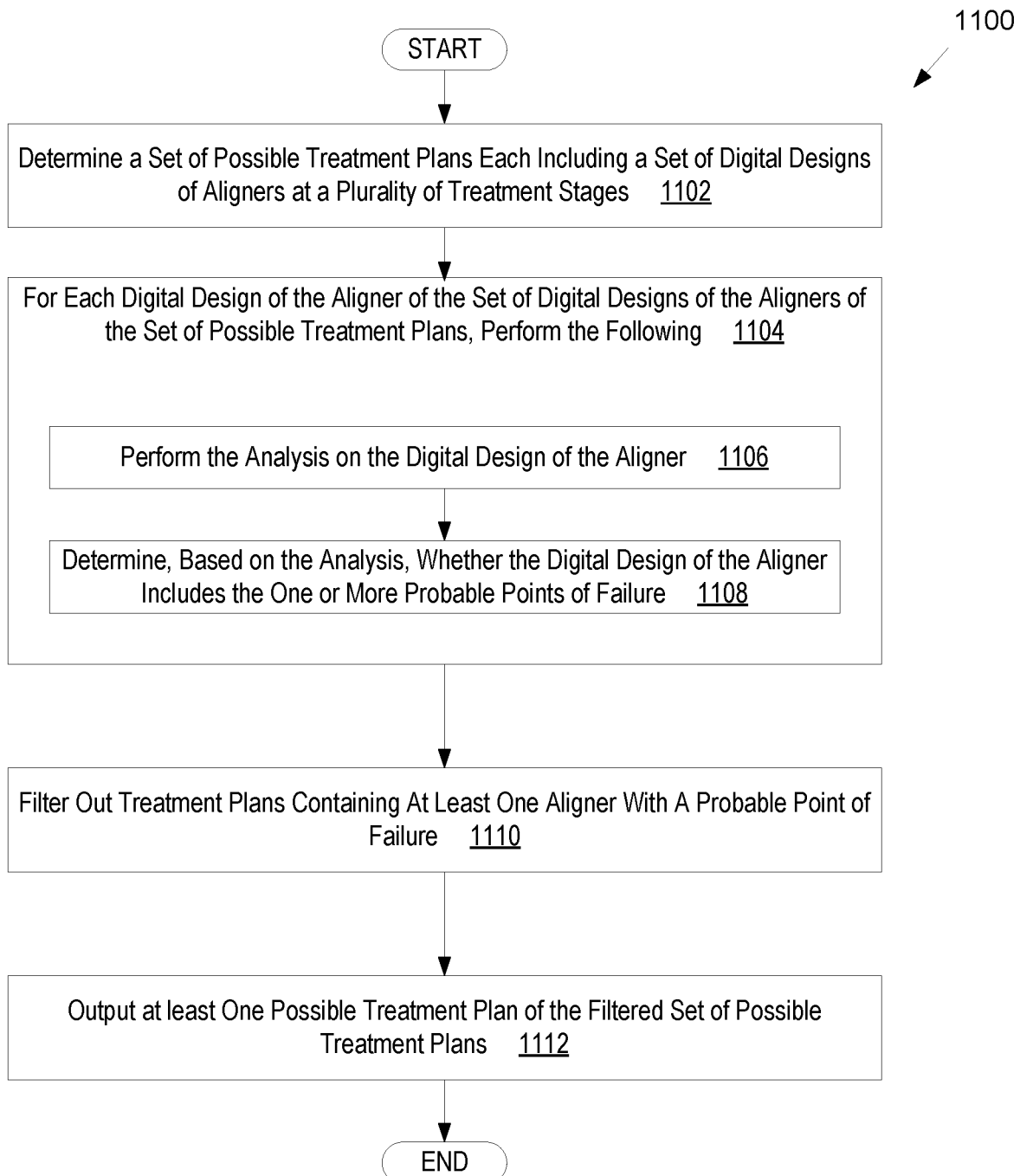
FIG. 11 illustrates a flow diagram for a method of outputting a filtered set of possible treatment plans, in accordance with one embodiment.

FIG. 11 illustrates a flow diagram for a method 1100 of outputting a filtered set of possible treatment plans, in accordance with one embodiment. One or more operations of method 1100 are performed by processing logic of a computing device. The processing logic may include hardware (e.g., circuitry, dedicated logic, programmable logic, microcode, etc.), software (e.g., instructions executed by a processing device), firmware, or a combination thereof. For example, one or more operations of method 1100 may be performed by a processing device executing an aligner design analysis module 1450 of FIG. 14.

At block 1102, processing logic may determine a set of possible treatment plans each including a set of digital designs of aligners (e.g., polymeric aligners) at a set of treatment stages. The set of possible treatment plans may include treatment plans that are dynamically generated based on an intraoral scan of the mouth of the patient, provided by a doctor, modified by the doctor (e.g., the doctor adds an attachment to a tooth at a particular stage), and so forth.

At block 1104, for each digital design of the aligner of the set of digital designs of the aligners of the set of possible treatment plans, processing logic may perform operations at block 1106 and 1108. At block 1106, processing logic may perform the analysis on the digital design of the aligner. The analysis may include using at least one of a) the trained machine learning model, b) any one or more of the numerical simulations, or c) the rules engine. In some embodiments, the analysis may include using the rules engine to identify a probable point of damage and then inputting the digital design of the aligner into the trained machine learning model and/or running any of the numerical simulations described above on the digital design of the aligner to verify the probable point of damage. In another embodiment, the digital design of the aligner may be input into the trained machine learning model which may output an existence of a probable point of damage in the digital design of the aligner (and optionally a location of the probable point of damage), and the numerical simulation may be performed on the digital design of the aligner to verify the existence and/or location of a probable point of damage. In another embodiment, any one or more numerical simulations described above may be performed on the digital design of the aligner to determine that there is a probable point of damage, and the digital design of the aligner may be input into the trained machine learning model to verify the probable point of damage.

At block 1108, processing logic may determine, based on the analysis, whether the digital design of the aligner includes the one or more probable points of damage.

At block 1110, processing logic may filter out treatment plans associated with digital designs of one or more aligners that have probable points of damages from the set of possible treatment plans to create a filtered set of possible treatment plans.

At block 1112, processing logic may output at least one possible treatment plan of the filtered set of possible treatment plans. The filtered set of possible treatment plans may lack digital designs of aligners having probable points of damage. In some embodiments, if the probable points of damage cannot be resolved, notifications may be provided to the doctor that one or more of the digital designs of the aligners includes a probable point of damage and recommend the doctor provide instructions on how to properly remove the aligner to lower the chance of damage, move including an attachment on one tooth to a later stage in the treatment plan, or the like.

Figure 12:
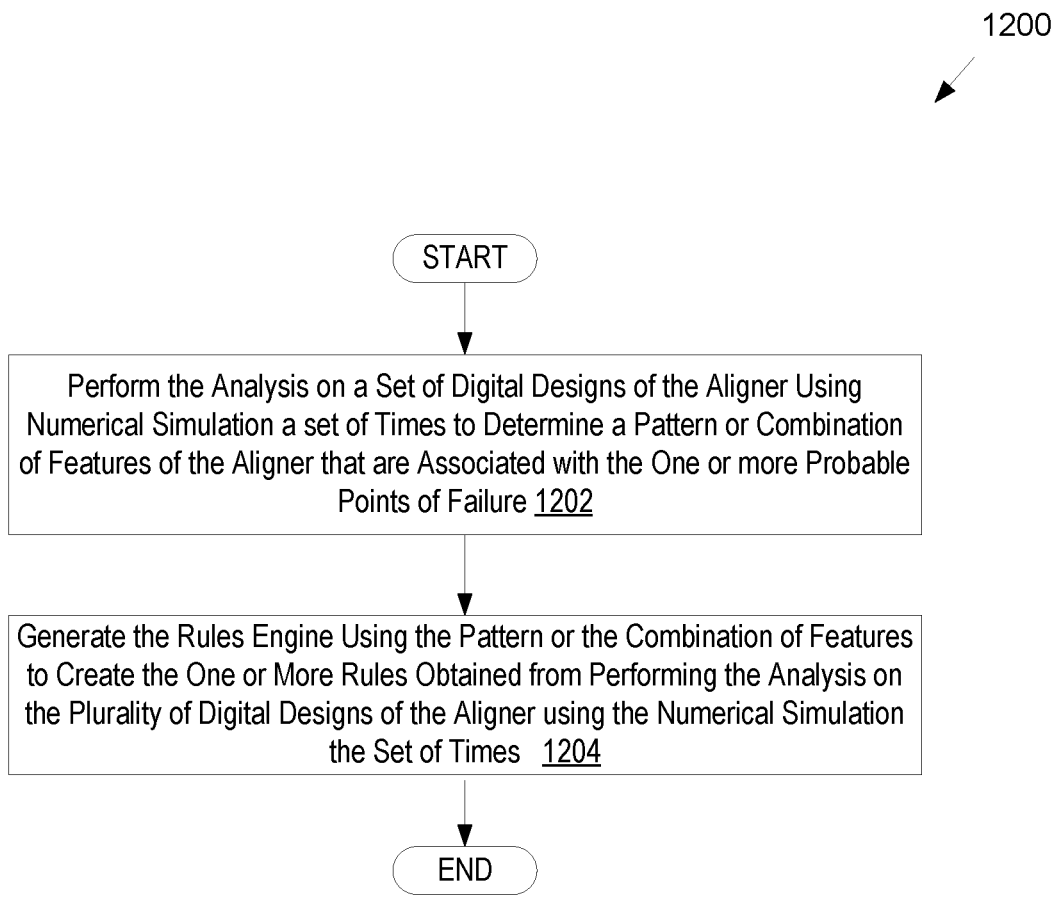
FIG. 12 illustrates a flow diagram for a method of performing numerical simulation on digital designs of a polymeric aligner to generate rules for a rules engine, in accordance with one embodiment.

FIG. 12 illustrates a flow diagram for a method 1200 of performing numerical simulation on digital designs of an aligner (e.g., a polymeric aligner) to generate a rules engine, in accordance with one embodiment. One or more operations of method 1200 are performed by processing logic of a computing device. The processing logic may include hardware (e.g., circuitry, dedicated logic, programmable logic, microcode, etc.), software (e.g., instructions executed by a processing device), firmware, or a combination thereof. For example, one or more operations of method 1200 may be performed by a processing device executing an aligner design analysis module 1450 of FIG. 14.

At block 1202, processing logic may perform the analysis on a set of digital designs of the aligner using any of the numerical simulations described above multiple times to determine a pattern or combination of features or parameters of the aligner that are associated with the one or more probable points of damage. The pattern or combination of features or parameters may include attachments being too crowded, teeth being too crowded, a outline angle exceeding a threshold value, a thickness of the aligner being too thin, etc.

At block 1204, processing logic may generate the rules engine using the pattern or the combination of features or parameters to create the one or more rules obtained from performing the analysis on the set of digital designs of the aligner using the numerical simulation multiple times. In some embodiments, once the rules engine is generated, the digital designs of the aligners may be processed by the rules engine prior to having any numerical simulations performed or being input into the trained machine learning model. If the rules engine indicates there is a probable point of damage included in a digital design of the aligner, further analysis may perform numerical simulation on the digital design of the aligner and/or inputting the digital design of the aligner into the trained machine learning model.

Figure 13:
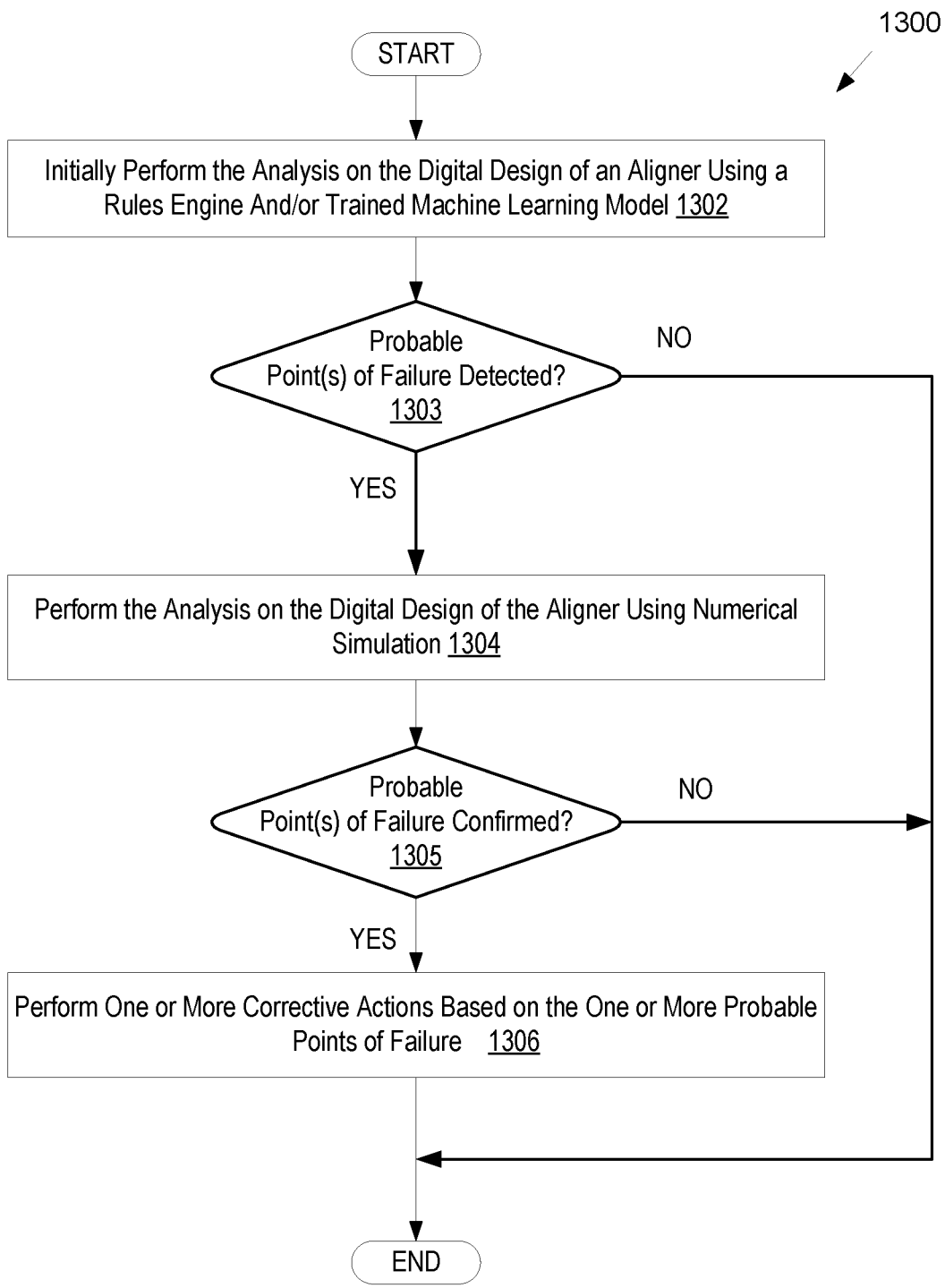
FIG. 13 illustrates a flow diagram for a method of using a rules engine on a digital design of a polymeric aligner to identify a probable point of damage and then performing a numerical simulation of the digital design of the polymeric aligner, in accordance with one embodiment.

FIG. 13 illustrates a flow diagram for a method 1300 of using a rules engine and/or a trained machine learning model on a digital design of an aligner (e.g., a polymeric aligner) to identify a probable point of damage and then performing a numerical simulation of the digital design of the aligner, in accordance with one embodiment. One or more operations of method 1300 are performed by processing logic of a computing device. The processing logic may include hardware (e.g., circuitry, dedicated logic, programmable logic, microcode, etc.), software (e.g., instructions executed by a processing device), firmware, or a combination thereof. For example, one or more operations of method 1300 may be performed by a processing device executing an aligner design analysis module 1450 of FIG. 14.

At block 1302, processing logic may perform the analysis on the digital design of the aligner using the rules engine including the one or more rules associated with the parameters of the aligners indicative of the points of damage without performing the numerical simulation. The rules engine may indicate that there is a probable point of damage included in the digital design of the aligner based on the parameters of the digital design of the aligner.

At block 1303, processing logic may determine whether there are one or more probable points of damage detected using the rules engine and/or the trained machine learning model. If there is not one or more probable point of damage detected in the aligner, the method 1300 may conclude. If there is one or more probable point of damage detected in the aligner, at block 1304, processing logic may perform the analysis on the digital design of the aligner using the numerical simulation to confirm that there are one or more probable points of damage included in the aligner.

At block 1305, processing logic may determine whether there is one or more probable points confirmed using the numerical simulation. If not, the method 1300 may conclude. If the processing logic confirms there are one or more probable points of damage using the numerical simulation, at block 1306, processing logic may perform one or more corrective actions based on the one or more probable points of damage.

FIG. 14 illustrates a diagrammatic representation of a machine in the example form of a computing device 1400 within which a set of instructions, for causing the machine to perform any one or more of the methodologies discussed herein (e.g., the methods of FIGS. 1-13). In some embodiments, the machine may be part of a design station or communicatively coupled to the design station. In alternative embodiments, the machine may be connected (e.g., networked) to other machines in a Local Area Network (LAN), an intranet, an extranet, or the Internet. For example, the machine may be networked to the design station and/or a rapid prototyping apparatus such as a 3D printer or SLA apparatus. The machine may operate in the capacity of a server or a client machine in a client-server network environment, or as a peer machine in a peer-to-peer (or distributed) network environment. The machine may be a personal computer (PC), a tablet computer, a set-top box (STB), a Personal Digital Assistant (PDA), a cellular telephone, a web appliance, a server, a network router, switch or bridge, or any machine capable of executing a set of instructions (sequential or otherwise) that specify actions to be taken by that machine. Further, while only a single machine is illustrated, the term "machine" shall also be taken to include any collection of machines (e.g., computers) that individually or jointly execute a set (or multiple sets) of instructions to perform any one or more of the methodologies discussed herein.

The example computer device 1400 (also referred to as a computing device) includes a processing device 1402, a main memory 1404 (e.g., read-only memory (ROM), flash memory, dynamic random access memory (DRAM) such as synchronous DRAM (SDRAM), etc.), a static memory 1406 (e.g., flash memory, static random access memory (SRAM), etc.), and a secondary memory (e.g., a data storage device 1428), which communicate with each other via a bus 1408.

Processing device 1402 represents one or more general-purpose processors such as a microprocessor, central processing unit, or the like. More particularly, the processing device 1402 may be a complex instruction set computing (CISC) microprocessor, reduced instruction set computing (RISC) microprocessor, very long instruction word (VLIW) microprocessor, processor implementing other instruction sets, or processors implementing a combination of instruction sets. Processing device 1402 may also be one or more special-purpose processing devices such as an application specific integrated circuit (ASIC), a field programmable gate array (FPGA), a digital signal processor (DSP), network processor, or the like. Processing device 1402 is configured to execute the processing logic (instructions 1426) for performing operations and steps discussed herein.

The computing device 1400 may further include a network interface device 1422 for communicating with a network 1464. The computing device 1400 also may include a video display unit 1410 (e.g., a liquid crystal display (LCD) or a cathode ray tube (CRT)), an alphanumeric input device 1412 (e.g., a keyboard), a cursor control device 1414 (e.g., a mouse), and a signal generation device 1420 (e.g., a speaker).

The data storage device 1428 may include a machine-readable storage medium (or more specifically a non-transitory computer-readable storage medium) 1424 on which is stored one or more sets of instructions 1426 embodying any one or more of the methodologies or functions described herein. A non-transitory storage medium refers to a storage medium other than a carrier wave. The instructions 1426 may also reside, completely or at least partially, within the main memory 1404 and/or within the processing device 1402 during execution thereof by the computer device 1400, the main memory 1404 and the processing device 1402 also constituting computer-readable storage media.

The computer-readable storage medium 1424 may also be used to store one or more digital models of aligners and/or dental arches (also referred to as electronic models) and/or an aligner design analysis module 1450, which may perform one or more of the operations of the methods described herein. The computer-readable storage medium 1424 may also store a software library containing methods that call an aligner design analysis module 1450. While the computer-readable storage medium 1424 is shown in an example embodiment to be a single medium, the term "computer-readable storage medium" should be taken to include a single medium or multiple media (e.g., a centralized or distributed database, and/or associated caches and servers) that store the one or more sets of instructions. The term "computer-readable storage medium" shall also be taken to include any medium that is capable of storing or encoding a set of instructions for execution by the machine and that cause the machine to perform any one or more of the methodologies of the present disclosure. The term "computer-readable storage medium" shall accordingly be taken to include, but not be limited to, solid-state memories, and optical and magnetic media.

FIG. 15A illustrates an exemplary tooth repositioning appliance or aligner 1500 that can be worn by a patient in order to achieve an incremental repositioning of individual teeth 1502 in the jaw. The appliance can include a shell (e.g., a continuous polymeric shell or a segmented shell) having teeth-receiving cavities that receive and resiliently reposition the teeth. An appliance or portion(s) thereof may be indirectly fabricated using a physical model of teeth. For example, an appliance (e.g., polymeric appliance) can be formed using a physical model of teeth and a sheet of suitable layers of polymeric material. A "polymeric material," as used herein, may include any material formed from a polymer. A "polymer," as used herein, may refer to a molecule composed of repeating structural units connected by covalent chemical bonds often characterized by a substantial number of repeating units (e.g., equal to or greater than 3 repeating units, optionally, in some embodiments equal to or greater than 10 repeating units, in some embodiments greater or equal to 30 repeating units) and a high molecular weight (e.g. greater than or equal to 10,000 Da, in some embodiments greater than or equal to 50,000 Da or greater than or equal to 100,000 Da). Polymers are commonly the polymerization product of one or more monomer precursors. The term polymer includes homopolymers, or polymers consisting essentially of a single repeating monomer subunit. The term polymer also includes copolymers which are formed when two or more different types of monomers are linked in the same polymer. Useful polymers include organic polymers or inorganic polymers that may be in amorphous, semi-amorphous, crystalline or semi-crystalline states. Polymers may include polyolefins, polyesters, polyacrylates, polymethacrylates, polystyrenes, Polypropylenes, polyethylenes, Polyethylene terephthalates, poly lactic acid, polyurethanes, epoxide polymers, polyethers, poly (vinyl chlorides), polysiloxanes, polycarbonates, polyamides, poly acrylonitriles, polybutadienes, poly(cycloolefins), and copolymers. The systems and/or methods provided herein are compatible with a range of plastics and/or polymers. Accordingly, this list is not all inclusive, but rather is exemplary. The plastics can be thermosets or thermoplastics. The plastic may be a thermoplastic.

Examples of materials applicable to the embodiments disclosed herein include, but are not limited to, those materials described in the following published and provisional patent applications filed by Align Technology: "MULTI-MATERIAL ALIGNERS," US Publication No. 2017/0007361 published Jan. 12, 2017; "DIRECT FABRICATION OF ALIGNERS WITH INTERPROXIMAL FORCE COUPLING", US Publication No. 2017/0007365 published Jan. 12, 2017; "DIRECT FABRICATION OF ORTHODONTIC APPLIANCES WITH VARIABLE PROPERTIES," US Publication No. 2017/0007359 published Jan. 12, 2017; "DIRECT FABRICATION OF ALIGNERS FOR ARCH EXPANSION", US Publication No. 2017/0007366 published Jan. 12, 2017; "DIRECT FABRICATION OF ATTACHMENT TEMPLATES WITH ADHESIVE," US Publication No. 2017/0007368 published Jan. 12, 2017; "DIRECT FABRICATION OF ALIGNERS FOR PALATE EXPANSION AND OTHER APPLICATIONS", US Publication No. 2017/0007367 published Jan. 12, 2017; "SYSTEMS, APPARATUSES AND METHODS FOR DENTAL APPLIANCES WITH INTEGRALLY FORMED FEATURES", US Publication No. 2017/0007360 published Jan. 12, 2017; "DIRECT FABRICATION OF POWER ARMS", US Publication No. 2017/0007363 published Jan. 12, 2017; "SYSTEMS, APPARATUSES AND METHODS FOR SUBSTANCE DELIVERY FROM DENTAL APPLIANCE", US Publication No. 2017/0007386 published Jan. 12, 2017; "DENTAL APPLIANCE HAVING ORNAMENTAL DESIGN", US Publication No. 2017/0008333 published Jan. 12, 2017; "DENTAL MATERIALS USING THERMOSET POLYMERS," US Publication No. 2017/0007362 published Jan. 12, 2017; "CURABLE COMPOSITION FOR USE IN A HIGH TEMPERATURE LITHOGRAPHY-BASED PHOTOPOLYMERIZATION PROCESS AND METHOD OF PRODUCING CROSSLINKED POLYMERS THEREFROM," U.S. Provisional Application Ser. No. 62/667,354, filed May 4, 2018; "POLYMERIZABLE MONOMERS AND METHOD OF POLYMERIZING THE SAME," U.S. Provisional Application Ser. No. 62/667,364, filed May 4, 2018; and any conversion applications thereof (including publications and issued patents), including any divisional, continuation, or continuation-in-part thereof.

Although polymeric aligners are discussed herein, the techniques disclosed may also be applied to aligners having different materials. Some embodiments are discussed herein with reference to orthodontic aligners (also referred to simply as aligners). However, embodiments also extend to other types of shells formed over molds, such as orthodontic retainers, orthodontic splints, sleep appliances for mouth insertion (e.g., for minimizing snoring, sleep apnea, etc.) and/or shells for non-dental applications. Accordingly, it should be understood that embodiments herein that refer to aligners also apply to other types of shells. For example, the principles, features and methods discussed may be applied to any application or process in which it is useful to perform image based quality control for any suitable type of shells that are form fitting devices such as eye glass frames, contact or glass lenses, hearing aids or plugs, artificial knee caps, prosthetic limbs and devices, orthopedic inserts, as well as protective equipment such as knee guards, athletic cups, or elbow, chin, and shin guards and other like athletic/protective devices.

The aligner 1500 can fit over all teeth present in an upper or lower jaw, or less than all of the teeth. The appliance can be designed specifically to accommodate the teeth of the patient (e.g., the topography of the tooth-receiving cavities matches the topography of the patient's teeth), and may be fabricated based on positive or negative models of the patient's teeth generated by impression, scanning, and the like. Alternatively, the appliance can be a generic appliance configured to receive the teeth, but not necessarily shaped to match the topography of the patient's teeth. In some cases, only certain teeth received by an appliance will be repositioned by the appliance while other teeth can provide a base or anchor region for holding the appliance in place as it applies force against the tooth or teeth targeted for repositioning. In some cases, some, most, or even all of the teeth will be repositioned at some point during treatment. Teeth that are moved can also serve as a base or anchor for holding the appliance as it is worn by the patient. Typically, no wires or other means will be provided for holding an appliance in place over the teeth. In some cases, however, it may be desirable or necessary to provide individual attachments or other anchoring elements 1504 on teeth 1502 with corresponding receptacles or apertures 1506 in the aligner 1500 so that the appliance can apply a selected force on the tooth. Exemplary appliances, including those utilized in the Invisalign® System, are described in numerous patents and patent applications assigned to Align Technology, Inc. including, for example, in U.S. Pat. Nos. 6,450,807, and 5,975,893, as well as on the company's website, which is accessible on the World Wide Web (see, e.g., the url "invisalign.com"). Examples of tooth-mounted attachments suitable for use with orthodontic appliances are also described in patents and patent applications assigned to Align Technology, Inc., including, for example, U.S. Pat. Nos. 6,309,215 and 6,830,450.

Figure 15B:
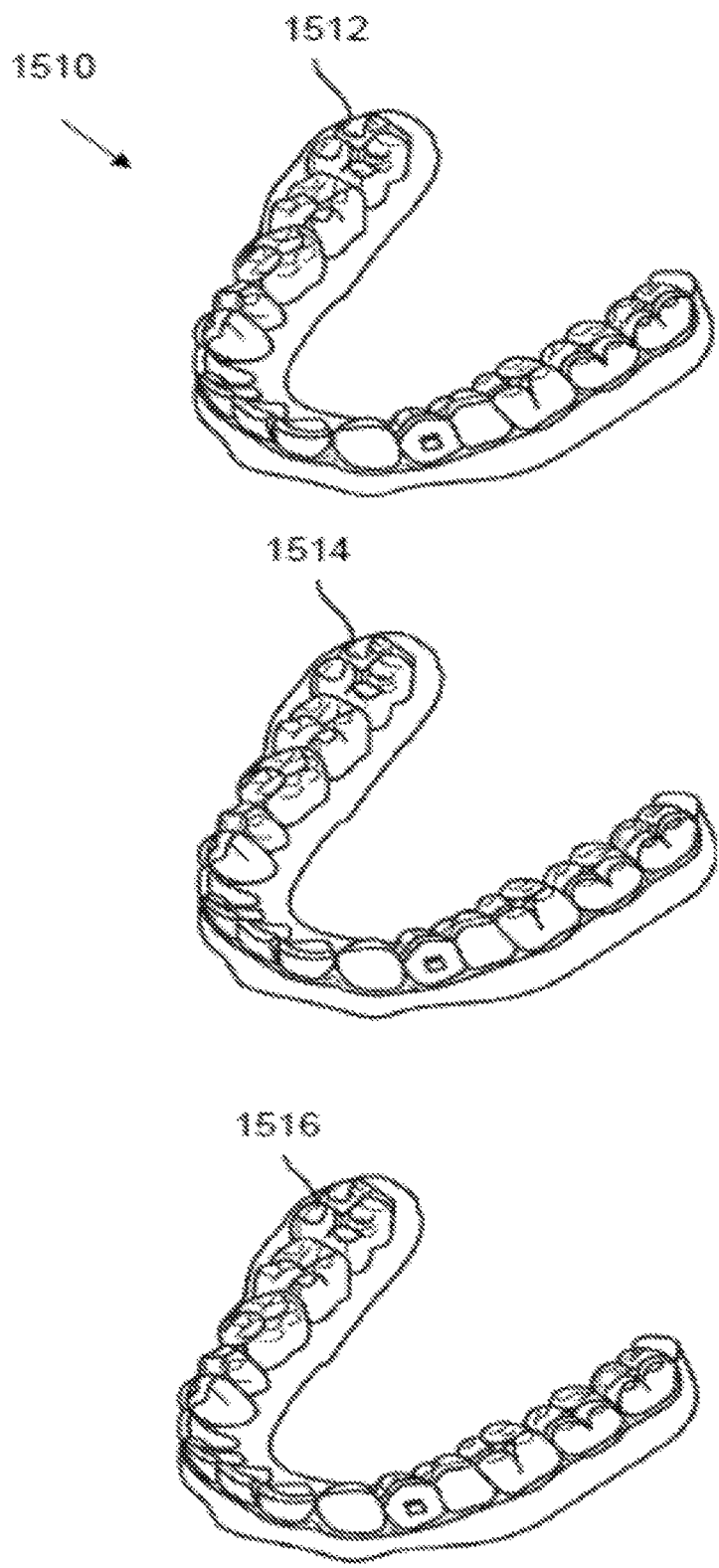
FIG. 15B illustrates a tooth repositioning system, in accordance with embodiments.

FIG. 15B illustrates a tooth repositioning system 1510 including a plurality of appliances 1512, 1514, 1516. Any of the appliances described herein can be designed and/or provided as part of a set of a plurality of appliances used in a tooth repositioning system. Each appliance may be configured so a tooth-receiving cavity has a geometry corresponding to an intermediate or final tooth arrangement intended for the appliance. The patient's teeth can be progressively repositioned from an initial tooth arrangement to a target tooth arrangement by placing a series of incremental position adjustment appliances over the patient's teeth. For example, the tooth repositioning system 1510 can include a first appliance 1512 corresponding to an initial tooth arrangement, one or more intermediate appliances 1514 corresponding to one or more intermediate arrangements, and a final appliance 1516 corresponding to a target arrangement. A target tooth arrangement can be a planned final tooth arrangement selected for the patient's teeth at the end of all planned orthodontic treatment. Alternatively, a target arrangement can be one of some intermediate arrangements for the patient's teeth during the course of orthodontic treatment, which may include various different treatment scenarios, including, but not limited to, instances where surgery is recommended, where interproximal reduction (IPR) is appropriate, where a progress check is scheduled, where anchor placement is best, where palatal expansion is desirable, where restorative dentistry is involved (e.g., inlays, onlays, crowns, bridges, implants, veneers, and the like), etc. As such, it is understood that a target tooth arrangement can be any planned resulting arrangement for the patient's teeth that follows one or more incremental repositioning stages. Likewise, an initial tooth arrangement can be any initial arrangement for the patient's teeth that is followed by one or more incremental repositioning stages.

In some embodiments, the appliances 1512, 1514, 1516 (or portions thereof) can be produced using indirect fabrication techniques, such as by thermoforming over a positive or negative mold. Indirect fabrication of an orthodontic appliance can involve producing a positive or negative mold of the patient's dentition in a target arrangement (e.g., by rapid prototyping, milling, etc.) and thermoforming one or more sheets of material over the mold in order to generate an appliance shell.

In an example of indirect fabrication, a mold of a patient's dental arch may be fabricated from a digital model of the dental arch, and a shell may be formed over the mold (e.g., by thermoforming a polymeric sheet over the mold of the dental arch and then trimming the thermoformed polymeric sheet). The fabrication of the mold may be performed by a rapid prototyping machine (e.g., a stereolithography (SLA) 3D printer). The rapid prototyping machine may receive digital models of molds of dental arches and/or digital models of the appliances 1512, 1514, 1516 after the digital models of the appliances 1512, 1514, 1516 have been processed by processing logic of a computing device, such as the computing device in FIG. 14. The processing logic may include hardware (e.g., circuitry, dedicated logic, programmable logic, microcode, etc.), software (e.g., instructions executed by a processing device), firmware, or a combination thereof. For example, one or more operations may be performed by a processing device executing an appliance design analysis program or module 1450.

To manufacture the molds, a shape of a dental arch for a patient at a treatment stage is determined based on a treatment plan. In the example of orthodontics, the treatment plan may be generated based on an intraoral scan of a dental arch to be modeled. The intraoral scan of the patient's dental arch may be performed to generate a three dimensional (3D) virtual model of the patient's dental arch (mold). For example, a full scan of the mandibular and/or maxillary arches of a patient may be performed to generate 3D virtual models thereof. The intraoral scan may be performed by creating multiple overlapping intraoral images from different scanning stations and then stitching together the intraoral images to provide a composite 3D virtual model. In other applications, virtual 3D models may also be generated based on scans of an object to be modeled or based on use of computer aided drafting techniques (e.g., to design the virtual 3D mold). Alternatively, an initial negative mold may be generated from an actual object to be modeled (e.g., a dental impression or the like). The negative mold may then be scanned to determine a shape of a positive mold that will be produced.

Once the virtual 3D model of the patient's dental arch is generated, a dental practitioner may determine a desired treatment outcome, which includes final positions and orientations for the patient's teeth. Processing logic may then determine a number of treatment stages to cause the teeth to progress from starting positions and orientations to the target final positions and orientations. The shape of the final virtual 3D model and each intermediate virtual 3D model may be determined by computing the progression of tooth movement throughout orthodontic treatment from initial tooth placement and orientation to final corrected tooth placement and orientation. For each treatment stage, a separate virtual 3D model of the patient's dental arch at that treatment stage may be generated. The shape of each virtual 3D model will be different. The original virtual 3D model, the final virtual 3D model and each intermediate virtual 3D model is unique and customized to the patient.

Accordingly, multiple different virtual 3D models (digital designs) of a dental arch may be generated for a single patient. A first virtual 3D model may be a unique model of a patient's dental arch and/or teeth as they presently exist, and a final virtual 3D model may be a model of the patient's dental arch and/or teeth after correction of one or more teeth and/or a jaw. Multiple intermediate virtual 3D models may be modeled, each of which may be incrementally different from previous virtual 3D models.

Each virtual 3D model of a patient's dental arch may be used to generate a unique customized physical mold of the dental arch at a particular stage of treatment. The shape of the mold may be at least in part based on the shape of the virtual 3D model for that treatment stage. The virtual 3D model may be represented in a file such as a computer aided drafting (CAD) file or a 3D printable file such as a stereolithography (STL) file. The virtual 3D model for the mold may be sent to a third party (e.g., clinician office, laboratory, manufacturing facility or other entity). The virtual 3D model may include instructions that will control a fabrication system or device in order to produce the mold with specified geometries.

A clinician office, laboratory, manufacturing facility or other entity may receive the virtual 3D model of the mold, the digital model having been created as set forth above. The entity may input the digital model into a rapid prototyping machine. The rapid prototyping machine then manufactures the mold using the digital model. One example of a rapid prototyping manufacturing machine is a 3D printer. 3D printing includes any layer-based additive manufacturing processes. 3D printing may be achieved using an additive process, where successive layers of material are formed in proscribed shapes. 3D printing may be performed using extrusion deposition, granular materials binding, lamination, photopolymerization, continuous liquid interface production (CLIP), or other techniques. 3D printing may also be achieved using a subtractive process, such as milling.

In some instances, stereolithography (SLA), also known as optical fabrication solid imaging, is used to fabricate an SLA mold. In SLA, the mold is fabricated by successively printing thin layers of a photo-curable material (e.g., a polymeric resin) on top of one another. A platform rests in a bath of a liquid photopolymer or resin just below a surface of the bath. A light source (e.g., an ultraviolet laser) traces a pattern over the platform, curing the photopolymer where the light source is directed, to form a first layer of the mold. The platform is lowered incrementally, and the light source traces a new pattern over the platform to form another layer of the mold at each increment. This process repeats until the mold is completely fabricated. Once all of the layers of the mold are formed, the mold may be cleaned and cured.

Materials such as a polyester, a co-polyester, a polycarbonate, a polycarbonate, a thermopolymeric polyurethane, a polypropylene, a polyethylene, a polypropylene and polyethylene copolymer, an acrylic, a cyclic block copolymer, a polyetheretherketone, a polyamide, a polyethylene terephthalate, a polybutylene terephthalate, a polyetherimide, a polyethersulfone, a polytrimethylene terephthalate, a styrenic block copolymer (SBC), a silicone rubber, an elastomeric alloy, a thermopolymeric elastomer (TPE), a thermopolymeric vulcanizate (TPV) elastomer, a polyurethane elastomer, a block copolymer elastomer, a polyolefin blend elastomer, a thermopolymeric co-polyester elastomer, a thermopolymeric polyamide elastomer, or combinations thereof, may be used to directly form the mold. The materials used for fabrication of the mold can be provided in an uncured form (e.g., as a liquid, resin, powder, etc.) and can be cured (e.g., by photopolymerization, light curing, gas curing, laser curing, crosslinking, etc.). The properties of the material before curing may differ from the properties of the material after curing.

Appliances may be formed from each mold and when applied to the teeth of the patient, may provide forces to move the patient's teeth as dictated by the treatment plan. The shape of each appliance is unique and customized for a particular patient and a particular treatment stage. In an example, the appliances 1512, 1514, 1516 can be pressure formed or thermoformed over the molds. Each mold may be used to fabricate an appliance that will apply forces to the patient's teeth at a particular stage of the orthodontic treatment. The appliances 1512, 1514, 1516 each have teeth-receiving cavities that receive and resiliently reposition the teeth in accordance with a particular treatment stage.

In one embodiment, a sheet of material is pressure formed or thermoformed over the mold. The sheet may be, for example, a sheet of polymeric (e.g., an elastic thermopolymeric, a sheet of polymeric material, etc.). To thermoform the shell over the mold, the sheet of material may be heated to a temperature at which the sheet becomes pliable. Pressure may concurrently be applied to the sheet to form the now pliable sheet around the mold. Once the sheet cools, it will have a shape that conforms to the mold. In one embodiment, a release agent (e.g., a non-stick material) is applied to the mold before forming the shell. This may facilitate later removal of the mold from the shell. Forces may be applied to lift the appliance from the mold. In some instances, a breakage, warpage, or deformation may result from the removal forces. Accordingly, embodiments disclosed herein may determine where the probable point or points of damage may occur in a digital design of the appliance prior to manufacturing and may perform a corrective action.

Additional information may be added to the appliance. The additional information may be any information that pertains to the appliance. Examples of such additional information includes a part number identifier, patient name, a patient identifier, a case number, a sequence identifier (e.g., indicating which appliance a particular liner is in a treatment sequence), a date of manufacture, a clinician name, a logo and so forth. For example, after determining there is a probable point of damage in a digital design of an appliance, an indicator may be inserted into the digital design of the appliance. The indicator may represent a recommended place to begin removing the polymeric appliance to prevent the point of damage from manifesting during removal in some embodiments.

In some embodiments, a library of removal methods/patterns may be established and this library may be referenced when simulating the removal of the aligner in the numerical simulation. Different patients or production technicians may tend to remove aligners differently, and there might be a few typical patterns. For example: 1) some patients lift from the lingual side of posteriors first (first left and then right, or vice versa), and then go around the arch from left/right posterior section to the right/left posterior section; 2) similar to #1, but some other patients lift only one side of the posterior and then go around the arch; 3) similar to #1, but some patients lift from the buccal side rather than the lingual side of the posterior; 4) some patients lift from the anterior incisors and pull hard to remove the aligner; 5) some other patients grab both lingual and buccal side of a posterior location and pull out both sides at the same time; 6) some other patients grab a random tooth in the middle. The library can also include a removal guideline provided by the manufacturer of the aligner. Removal approach may also depend on presence or absence of attachments on teeth as some pf the above method may result in more comfortable way of removal. Based on the attachment situation on each tooth, it can be determined how each patient would probably remove an aligner and adapt that removal procedure for that patient in that specific simulation.

After an appliance is formed over a mold for a treatment stage, that appliance is subsequently trimmed along a cutline (also referred to as a trim line) and the appliance may be removed from the mold. The processing logic may determine a cutline for the appliance. The determination of the cutline(s) may be made based on the virtual 3D model of the dental arch at a particular treatment stage, based on a virtual 3D model of the appliance to be formed over the dental arch, or a combination of a virtual 3D model of the dental arch and a virtual 3D model of the appliance. The location and shape of the cutline can be important to the functionality of the appliance (e.g., an ability of the appliance to apply desired forces to a patient's teeth) as well as the fit and comfort of the appliance. For shells such as orthodontic appliances, orthodontic retainers and orthodontic splints, the trimming of the shell may play a role in the efficacy of the shell for its intended purpose (e.g., aligning, retaining or positioning one or more teeth of a patient) as well as the fit of the shell on a patient's dental arch. For example, if too much of the shell is trimmed, then the shell may lose rigidity and an ability of the shell to exert force on a patient's teeth may be compromised. When too much of the shell is trimmed, the shell may become weaker at that location and may be a point of damage when a patient removes the shell from their teeth or when the shell is removed from the mold. In some embodiments, the cut line may be modified in the digital design of the appliance as one of the corrective actions taken when a probable point of damage is determined to exist in the digital design of the appliance.

On the other hand, if too little of the shell is trimmed, then portions of the shell may impinge on a patient's gums and cause discomfort, swelling, and/or other dental issues. Additionally, if too little of the shell is trimmed at a location, then the shell may be too rigid at that location. In some embodiments, the cutline may be a straight line across the appliance at the gingival line, below the gingival line, or above the gingival line. In some embodiments, the cutline may be a gingival cutline that represents an interface between an appliance and a patient's gingiva. In such embodiments, the cutline controls a distance between an edge of the appliance and a gum line or gingival surface of a patient.

In embodiments virtual fillers may be used to reduce a likelihood of the occurrence of probable points of damage. When a probably point of damage is identified, a virtual filler may be added to a region associated with the probable point of damage or an existing virtual filler at that region may be enlarged. For example, virtual fillers in interproximal regions may be added or enlarged.

Each patient has a unique dental arch with unique gingiva. Accordingly, the shape and position of the cutline may be unique and customized for each patient and for each stage of treatment. For instance, the cutline is customized to follow along the gum line (also referred to as the gingival line). In some embodiments, the cutline may be away from the gum line in some regions and on the gum line in other regions. For example, it may be desirable in some instances for the cutline to be away from the gum line (e.g., not touching the gum) where the shell will touch a tooth and on the gum line (e.g., touching the gum) in the interproximal regions between teeth. Accordingly, it is important that the shell be trimmed along a predetermined cutline.

In some embodiments, the orthodontic appliances herein (or portions thereof) can be produced using direct fabrication, such as additive manufacturing techniques (also referred to herein as "3D printing) or subtractive manufacturing techniques (e.g., milling). In some embodiments, direct fabrication involves forming an object (e.g., an orthodontic appliance or a portion thereof) without using a physical template (e.g., mold, mask etc.) to define the object geometry. Additive manufacturing techniques can be categorized as follows: (1) vat photopolymerization (e.g., stereolithography), in which an object is constructed layer by layer from a vat of liquid photopolymer resin; (2) material jetting, in which material is jetted onto a build platform using either a continuous or drop on demand (DOD) approach; (3) binder jetting, in which alternating layers of a build material (e.g., a powder-based material) and a binding material (e.g., a liquid binder) are deposited by a print head; (4) fused deposition modeling (FDM), in which material is drawn though a nozzle, heated, and deposited layer by layer; (5) powder bed fusion, including but not limited to direct metal laser sintering (DMLS), electron beam melting (EBM), selective heat sintering (SHS), selective laser melting (SLM), and selective laser sintering (SLS); (6) sheet lamination, including but not limited to laminated object manufacturing (LOM) and ultrasonic additive manufacturing (UAM); and (7) directed energy deposition, including but not limited to laser engineering net shaping, directed light fabrication, direct metal deposition, and 3D laser cladding. For example, stereolithography can be used to directly fabricate one or more of the appliances 1512, 1514, 1516. In some embodiments, stereolithography involves selective polymerization of a photosensitive resin (e.g., a photopolymer) according to a desired cross-sectional shape using light (e.g., ultraviolet light). The object geometry can be built up in a layer-by-layer fashion by sequentially polymerizing a plurality of object cross-sections. As another example, the appliances 1512, 1514, 1516 can be directly fabricated using selective laser sintering. In some embodiments, selective laser sintering involves using a laser beam to selectively melt and fuse a layer of powdered material according to a desired cross-sectional shape in order to build up the object geometry. As yet another example, the appliances 1512, 1514, 1516 can be directly fabricated by fused deposition modeling. In some embodiments, fused deposition modeling involves melting and selectively depositing a thin filament of thermoplastic polymer in a layer-by-layer manner in order to form an object. In yet another example, material jetting can be used to directly fabricate the appliances 1512, 1514, 1516. In some embodiments, material jetting involves jetting or extruding one or more materials onto a build surface in order to form successive layers of the object geometry.

In some embodiments, the direct fabrication methods provided herein build up the object geometry in a layer-by-layer fashion, with successive layers being formed in discrete build steps. Alternatively or in combination, direct fabrication methods that allow for continuous build-up of an object geometry can be used, referred to herein as "continuous direct fabrication." Various types of continuous direct fabrication methods can be used. As an example, in some embodiments, the appliances 1512, 1514, 1516 are fabricated using "continuous liquid interphase printing," in which an object is continuously built up from a reservoir of photopolymerizable resin by forming a gradient of partially cured resin between the building surface of the object and a polymerization-inhibited "dead zone." In some embodiments, a semi-permeable membrane is used to control transport of a photopolymerization inhibitor (e.g., oxygen) into the dead zone in order to form the polymerization gradient. Continuous liquid interphase printing can achieve fabrication speeds about 25 times to about 100 times faster than other direct fabrication methods, and speeds about 1000 times faster can be achieved with the incorporation of cooling systems. Continuous liquid interphase printing is described in U.S. Patent Publication Nos. 2015/0097315, 2015/0097316, and 2015/0102532, the disclosures of each of which are incorporated herein by reference in their entirety.

As another example, a continuous direct fabrication method can achieve continuous build-up of an object geometry by continuous movement of the build platform (e.g., along the vertical or Z-direction) during the irradiation phase, such that the hardening depth of the irradiated photopolymer is controlled by the movement speed. Accordingly, continuous polymerization of material on the build surface can be achieved. Such methods are described in U.S. Pat. No. 7,892,474, the disclosure of which is incorporated herein by reference in its entirety.

In another example, a continuous direct fabrication method can involve extruding a composite material composed of a curable liquid material surrounding a solid strand.

The composite material can be extruded along a continuous three-dimensional path in order to form the object. Such methods are described in U.S. Patent Publication No. 2014/0061974, the disclosure of which is incorporated herein by reference in its entirety.

In yet another example, a continuous direct fabrication method utilizes a "heliolithography" approach in which the liquid photopolymer is cured with focused radiation while the build platform is continuously rotated and raised. Accordingly, the object geometry can be continuously built up along a spiral build path. Such methods are described in U.S. Patent Publication No. 2014/0265034, the disclosure of which is incorporated herein by reference in its entirety.

The direct fabrication approaches provided herein are compatible with a wide variety of materials, including but not limited to one or more of the following: a polyester, a co-polyester, a polycarbonate, a thermoplastic polyurethane, a polypropylene, a polyethylene, a polypropylene and polyethylene copolymer, an acrylic, a cyclic block copolymer, a polyetheretherketone, a polyamide, a polyethylene terephthalate, a polybutylene terephthalate, a polyetherimide, a polyethersulfone, a polytrimethylene terephthalate, a styrenic block copolymer (SBC), a silicone rubber, an elastomeric alloy, a thermoplastic elastomer (TPE), a thermoplastic vulcanizate (TPV) elastomer, a polyurethane elastomer, a block copolymer elastomer, a polyolefin blend elastomer, a thermoplastic co-polyester elastomer, a thermoplastic polyamide elastomer, a thermoset material, or combinations thereof. The materials used for direct fabrication can be provided in an uncured form (e.g., as a liquid, resin, powder, etc.) and can be cured (e.g., by photopolymerization, light curing, gas curing, laser curing, crosslinking, etc.) in order to form an orthodontic appliance or a portion thereof. The properties of the material before curing may differ from the properties of the material after curing. Once cured, the materials herein can exhibit sufficient strength, stiffness, durability, biocompatibility, etc. for use in an orthodontic appliance. The post-curing properties of the materials used can be selected according to the desired properties for the corresponding portions of the appliance.

In some embodiments, relatively rigid portions of the orthodontic appliance can be formed via direct fabrication using one or more of the following materials: a polyester, a co-polyester, a polycarbonate, a thermoplastic polyurethane, a polypropylene, a polyethylene, a polypropylene and polyethylene copolymer, an acrylic, a cyclic block copolymer, a polyetheretherketone, a polyamide, a polyethylene terephthalate, a polybutylene terephthalate, a polyetherimide, a polyethersulfone, and/or a polytrimethylene terephthalate.

In some embodiments, relatively elastic portions of the orthodontic appliance can be formed via direct fabrication using one or more of the following materials: a styrenic block copolymer (SBC), a silicone rubber, an elastomeric alloy, a thermoplastic elastomer (TPE), a thermoplastic vulcanizate (TPV) elastomer, a polyurethane elastomer, a block copolymer elastomer, a polyolefin blend elastomer, a thermoplastic co-polyester elastomer, and/or a thermoplastic polyamide elastomer.

Machine parameters can include curing parameters. For digital light processing (DLP)-based curing systems, curing parameters can include power, curing time, and/or grayscale of the full image. For laser-based curing systems, curing parameters can include power, speed, beam size, beam shape and/or power distribution of the beam. For printing systems, curing parameters can include material drop size, viscosity, and/or curing power. These machine parameters can be monitored and adjusted on a regular basis (e.g., some parameters at every 1-x layers and some parameters after each build) as part of the process control on the fabrication machine. Process control can be achieved by including a sensor on the machine that measures power and other beam parameters every layer or every few seconds and automatically adjusts them with a feedback loop. For DLP machines, gray scale can be measured and calibrated before, during, and/or at the end of each build, and/or at predetermined time intervals (e.g., every $n^{th}$ build, once per hour, once per day, once per week, etc.), depending on the stability of the system. In addition, material properties and/or photo-characteristics can be provided to the fabrication machine, and a machine process control module can use these parameters to adjust machine parameters (e.g., power, time, gray scale, etc.) to compensate for variability in material properties. By implementing process controls for the fabrication machine, reduced variability in appliance accuracy and residual stress can be achieved.

Optionally, the direct fabrication methods described herein allow for fabrication of an appliance including multiple materials, referred to herein as "multi-material direct fabrication." In some embodiments, a multi-material direct fabrication method involves concurrently forming an object from multiple materials in a single manufacturing step. For instance, a multi-tip extrusion apparatus can be used to selectively dispense multiple types of materials from distinct material supply sources in order to fabricate an object from a plurality of different materials. Such methods are described in U.S. Pat. No. 6,749,414, the disclosure of which is incorporated herein by reference in its entirety. Alternatively or in combination, a multi-material direct fabrication method can involve forming an object from multiple materials in a plurality of sequential manufacturing steps. For instance, a first portion of the object can be formed from a first material in accordance with any of the direct fabrication methods herein, then a second portion of the object can be formed from a second material in accordance with methods herein, and so on, until the entirety of the object has been formed.

Direct fabrication can provide various advantages compared to other manufacturing approaches. For instance, in contrast to indirect fabrication, direct fabrication permits production of an orthodontic appliance without utilizing any molds or templates for shaping the appliance, thus reducing the number of manufacturing steps involved and improving the resolution and accuracy of the final appliance geometry. Additionally, direct fabrication permits precise control over the three-dimensional geometry of the appliance, such as the appliance thickness. Complex structures and/or auxiliary components can be formed integrally as a single piece with the appliance shell in a single manufacturing step, rather than being added to the shell in a separate manufacturing step. In some embodiments, direct fabrication is used to produce appliance geometries that would be difficult to create using alternative manufacturing techniques, such as appliances with very small or fine features, complex geometric shapes, undercuts, interproximal structures, shells with variable thicknesses, and/or internal structures (e.g., for improving strength with reduced weight and material usage). For example, in some embodiments, the direct fabrication approaches herein permit fabrication of an orthodontic appliance with feature sizes of less than or equal to about 5 µm, or within a range from about 5 µm to about 50 µm, or within a range from about 20 µm to about 50 µm.

The direct fabrication techniques described herein can be used to produce appliances with substantially isotropic material properties, e.g., substantially the same or similar strengths along all directions. In some embodiments, the direct fabrication approaches herein permit production of an orthodontic appliance with a strength that varies by no more than about 25%, about 20%, about 15%, about 10%, about 5%, about 1%, or about 0.5% along all directions. Additionally, the direct fabrication approaches herein can be used to produce orthodontic appliances at a faster speed compared to other manufacturing techniques. In some embodiments, the direct fabrication approaches herein allow for production of an orthodontic appliance in a time interval less than or equal to about 1 hour, about 30 minutes, about 25 minutes, about 20 minutes, about 15 minutes, about 10 minutes, about 5 minutes, about 4 minutes, about 3 minutes, about 2 minutes, about 1 minutes, or about 30 seconds. Such manufacturing speeds allow for rapid "chair-side" production of customized appliances, e.g., during a routine appointment or checkup.

In some embodiments, the direct fabrication methods described herein implement process controls for various machine parameters of a direct fabrication system or device in order to ensure that the resultant appliances are fabricated with a high degree of precision. Such precision can be beneficial for ensuring accurate delivery of a desired force system to the teeth in order to effectively elicit tooth movements. Process controls can be implemented to account for process variability arising from multiple sources, such as the material properties, machine parameters, environmental variables, and/or post-processing parameters.

Material properties may vary depending on the properties of raw materials, purity of raw materials, and/or process variables during mixing of the raw materials. In many embodiments, resins or other materials for direct fabrication should be manufactured with tight process control to ensure little variability in photo-characteristics, material properties (e.g., viscosity, surface tension), physical properties (e.g., modulus, strength, elongation) and/or thermal properties (e.g., glass transition temperature, heat deflection temperature). Process control for a material manufacturing process can be achieved with screening of raw materials for physical properties and/or control of temperature, humidity, and/or other process parameters during the mixing process. By implementing process controls for the material manufacturing procedure, reduced variability of process parameters and more uniform material properties for each batch of material can be achieved. Residual variability in material properties can be compensated with process control on the machine, as discussed further herein.

Machine parameters can include curing parameters. For digital light processing (DLP)-based curing systems, curing parameters can include power, curing time, and/or grayscale of the full image. For laser-based curing systems, curing parameters can include power, speed, beam size, beam shape and/or power distribution of the beam. For printing systems, curing parameters can include material drop size, viscosity, and/or curing power. These machine parameters can be monitored and adjusted on a regular basis (e.g., some parameters at every 1-x layers and some parameters after each build) as part of the process control on the fabrication machine. Process control can be achieved by including a sensor on the machine that measures power and other beam parameters every layer or every few seconds and automatically adjusts them with a feedback loop. For DLP machines, gray scale can be measured and calibrated at the end of each build. In addition, material properties and/or photo-characteristics can be provided to the fabrication machine, and a machine process control module can use these parameters to adjust machine parameters (e.g., power, time, gray scale, etc.) to compensate for variability in material properties. By implementing process controls for the fabrication machine, reduced variability in appliance accuracy and residual stress can be achieved.

In many embodiments, environmental variables (e.g., temperature, humidity, Sunlight or exposure to other energy/curing source) are maintained in a tight range to reduce variable in appliance thickness and/or other properties. Optionally, machine parameters can be adjusted to compensate for environmental variables.

In many embodiments, post-processing of appliances includes cleaning, post-curing, and/or support removal processes. Relevant post-processing parameters can include purity of cleaning agent, cleaning pressure and/or temperature, cleaning time, post-curing energy and/or time, and/or consistency of support removal process. These parameters can be measured and adjusted as part of a process control scheme. In addition, appliance physical properties can be varied by modifying the post-processing parameters. Adjusting post-processing machine parameters can provide another way to compensate for variability in material properties and/or machine properties.

The configuration of the orthodontic appliances herein can be determined according to a treatment plan for a patient, e.g., a treatment plan involving successive administration of a plurality of appliances for incrementally repositioning teeth. Computer-based treatment planning and/or appliance manufacturing methods can be used in order to facilitate the design and fabrication of appliances. For instance, one or more of the appliance components described herein can be digitally designed and fabricated with the aid of computer-controlled manufacturing devices (e.g., computer numerical control (CNC) milling, computer-controlled rapid prototyping such as 3D printing, etc.). The computer-based methods presented herein can improve the accuracy, flexibility, and convenience of appliance fabrication.

FIG. 15C illustrates a method 1550 of orthodontic treatment using a plurality of appliances (e.g., a plurality of aligners), in accordance with embodiments. The method 1550 can be practiced using any of the appliances or appliance sets described herein. In block 1560, a first orthodontic appliance is applied to a patient's teeth in order to reposition the teeth from a first tooth arrangement to a second tooth arrangement. In block 1570, a second orthodontic appliance is applied to the patient's teeth in order to reposition the teeth from the second tooth arrangement to a third tooth arrangement. The method 1550 can be repeated as necessary using any suitable number and combination of sequential appliances in order to incrementally reposition the patient's teeth from an initial arrangement to a target arrangement. The appliances can be generated all at the same stage or in sets or batches (e.g., at the beginning of a stage of the treatment), or the appliances can be fabricated one at a time, and the patient can wear each appliance until the pressure of each appliance on the teeth can no longer be felt or until the maximum amount of expressed tooth movement for that given stage has been achieved. A plurality of different appliances (e.g., a set) can be designed and even fabricated prior to the patient wearing any appliance of the plurality. After wearing an appliance for an appropriate period of time, the patient can replace the current appliance with the next appliance in the series until no more appliances remain. The appliances are generally not affixed to the teeth and the patient may place and replace the appliances at any time during the procedure (e.g., patient-removable appliances). The final appliance or several appliances in the series may have a geometry or geometries selected to overcorrect the tooth arrangement. For instance, one or more appliances may have a geometry that would (if fully achieved) move individual teeth beyond the tooth arrangement that has been selected as the "final." Such over-correction may be desirable in order to offset potential relapse after the repositioning method has been terminated (e.g., permit movement of individual teeth back toward their pre-corrected positions). Over-correction may also be beneficial to speed the rate of correction (e.g., an appliance with a geometry that is positioned beyond a desired intermediate or final position may shift the individual teeth toward the position at a greater rate). In such cases, the use of an appliance can be terminated before the teeth reach the positions defined by the appliance. Furthermore, over-correction may be deliberately applied in order to compensate for any inaccuracies or limitations of the appliance.

FIG. 16 illustrates a method 1600 for designing an orthodontic appliance to be produced by direct fabrication, in accordance with embodiments. The method 1600 can be applied to any embodiment of the orthodontic appliances described herein. Some or all of the blocks of the method 1600 can be performed by any suitable data processing system or device, e.g., one or more processors configured with suitable instructions.

In block 1610, a movement path to move one or more teeth from an initial arrangement to a target arrangement is determined. The initial arrangement can be determined from a mold or a scan of the patient's teeth or mouth tissue, e.g., using wax bites, direct contact scanning, x-ray imaging, tomographic imaging, sonographic imaging, and other techniques for obtaining information about the position and structure of the teeth, jaws, gums and other orthodontically relevant tissue. From the obtained data, a digital data set can be derived that represents the initial (e.g., pretreatment) arrangement of the patient's teeth and other tissues. Optionally, the initial digital data set is processed to segment the tissue constituents from each other. For example, data structures that digitally represent individual tooth crowns can be produced. Advantageously, digital models of entire teeth can be produced, including measured or extrapolated hidden surfaces and root structures, as well as surrounding bone and soft tissue.

The target arrangement of the teeth (e.g., a desired and intended end result of orthodontic treatment) can be received from a clinician in the form of a prescription, can be calculated from basic orthodontic principles, and/or can be extrapolated computationally from a clinical prescription. With a specification of the desired final positions of the teeth and a digital representation of the teeth themselves, the final position and surface geometry of each tooth can be specified to form a complete model of the tooth arrangement at the desired end of treatment.

Having both an initial position and a target position for each tooth, a movement path can be defined for the motion of each tooth. In some embodiments, the movement paths are configured to move the teeth in the quickest fashion with the least amount of round-tripping to bring the teeth from their initial positions to their desired target positions. The tooth paths can optionally be segmented, and the segments can be calculated so that each tooth's motion within a segment stays within threshold limits of linear and rotational translation. In this way, the end points of each path segment can constitute a clinically viable repositioning, and the aggregate of segment end points can constitute a clinically viable sequence of tooth positions, so that moving from one point to the next in the sequence does not result in a collision of teeth.

In block 1620, a force system to produce movement of the one or more teeth along the movement path is determined. A force system can include one or more forces and/or one or more torques. Different force systems can result in different types of tooth movement, such as tipping, translation, rotation, extrusion, intrusion, root movement, etc. Biomechanical principles, modeling techniques, force calculation/measurement techniques, and the like, including knowledge and approaches commonly used in orthodontia, may be used to determine the appropriate force system to be applied to the tooth to accomplish the tooth movement. In determining the force system to be applied, sources may be considered including literature, force systems determined by experimentation or virtual modeling, computer-based modeling, clinical experience, minimization of unwanted forces, etc.

The determination of the force system can include constraints on the allowable forces, such as allowable directions and magnitudes, as well as desired motions to be brought about by the applied forces. For example, in fabricating palatal expanders, different movement strategies may be desired for different patients. For example, the amount of force needed to separate the palate can depend on the age of the patient, as very young patients may not have a fully-formed suture. Thus, in juvenile patients and others without fully-closed palatal sutures, palatal expansion can be accomplished with lower force magnitudes. Slower palatal movement can also aid in growing bone to fill the expanding suture. For other patients, a more rapid expansion may be desired, which can be achieved by applying larger forces. These requirements can be incorporated as needed to choose the structure and materials of appliances; for example, by choosing palatal expanders capable of applying large forces for rupturing the palatal suture and/or causing rapid expansion of the palate. Subsequent appliance stages can be designed to apply different amounts of force, such as first applying a large force to break the suture, and then applying smaller forces to keep the suture separated or gradually expand the palate and/or arch.

The determination of the force system can also include modeling of the facial structure of the patient, such as the skeletal structure of the jaw and palate. Scan data of the palate and arch, such as Xray data or 3D optical scanning data, for example, can be used to determine parameters of the skeletal and muscular system of the patient's mouth, so as to determine forces sufficient to provide a desired expansion of the palate and/or arch. In some embodiments, the thickness and/or density of the mid-palatal suture may be measured, or input by a treating professional. In other embodiments, the treating professional can select an appropriate treatment based on physiological characteristics of the patient. For example, the properties of the palate may also be estimated based on factors such as the patient's age—for example, young juvenile patients will typically require lower forces to expand the suture than older patients, as the suture has not yet fully formed.

In block 1630, an orthodontic appliance configured to produce the force system is determined. Determination of the orthodontic appliance, appliance geometry, material composition, and/or properties can be performed using a treatment or force application simulation environment. A simulation environment can include, e.g., computer modeling systems, biomechanical systems or apparatus, and the like. Optionally, digital models of the appliance and/or teeth can be produced, such as finite element models. The finite element models can be created using computer program application software available from a variety of vendors. For creating solid geometry models, computer aided engineering (CAE) or computer aided design (CAD) programs can be used, such as the AutoCAD® software products available from Autodesk, Inc., of San Rafael, Calif. For creating finite element models and analyzing them, program products from a number of vendors can be used, including finite element analysis packages from ANSYS, Inc., of Canonsburg, Pa., and SIMULIA(Abaqus) software products from Dassault Systèmes of Waltham, Mass.

Optionally, one or more orthodontic appliances can be selected for testing or force modeling. As noted above, a desired tooth movement, as well as a force system required or desired for eliciting the desired tooth movement, can be identified. Using the simulation environment, a candidate orthodontic appliance can be analyzed or modeled for determination of an actual force system resulting from use of the candidate appliance. One or more modifications can optionally be made to a candidate appliance, and force modeling can be further analyzed as described, e.g., in order to iteratively determine an appliance design that produces the desired force system.

In block 1640, instructions for fabrication of the orthodontic appliance incorporating the orthodontic appliance are generated. The instructions can be configured to control a fabrication system or device in order to produce the orthodontic appliance with the specified orthodontic appliance. In some embodiments, the instructions are configured for manufacturing the orthodontic appliance using direct fabrication (e.g., stereolithography, selective laser sintering, fused deposition modeling, 3D printing, continuous direct fabrication, multi-material direct fabrication, etc.), in accordance with the various methods presented herein. In alternative embodiments, the instructions can be configured for indirect fabrication of the appliance, e.g., by thermoforming.

Method 1600 may comprise additional blocks: 1) The upper arch and palate of the patient is scanned intraorally to generate three dimensional data of the palate and upper arch; 2) The three dimensional shape profile of the appliance is determined to provide a gap and teeth engagement structures as described herein.

Although the above blocks show a method 1600 of designing an orthodontic appliance in accordance with some embodiments, a person of ordinary skill in the art will recognize some variations based on the teaching described herein. Some of the blocks may comprise sub-blocks. Some of the blocks may be repeated as often as desired. One or more blocks of the method 1600 may be performed with any suitable fabrication system or device, such as the embodiments described herein. Some of the blocks may be optional, and the order of the blocks can be varied as desired.

Figure 17:
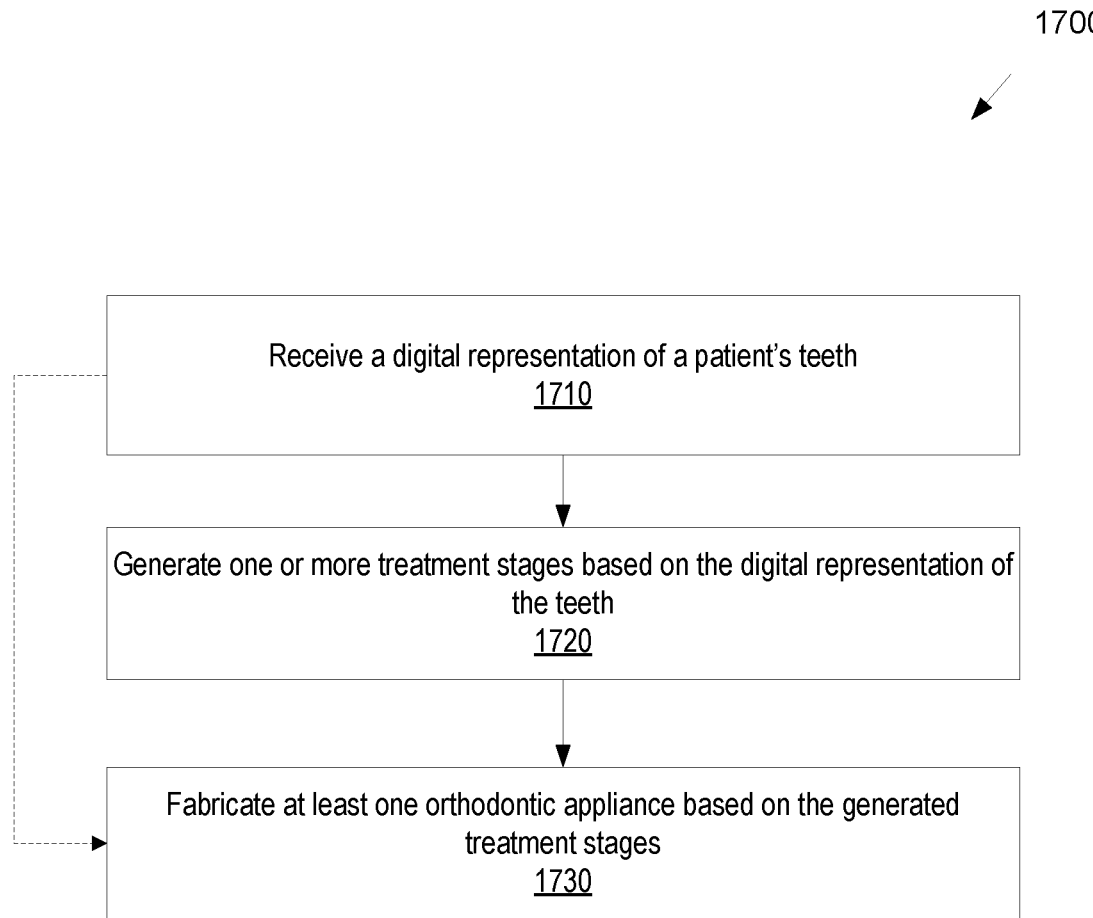
FIG. 17 illustrates a method for digitally planning an orthodontic treatment, in accordance with embodiments.

FIG. 17 illustrates a method 1700 for digitally planning an orthodontic treatment and/or design or fabrication of an appliance, in accordance with embodiments. The method 1700 can be applied to any of the treatment procedures described herein and can be performed by any suitable data processing system.

In block 1710, a digital representation of a patient's dental arch is received. The digital representation can include surface topography data for the patient's intraoral cavity (including teeth, gingival tissues, etc.). The surface topography data can be generated by directly scanning the intraoral cavity, a physical model (positive or negative) of the intraoral cavity, or an impression of the intraoral cavity, using a suitable scanning device (e.g., a handheld scanner, desktop scanner, etc.).

In block 1720, one or more treatment stages are generated based on the digital representation of the dental arch. The treatment stages can be incremental repositioning stages of an orthodontic treatment procedure designed to move one or more of the patient's teeth from an initial tooth arrangement to a target arrangement. For example, the treatment stages can be generated by determining the initial tooth arrangement indicated by the digital representation, determining a target tooth arrangement, and determining movement paths of one or more teeth in the initial arrangement necessary to achieve the target tooth arrangement. The movement path can be optimized based on minimizing the total distance moved, preventing collisions between teeth, avoiding tooth movements that are more difficult to achieve, or any other suitable criteria.

In block 1730, at least one orthodontic appliance (e.g., at least one aligner) is fabricated based on the generated treatment stages. For example, a set of appliances can be fabricated, each shaped according a tooth arrangement specified by one of the treatment stages, such that the appliances can be sequentially worn by the patient to incrementally reposition the teeth from the initial arrangement to the target arrangement. The appliance set may include one or more of the orthodontic appliances described herein. The fabrication of the appliance may involve creating a digital model of the appliance to be used as input to a computer-controlled fabrication system. The appliance can be formed using direct fabrication methods, indirect fabrication methods, or combinations thereof, as desired.

In some instances, staging of various arrangements or treatment stages may not be necessary for design and/or fabrication of an appliance. As illustrated by the dashed line in FIG. 17, design and/or fabrication of an orthodontic appliance, and perhaps a particular orthodontic treatment, may include use of a representation of the patient's teeth (e.g., receive a digital representation of the patient's teeth at block 1710), followed by design and/or fabrication of an orthodontic appliance based on a representation of the patient's teeth in the arrangement represented by the received representation.

FIG. 18 illustrates a method 1800 for implementing one or more corrective actions to a polymeric aligner based on a simulated removal of the polymeric aligner from a dental arch. The method 1800 can be applied to any of the procedures described herein and can be performed by any suitable data processing system, including the system of FIG. 14.

At block 1802, a first digital model representing a dental arch-like structure of a patient may be gathered. The dental arch-like structure may include one or more teeth-like structures of a patient that interface with a polymeric aligner. A "dental arch-like structure," as used herein, may include a structure that has structures that correspond to a dentition of a patient. In some implementations, a dental arch-like structure comprises a physical mold used to form polymeric aligners. A dental arch-like structure may include regions for attachments, bubbles, and/or other structures adhered (e.g., bonded) to teeth and/or tooth-like structures; and/or pressure areas, power ridges and/or other structures subtracted/taken away from teeth and/or teeth-like structures. A dental arch-like structure may, in various implementations, comprise the actual dentition of the patient. A dental arch-like structure may be identified using physical impressions, scans, and/or techniques used to form a physical mold to indirectly fabricate polymeric aligners. As a result, in some implementations, the first digital model represents a physical mold (prophetic, actual, etc.) that is used as the basis of indirectly fabricating an aligner. The first digital model may include a 3D representation of a physical mold and/or may correspond to a file (e.g., an STL file) used to fabricate (e.g., 3D print) a physical mold of the aligner. The first digital model may specify one or more material properties of a physical mold, such as one or more surface properties of the materials of a physical mold that would cause friction against an aligner coupled to that physical mold. In various implementations, the first model of the dental arch-like structure may comprise may specify one or more physical properties, such as biomechanical resistance, friction, other surface properties etc. associated with a patient's dentition and/or the patient's wearing of a polymeric aligner on his or her dental arch.

At block 1804, a second digital model representing the polymeric aligner to be supported by the dental arch-like structure may be gathered. The second digital model may include a 3D representation of the polymeric aligner and/or may include data related to force(s), torque(s), and/or other orthodontic repositioning elements to be implemented on the dental arch. In some implementations, the polymeric aligner may include one or more tooth-receiving cavities configured to apply the repositioning forces to the one or more teeth-like structures of the dental arch-like structure. The second digital model may specify at least some physical properties of the polymeric aligner at one or more regions of the polymeric aligner. As noted herein, the physical properties may correspond to material properties of the polymeric aligner, such as acceptable material strains at various areas. The second digital model may specify, for various regions, whether the polymeric aligner is likely to suffer physical damage (e.g., to deform, warp, fail, and/or break). In some implementations, the second digital model may break the aligner down into finite elements and may associate the physical properties with those finite elements. As noted herein, one or more of the finite elements may be characterized by a particular material property that is associated with a particular material strain.

At block 1806, an interaction of the polymeric aligner to the dental arch-like structure is simulated using the first digital model and the second digital model. An example of such an interaction is a coupling, but it is noted the polymeric aligner and the dental arch-like structure may physically interact with one another without being coupled to one another. One or more spatial points of the first digital model may be aligned with corresponding spatial points of the second digital model to simulate placing the polymeric aligner to the dental arch-like structure. In some implementations, a virtual spring force may be used to model interactions between the cavities of the polymeric aligner and corresponding teeth-like structures in the dental arch-like structure. In various implementations, the interaction may be modeled by alignment of finite elements of the second digital model against corresponding spatial elements of the first digital model.

At block 1808, removal of the polymeric aligner from the dental arch-like structure may be simulated using the first digital model and the second digital model. In some implementations, an interaction between the physical properties of the aligner and the second physical properties of a physical mold may be simulated. As an example, an interaction between material properties of the aligner and material properties of a physical mold at various regions in space may be simulated. In various implementations, an interaction between physical properties of the aligner and physical properties associated with wearing the aligner on the dental arch by a patient (e.g., properties associated with biomechanical forces exerted by teeth and/or properties associated with an intraoral environment) may be simulated. Additionally, simulating removal of the polymeric aligner from the dental arch-like structure may comprise simulating a spring removal force between cavities of the polymeric aligner and corresponding teeth-like structures. Spring removal forces, as noted herein, may correspond to the force sufficient to exceed a virtual spring force (e.g., a modeled force against the polymeric aligner by a mold or dental arch). Simulating the removal of the polymeric aligner from the dental arch-like structure may comprise simulating a sequential removal of the polymeric aligner from a first posterior tooth-like structure of the dental arch-like structure to a second opposing posterior tooth-like structure of the dental arch-like structure. It is noted simulating the removal of the polymeric aligner from the dental arch-like structure may comprise: simulating removal from anterior tooth-like structures followed by posterior tooth-like structures, simulating removal from attachment-like structures on the dental arch-like structure followed by other structures, etc.

At block 1810, a likeliness of one or more physical strains at the one or more regions will satisfy one or more strain/stress or deformation energy-based damage criteria may be determined based on an interaction of the dental arch-like structure and the first one or more physical properties, where the interaction is due to the simulated removal. "Strain/stress or deformation energy-based damage criteria," as used herein, may include a set of criteria for determining whether strains/stresses to a region of a structure will meet, exceed, etc. a specified threshold. Strain/stress or deformation energy-based criteria may include numerical scores (e.g., Boolean and/or decimal values) or may be implemented using various techniques. One or more values representing the interaction between the physical properties of the aligner and the physical properties of the or dental arch-like structure may be determined. These values may represent likeliness of physical strains (structural strains, material strains, etc.) on various regions of the aligner due to removal. As noted herein, each region (e.g., each finite element) may have values associated with it. Block 1810 may involve reducing a thickness of the polymeric aligner represented in the second digital model until the first one or more physical properties of the polymeric aligner at one or more regions of the polymeric aligner meet, exceed, etc. strain/stress or deformation energy-based damage criteria for the one or more regions.

At block 1812, the second digital model is analyzed for one or more likely points of structural damage based on the likeliness of the one or more physical strains at the one or more regions. In some implementations, values for the physical strains at various regions are compared to various thresholds (e.g., strain thresholds) for those regions. Regions having values below/meeting/exceeding those thresholds may be identified.

At block 1814, in response to analyzing the second digital model for the one or more likely points of structural damage, it may be determined whether to implement one or more corrective actions for the polymeric aligner. In some implementations, the one or more corrective actions comprise modifying an aligner geometry of the polymeric aligner to accommodate the one or more likely points of structural damage. As various examples, the one or more corrective actions may guide placement of cut lines, bite ramps, power ridges, attachments, etc. at locations other than those locations specified in the second digital model. The corrective actions may guide modification of aligner thickness or density for various regions of the aligner. The corrective actions may include, e.g., instructions to modify fabrication of the aligner as noted herein and/or instructions to modify a treatment plan, as noted further herein.

At block 1816, a third digital model representing the polymeric aligner may be generated. The third digital model may be based on the second digital model and the one or more corrective actions for the polymeric aligner. The third digital model may represent a modified aligner with, e.g., a modified aligner geometry (modified cut lines, bite ramps, power ridges, attachments, aligner thickness for various regions, etc.). The modified aligner may be used as the basis of a modified fabrication process and/or a modified treatment plan.

In some implementations, fabrication instructions to fabricate a modified polymeric aligner based on the third digital model may be provided. In some implementations, the fabrication instructions may include: mold formation instructions to form a physical aligner mold for the polymeric aligner using the third digital model; and/or thermoforming instructions to thermoform the polymeric aligner from a sheet of polymeric material placed over the physical aligner mold. As noted herein, the third digital model may include one or more structural features at points relative to corresponding points of the second digital model, the one or more structural features being configured to accommodate the one or more corrective actions. In various implementations, the fabrication instructions comprise direct fabrication instructions to directly fabricate the polymeric aligner using the third digital model. As noted herein, the third digital model may include one or more areas of modified thickness relative to corresponding areas of the second digital model, the one or more areas of modified thickness being configured to accommodate the one or more corrective actions It is to be understood that the above description is intended to be illustrative, and not restrictive. Many other embodiments will be apparent upon reading and understanding the above description. Although embodiments of the present disclosure have been described with reference to specific example embodiments, it will be recognized that the disclosure is not limited to the embodiments described, but can be practiced with modification and alteration within the spirit and scope of the appended claims. Accordingly, the specification and drawings are to be regarded in an illustrative sense rather than a restrictive sense. The scope of the disclosure should, therefore, be determined with reference to the appended claims, along with the full scope of equivalents to which such claims are entitled.

What is claimed is:

1. A method comprising:
gathering a virtual three-dimensional (3D) model representing an aligner for a dental arch of a patient, wherein the aligner comprises a plurality of tooth-receiving cavities and a plurality of interproximal regions, wherein each tooth-receiving cavity of the plurality of tooth-receiving cavities is separated from an adjacent tooth-receiving cavity of the plurality of tooth-receiving cavities by an interproximal region of the plurality of interproximal regions;
receiving material property information for a material to be used to manufacture the aligner;
analyzing, by a processing device, one or more of the plurality of interproximal regions of the virtual 3D model of the aligner using the virtual 3D model and the material property information, wherein analyzing an interproximal region of the virtual 3D model of the aligner comprises:
simulating application of a load to the virtual 3D model of the aligner at a region other than the interproximal region in a direction away from the dental arch of the patient or a mold, wherein the load is associated with removal of the aligner from at least one of the dental arch of the patient or the mold;
determining, based on the material property information and the load, at least one of an estimated stress, an estimated strain or an estimated strain energy density at the interproximal region of the virtual 3D model of the aligner that results from application of the load to the virtual 3D model of the aligner during the removal of the aligner from at least one of the dental arch of the patient or the mold;
evaluating an estimated strength of the aligner at the interproximal region of the virtual 3D model of the aligner based at least in part on at least one of the estimated stress, the estimated strain, the estimated strain energy density, or a derived value derived from at least one of the estimated stress, the estimated strain or the estimated strain energy density, determined for the interproximal region of the virtual 3D model of the aligner; and
predicting whether an interproximal region of the aligner corresponding to the interproximal region of the virtual 3D model of the aligner will become damaged based at least in part on the estimated strength of the aligner at the interproximal region of the virtual 3D model of the aligner; and
showing one or more interproximal regions of the aligner that are predicted to become damaged on the virtual 3D model of the aligner.

2. The method of claim 1, wherein analyzing the interproximal region further comprises:
determining whether at least one of the estimated stress, the estimated strain, the estimated strain energy density, or the derived value at the interproximal region exceeds a threshold; and
responsive to determining that at least one of the estimated stress, the estimated strain, the estimated strain energy density, or the derived value exceeds the threshold for the interproximal region, determining that the interproximal region is a probable point of damage for the aligner.

3. The method of claim 2, further comprising:
responsive to determining that the aligner comprises the probable point of damage, selecting for the aligner a manufacturing flow for aligners comprising one or more probable points of damage.

4. The method of claim 2, further comprising:
responsive to determining that the aligner comprises the probable point of damage, implementing one or more corrective actions for the aligner.

5. The method of claim 4, wherein implementing the one or more corrective actions comprises modifying the virtual 3D model of the aligner to generate a modified virtual 3D model of the aligner.

6. The method of claim 5, wherein the virtual 3D model of the aligner was generated based on a virtual 3D model of a dental arch, and wherein modifying the virtual 3D model of the aligner comprises one or more of:
modifying a cutline radius of the virtual 3D model of the aligner;
modifying a thickness of a portion of the virtual 3D model of the aligner;
modifying a geometry of the virtual 3D model of the aligner;

inserting an indicator in the virtual 3D model of the aligner, wherein the indicator represents a recommended place to begin removing the aligner from the mold;

generating a first modified virtual 3D model of the dental arch by modifying one or more attachments on one or more teeth in the virtual 3D model of the dental arch, and generating the modified virtual 3D model of the aligner based on the first modified virtual 3D model of the dental arch; or generating a second modified virtual 3D model of the dental arch by adding or modifying a virtual filler at a location on the virtual 3D model of the dental arch that is associated with the interproximal region, and generating the modified virtual 3D model of the aligner based on the second modified virtual 3D model of the dental arch.

7. The method of claim 1, further comprising performing the following for an additional interproximal region of the virtual 3D model of the aligner:

determining, based on the material property information and the load or a second load, at least one of the estimated stress, the estimated strain, the estimated strain energy density, or the derived value at the additional interproximal region that results from application of the load or the second load;

evaluating an estimated strength of the aligner at the additional interproximal region based at least in part on at least one of the estimated stress, the estimated strain, the estimated strain energy density, or the derived value determined for the additional interproximal region; and determining a probability of the additional interproximal region being damaged based on the estimated strength of the aligner at the additional interproximal region.

8. The method of claim 1, wherein analyzing the interproximal region of the virtual 3D model of the aligner further comprises:

simulating application of a second load; and determining, based on the material property information and the second load, at least one of a second estimated stress, a second estimated strain, a second estimated strain energy density or a second derived value derived from at least one of the second estimated stress, the second estimated strain, or the second estimated strain energy density, at the interproximal region that results from application of the second load;

wherein the estimated strength of the aligner at the interproximal region is based on at least one of the estimated stress and the second estimated stress, the estimated strain and the second estimated strain, or the estimated strain energy density and the second estimated strain energy density, or the derived value and the second derived value determined for the interproximal region.

9. The method of claim 1, wherein the load comprises at least one of a lifting force, a bending force, a twisting force, a shear force, a tension force, or a compression force.

10. The method of claim 1, wherein simulating application of the load comprises:

applying boundary conditions to one or more first locations on a first side of the interproximal region to fix the one or more first locations in place; and applying the load to one or more second locations on a second side of the interproximal region.

11. The method of claim 10, wherein the one or more first locations comprise a first tooth-receiving cavity on the first side of the interproximal region, and wherein the one or more second locations comprise a second tooth-receiving cavity on the second side of the interproximal region.

12. The method of claim 11, wherein the first tooth-receiving cavity is adjacent to the interproximal region, and wherein the second tooth-receiving cavity is a most terminal tooth-receiving cavity on the second side of the interproximal region.

13. The method of claim 11, further comprising:

determining a number of attachments associated with at least one of the first tooth-receiving cavity or a third tooth-receiving cavity that is on the first side of the interproximal region; and determining a magnitude of the load based at least in part on the number of attachments.

14. The method of claim 1, wherein the load comprises a displacement that at least one of lifts, bends, twists, pulls or compresses the virtual 3D model of the aligner.

15. The method of claim 1, further comprising:

receiving at least one of clinical information or treatment-related information associated with the aligner, wherein the clinical information comprises at least one of tooth crowding information, tooth undercut information or tooth geometry information, and wherein the treatment-related information comprises at least one of numbers of attachments associated with one or more of the plurality of tooth-receiving cavities, types of attachments associated with one or more of the plurality of tooth-receiving cavities, or precision cut information associated with one or more of the interproximal regions; and determining a magnitude of the load based on at least one of the clinical information or the treatment-related information.

16. The method of claim 1, wherein predicting whether the interproximal region will become damaged comprises:

determining a probability of the interproximal region being damaged based on the estimated strength of the aligner at the interproximal region.

17. The method of claim 1, further comprising:

generating a report indicating probabilities of the plurality of interproximal regions becoming damaged.

18. A method comprising:

gathering a virtual three-dimensional (3D) model representing an aligner for a dental arch of a patient, wherein the virtual 3D model of the aligner comprises a plurality of tooth-receiving cavities and a plurality of interproximal regions, wherein each tooth-receiving cavity of the plurality of tooth-receiving cavities is separated from an adjacent tooth-receiving cavity of the plurality of tooth-receiving cavities by an interproximal region of the plurality of interproximal regions; and analyzing, by a processing device, the plurality of interproximal regions of the virtual 3D model of the aligner, wherein analyzing an interproximal region of the plurality of interproximal regions of the virtual 3D model of the aligner comprises:

determining a plurality of cross-sectional slices of the interproximal region of the virtual 3D model of the aligner;

for each cross-sectional slice of the plurality of cross-sectional slices of the interproximal region of the virtual 3D model of the aligner, calculating one or more strength values;

determining a minimum strength value for the interproximal region of the virtual 3D model of the aligner from the one or more strength values calculated for the plurality of cross-sectional slices of the interproximal region of the virtual 3D model of the aligner;

determining whether the interproximal region of the virtual 3D model of the aligner satisfies a damage criterion based on the minimum strength value of the aligner at the interproximal region of the virtual 3D model of the aligner; and predicting whether the interproximal region of the virtual 3D model of the aligner will become damaged based on whether the interproximal region of the virtual 3D model of the aligner satisfies the damage criterion; and showing one or more interproximal regions of the aligner that are predicted to become damaged on the virtual 3D model of the aligner.

19. The method of claim 18, wherein determining a strength value of the one or more strength values for a cross-sectional slice of the plurality of cross-sectional slices comprises at least one of:

calculating an area moment of inertia for the cross-sectional slice; or calculating a stress associated with a load being applied to the interproximal region at the cross-sectional slice.

20. The method of claim 19, further comprising:

receiving material property information for a material to be used to manufacture the aligner;

wherein the area moment of inertia is computed about a first axis, and wherein calculating the stress associated with the load being applied to the interproximal region at the cross-sectional slice comprises:

applying the load to the cross-sectional slice about the first axis; and determining the stress associated with the cross-sectional slice based on the load, the material property information and the area moment of inertia.

21. The method of claim 18, wherein determining the one or more strength values comprises at least one of:

calculating a first area moment of inertia about a first axis of a plane defined by the cross-sectional slice;

calculating a second area moment of inertia about a second axis of the plane defined by the cross-sectional slice;

calculating a third area moment of inertia about an axis that is normal to the plane defined by the cross-sectional slice; or calculating a fourth area moment of inertia about a line on the plane defined by the cross-sectional slice.

22. The method of claim 18, further comprising:

determining locations of the plurality of interproximal regions, wherein a location of the interproximal region is determined based on:

determining a center of a first tooth-receiving cavity and an adjacent second tooth-receiving cavity that is separated by the interproximal region; and computing a first line between the first tooth-receiving cavity and the adjacent second tooth-receiving cavity.

23. The method of claim 22, wherein determining a cross-sectional slice of the interproximal region comprises:

determining an additional line that is perpendicular to the first line and to a z-axis; and determining a plane having a first axis defined by the additional line, wherein the cross-sectional slice is a slice of the interproximal region within the plane.

24. The method of claim 23, wherein a second axis of the plane is the z-axis.

25. The method of claim 22, wherein a first cross-sectional slice of the plurality of cross-sectional slices is offset from a second cross-sectional slice of the plurality of cross-sectional slices along the first line.

26. The method of claim 18, further comprising:

determining that a probability of the interproximal region being damaged exceeds a threshold; and determining that the interproximal region of the aligner is a probable point of damage.

27. The method of claim 26, further comprising:

selecting for the aligner a manufacturing flow for aligners comprising one or more probable points of damage.

28. The method of claim 26, further comprising:

responsive to determining that the aligner comprises the probable point of damage, implementing one or more corrective actions for the aligner.

29. The method of claim 28, wherein implementing the one or more corrective actions comprises modifying the virtual 3D model of the aligner to generate a modified virtual 3D model of the aligner.

30. The method of claim 29, wherein the virtual 3D model of the aligner was generated based on a virtual 3D model of a dental arch, and wherein modifying the virtual 3D model of the aligner comprises one or more of:

modifying a cutline radius of the virtual 3D model of the aligner;

modifying a thickness of a portion of the virtual 3D model of the aligner;

modifying a geometry of the virtual 3D model of the aligner;

inserting an indicator in the virtual 3D model of the aligner, wherein the indicator represents a recommended place to begin removing the aligner from a mold;

generating a first modified virtual 3D model of the dental arch by modifying one or more attachments on one or more teeth in the virtual 3D model of the dental arch, and generating the modified virtual 3D model of the aligner based on the first modified virtual 3D model of the dental arch; or generating a second modified virtual 3D model of the dental arch by adding or modifying a virtual filler at a location on the virtual 3D model of the dental arch that is associated with the interproximal region, and generating the modified virtual 3D model of the aligner based on the second modified virtual 3D model of the dental arch.

31. The method of claim 18, wherein analyzing the interproximal region further comprises:

determining a probability of the interproximal region being damaged based on the minimum strength value for the interproximal region.

* * * * *